(12) United States Patent
Hu et al.

(10) Patent No.: US 10,975,059 B2
(45) Date of Patent: Apr. 13, 2021

(54) SMALL MOLECULE BRD4 MODULATORS FOR HIV EPIGENETIC REGULATION

(71) Applicants: Haitao Hu, Galveston, TX (US); Jia Zhou, Galveston, TX (US); Zhiqing Liu, Galveston, TX (US)

(72) Inventors: Haitao Hu, Galveston, TX (US); Jia Zhou, Galveston, TX (US); Zhiqing Liu, Galveston, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 0 days.

(21) Appl. No.: 16/441,748

(22) Filed: Jun. 14, 2019

(65) Prior Publication Data

US 2019/0292168 A1     Sep. 26, 2019

Related U.S. Application Data

(63) Continuation-in-part of application No. PCT/US2017/066107, filed on Dec. 13, 2017.

(60) Provisional application No. 62/727,942, filed on Sep. 6, 2018.

(51) Int. Cl.
| | | |
|---|---|---|
| *C07D 403/02* | (2006.01) | |
| *C07D 403/06* | (2006.01) | |
| *A61P 31/18* | (2006.01) | |
| *C07D 207/48* | (2006.01) | |
| *C07D 401/06* | (2006.01) | |

(52) U.S. Cl.
CPC ............ *C07D 403/06* (2013.01); *A61P 31/18* (2018.01); *C07D 207/48* (2013.01); *C07D 401/06* (2013.01)

(58) Field of Classification Search
CPC .................................................. C07D 403/02
See application file for complete search history.

(56) References Cited

U.S. PATENT DOCUMENTS

2019/0359573 A1* 11/2019 Brasier et al. ....... C07D 413/06

OTHER PUBLICATIONS

Almahariq M, et al. (2013) A novel EPAC-specific inhibitor suppresses pancreatic cancer cell migration and invasion. Mol Pharmacol 83(1):122-128.
Arainga et al, HIV-1 cellular and tissue replication patterns in infected humanized mice, Scientific Reports, Mar. 21, 2016, 12 pgs.
Archin NM & Margolis DM (2014) Emerging strategies to deplete the HIV reservoir. Curr Opin Infect Dis 27(1):29-35.
Archin NM, et al. (2009) Expression of latent HIV induced by the potent HDAC inhibitor suberoylanilide hydroxamic acid. AIDS Res Hum Retroviruses 25(2):207-212.
Archin NM, et al. (2012) Administration of vorinostat disrupts HIV-1 latency in patients on antiretroviral therapy. Nature 487(7408):482-485.
Baell et al, Chemistry: Chemical con artists foil drug discovery, ResearchGate, 482, Nature, vol. 513, Sep. 25, 2014, 4 pgs.
Barnes-Seeman et al, Fluorinated Compounds in Medicinal Chemistry: Recent Applications, Synthetic Advances and Matched-Pair Analyses, Current Topics in Medicinal Chemistry, 2014, 14, 855-864.
Belkina et al, BET domain co-regulators in obesity, inflammation and cancer, Nature Reviews, Cancer, vol. 12, Jul. 2012, 14 pgs.
Bisgrove et al, Conserved P-TEFb-interacting domain of BRD4 inhibits HIV transcription, PNAS, Aug. 21, 2007, vol. 104, No. 34, 6 pgs.
Blazkova J, et al. (2012) Effect of histone deacetylase inhibitors on HIV production in latently infected, resting CD4(+) T cells from infected individuals receiving effective antiretroviral therapy. J Infect Dis 206(5):765-769.
Boehm et al, BET bromodomain-targeting compounds reactivate HIV from latency via a Tat-independent mechanism, Cell Cycle 12:3, 452-462, Feb. 1, 2013.
Brainard et al, Induction of Robust Cellular and Humoral Virus-Specific Adaptive Immune Responses in Human Immunodeficiency Virus-Infected Humanized BLT Mice, Journal of Virology, Jul. 2009, p. 7305-7321 vol. 83, No. 14.
Bruce et al, The Host Cell Sulfonation Pathway Contributes to Retroviral Infection at a Step Coincident with Provirus Establishment, PLoS Pathogens, Nov. 2008, vol. 4, Issue 11, 15 pgs.
Bullen et al, New ex vivo approaches distinguish effective and ineffective single agents for reversing HIV-1 latency in vivo, Nature Medicine vol. 20, No. 4, Apr. 2014, 6 pgs.
Cary DC & Peterlin BM (2016) Targeting the latent reservoir to achieve functional HIV cure. F1000Res 5.
Chen H, et al. (2012) 5-Cyano-6-oxo-1,6-dihydro-pyrimidines as potent antagonists targeting exchange proteins directly activated by cAMP. Bioorganic & medicinal chemistry letters 22(12):4038-4043.
Chen H, et al. (2013) A combined bioinformatics and chemoinformatics approach for developing asymmetric bivalent AMPA receptor positive allosteric modulators as neuroprotective agents. ChemMedChem 8(2):226-230.
Chen H, et al. (2013) Efficient Synthesis of ESI-09, A Novel Non-cyclic Nucleotide EPAC Antagonist. Tetrahedron Lett 54(12):1546-1549.
Chen H, et al. (2013) Fragment-based drug design and identification of HJC0123, a novel orally bioavailable STAT3 inhibitor for cancer therapy. European journal of medicinal chemistry 62:498-507.
Chen H, et al. (2014) Discovery of potent anticancer agent HJC0416, an orally bioavailable small molecule inhibitor of signal transducer and activator of transcription 3 (STAT3). Eur J Med Chem 82:195-203.
Chen H, et al. (2014) Recent advances in the discovery of small molecules targeting exchange proteins directly activated by cAMP (EPAC). J Med Chem 57(9):3651-3665.

(Continued)

*Primary Examiner* — John S Kenyon
(74) *Attorney, Agent, or Firm* — Hylton-Rodic Law PLLC

(57) ABSTRACT

The invention relates generally to novel small molecule BRD4 modulators for HIV, the preparation thereof as well as the use thereof.

15 Claims, 33 Drawing Sheets

(56) References Cited

OTHER PUBLICATIONS

Chen H, et al. (2015) Evolutions in fragment-based drug design: the deconstruction-reconstruction approach. Drug discovery today 20(1):105-113.
Choudhary et al, Latent HIV-1 Infection of Resting CD4+ T Cells in the Humanized Rag2-/-yc-/-Mouse, Journal of Virology, Jan. 2012, vol. 86, No. 1, p. 114-120.
Chun TW, Moir S, & Fauci AS (2015) HIV reservoirs as obstacles and opportunities for an HIV cure. Nat Immunol 16(6):584-589.
Cockrell et al, Gene delivery by lentivirus vectors, Mol Biotechnol (2007) 36:184-204.
Conrad et al, The Short Isoform of BRD4 Promotes HIV-1 Latency by Engaging Repressive SWI/SNF Chromatin-Remodeling Complexes, Molecular Cell, 67, 1001-1012, Sep. 21, 2017.
Contreras X, et al. (2009) Suberoylanilide hydroxamic acid reactivates HIV from latently infected cells. J Biol Chem 284(11):6782-6789.
Dahabieh MS, Battivelli E, & Verdin E (2015) Understanding HIV latency: the road to an HIV cure. Annu Rev Med 66:407-421.
Darcis et al, HIV Latency: Should We Shock or Lock?, Trends in Immunology, Mar. 2017, vol. 38, No. 3, 12 pgs.
Deeks et al, Towards an HIV cure: a global scientific strategy, Nature Reviews, Immunology, vol. 12, Aug. 2012, 8 pgs.
Deeks SG (2012) HIV: Shock and kill. Nature 487(7408):439-440.
Denton et al, Humanized Mouse Models of HIV Infection, NIH Public Access, AIDS Rev. 2011, 13(3): 135-148.
Denton et al, Using animal models to overcome temporal, spatial and combinatorial challenges in HIV persistence research, Journal of Translational Medicine, (2016) 14:44, 13 pgs.
Deruaz et al, Humanized mouse models of latent HIV infection, ScienceDirect, Current Opinion in Virology 2017, 25:97-104.
Dhalluin et al, Structure and ligand of a histone acetyltransferase bromodomain, Nature, vol. 399, Jun. 3, 1999, 8 pgs.
DuChene et al, Suv39H1 and HP1? are responsible for chromatin-mediated HIV-1 transcriptional silencing and post-integration latency, The EMBO Journal (2007) 26, 424-435.
Fernando K, Hu H, Ni H, Hoxie JA, & Weissman D (2007) Vaccine-delivered HIV envelope inhibits CD4(+) T-cell activation, a mechanism for poor HIV vaccine responses. Blood 109(6):2538-2544.
Filippakopoulos et al, Histone Recognition and Large-Scale Structural Analysis of the Human Bromodomain Family, Cell 149, 214-231, Mar. 30, 2012.
Filippakopoulos et al, Selective inhibition of BET bromodomains, Nature, vol. 468, Dec. 23-30, 2010, 7 pgs.
Friedman et al, Epigenetic Silencing of HIV-1 by the Histone H3 Lysine 27 Methyltransferase Enhancer of Zeste 2, Journal of Virology, Sep. 2011, p. 9078-9089, vol. 85, No. 17.
Gelman BB, et al. (2012) The National NeuroAIDS Tissue Consortium brain gene array: two types of HIV-associated neurocognitive impairment. PLoS One 7(9):e46178.
Hakre et al, Epigenetic regulation of HIV latency, Lippincott Williams & Wilkins, Current Opinion in HIV and AIDS 2011, 6:19-24.
Haznedar et al, Single- and multiple-dose disposition kinetics of sunitinib malate, a multitargeted receptor tyrosine kinaseinhibitor: comparative plasma kinetics in non-clinical species, Cancer Chemother Pharmacol (2009) 64:691-706.
He et al, Counterregulation of Chromatin Deacetylation and Histone Deacetylase Occupancy at the Integrated Promoter of Human Immunodeficiency Virus Type 1 (HIV-1) by the HIV-1 Repressor YY1 and HIV-1 Activator Tat, Molecular and Cellular Biology, May 2002, p. 2965-2973 vol. 22, No. 9.
He et al, HIV-1 Tat and Host AFF4 Recruit Two Transcription Elongation Factors into a Bifunctional Complex for Coordinated Activation of HIV-1 Transcription, Molecular Cell 38, 428-438, May 14, 2010.

Heaton RK, et al. (2015) Neurocognitive change in the era of HIV combination antiretroviral therapy: the longitudinal CHARTER study. Clin Infect Dis 60(3):473-480.
Ho et al, Replication-Competent Noninduced Proviruses in the Latent Reservoir Increase Barrier to HIV-1 Cure, Cell 155, 540-551, Oct. 24, 2013.
Hu H, et al. (2011) SIV antigen immunization induces transient antigen-specific T cell responses and selectively activates viral replication in draining lymph nodes in retroviral suppressed rhesus macaques. Retrovirology 8:57.
Hu H, et al. (2014) Preferential infection of human Ad5-specific CD4 T cells by HIV in Ad5 naturally exposed and recombinant Ad5-HIV vaccinated individuals. Proc Natl Acad Sci U S A 111(37):13439-13444.
Hu H, Fernando K, Ni H, & Weissman D (2008) HIV envelope suppresses CD4+ T cell activation independent of T regulatory cells. J Immunol 180(8):5593-5600.
Huang et al, A Novel Bromodomain Inhibitor Reverses HIV-1 Latency through Specific Binding with BRD4 to Promote Tat and P-TEFb Association, Frontiers in Microbiology, Jun. 2017, vol. 8, Article 1035, 11 pgs.
Huang et al, Brd4 Coactivates Transcriptional Activation of NF-κB via Specific Binding to Acetylated RelA, Molecular and Cellular Biology, Mar. 2009, p. 1375-1387, vol. 29, No. 5.
International ASSWGoHIVC, et al. (2012) Towards an HIV cure: a global scientific strategy. Nat Rev Immunol 12 (8):607-614.
Jiang et al, Mammalian mediator of transcriptional regulation and its possible role as an end-point of signal transduction pathways, Proc. Natl. Acad. Sci. USA, vol. 95, pp. 8538-8543, Jul. 1998, Biochemistry.
Jung et al, Affinity Map of Bromodomain Protein 4 (BRD4) Interactions with the Histone H4 Tail and the Small Molecule Inhibitor JQ1, The Journal of Biological Chemistry, vol. 289, No. 13, pp. 9304-9319, Mar. 28, 2014.
Kao et al, Anti-termination of transcription within the long terminal repeat of HIV-1 by tat gene product, Nature, vol. 330, Dec. 3, 1987, 5 pgs.
Karn, A new BET on the control of HIV latency, Cell Cycle, 12:4, 542-546; Feb. 15, 2013.
Keedy et al, Limited Group of Class I Histone Deacetylases Acts to Repress Human Immunodeficiency Virus Type 1 Expression, Journal of Virology, May 2009, p. 4749-4756 vol. 83, No. 10.
Kessing et al, In Vivo Suppression of HIV Rebound by Didehydro-Cortistatin A, a "Block-and-Lock" Strategy for HIV-1 Treatment, Cell Reports 21, 600-611, Oct. 17, 2017.
Kurimchak et al, Resistance to BET Bromodomain Inhibitors Is Mediated by Kinome Reprogramming in Ovarian Cancer, Cell Reports 16, 1273-1286, Aug. 2, 2016.
Li et al, Existing drugs as broad-spectrum and potent inhibitors for Zika virus by targeting NS2B-NS3 interaction, Cell Research (2017) 27:1046-1064.
Li et al, The BET bromodomain inhibitor JQ1 activates HIV latency through antagonizing Brd4 inhibition of Tat-transactivation, Nucleic Acids Research, 2013, vol. 41, No. 1, 277-287.
Lipinski CA, Lombardo F, Dominy BW, & Feeney PJ (2001) Experimental and computational approaches to estimate solubility and permeability in drug discovery and development settings. Advanced drug delivery reviews 46(1-3):3-26.
Liu et al, Discovery of potent and selective BRD4 inhibitors capable of blocking TLR3-induced acute airway inflammation, European Journal of Medicinal Chemistry 151 (2018) 450-461.
Liu et al, Drug Discovery Targeting Bromodomain-Containing Protein 4, Journal of Medicinal Chemistry, 2017, 60, 4533-4558.
Liu et al, HIV-1 functional cure: will the dream come true?, BMC Medicine (2015) 13:284, 12 pgs.
Liu et al, Priming and Activation of Inflammasome by Canarypox Virus Vector ALVAC via the cGAS/IFI16-STING-Type I IFN Pathway and AIM2 Sensor, The Journal of Immunology, 2017; 199:3293-3305.
Liu et al, The Ubiquitin Ligase Siah1 Controls ELL2 Stability and Formation of Super Elongation Complexes to Modulate Gene Transcription, Molecular Cell 46, 325-334, May 11, 2012.

(56) References Cited

OTHER PUBLICATIONS

Liu F, et al. (2016) Sequential Dysfunction and Progressive Depletion of Candida albicans-Specific CD4 T Cell Response in HIV-1 Infection. PLoS Pathog 12(6):e1005663.
Logan et al, Asymmetric synthesis of batrachotoxin: Enantiomeric toxins show functional divergence against NaV, sciencemag.org, Nov. 18, 2016, vol. 354, Issue 6314, 6 pgs.
Lu et al, The BET inhibitor OTX015 reactivates latent HIV-1 through P-TEFb, Scientific Reports, 6:24100, Apr. 12, 2016, 13 pgs.
Luo et al, The super elongation complex (SEC) family in transcriptional control, Nature Reviews, Molecular Cell Biology, vol. 13, Sep. 2012, 5 pgs.
Ma et al, Time-Resolved Fluorescence Assays, Methods in Molecular Biology, vol. 1439, 2016, 12 pgs.
Marban et al, Recruitment of chromatin-modifying enzymes by CTIP2 promotes HIV-1 transcriptional silencing, The EMBO Journal (2007) 26, 412-423.
Marin B, et al. (2009) Non-AIDS-defining deaths and immunodeficiency in the era of combination antiretroviral therapy. AIDS 23(13):1743-1753.
Marsden et al, HIV Latency in the Humanized BLT Mouse, Journal of Virology, p. 339-347, Nov. 9, 2011.
Marsilje et al, Synthesis, Structure-Activity Relationships, and in Vivo Efficacy of the Novel Potent and Selective Anaplastic Lymphoma Kinase (ALK) Inhibitor 5-Chloro-N2-(2-isopropoxy-5-methyl-4-(piperidin-4-yl)phenyl)-N4-(2-(isopropylsulfonyl)phenyl)pyrimidine-2,4-diamine (LDK378) Currently in Phase 1 and Phase 2 Clinical Trials, Journal of Medicinal Chemistry, 2013, 56, 5675-5690.
Mbonye et al, Control of HIV Latency by Epigenetic and Non-Epigenetic Mechanisms, Current HIV Research, 2011, 9, 554-567.
Mbonye et al, Transcriptional control of HIV latency: Cellular signaling pathways, epigenetics, happenstance and the hope for a cure, Virology 454-455 (2014) 328-339.
Mousseau et al, An Analog of the Natural Steroidal Alkaloid Cortistatin a Potently Suppresses Tat-Dependent HIV Transcription, Cell Host & Microbe 12, 97-108, Jul. 19, 2012.
Mousseau et al, The Tat Inhibitor Didehydro-Cortistatin A Prevents HIV-1 Reactivation from Latency, mBio, Jul./Aug. 2015, vol. 6, Issue 4, 14 pgs.
Murry et al, Sulfonation pathway inhibitors block reactivation of latent HIV-1, Virology 471-473 (2014) 1-12.
Nauta et al, Enhanced engraftment of umbilical cord blood-derived stem cells in NOD/SCID mice by cotransplantation of a second unrelated cord blood unit, Experimental Hematology 33 (2005) 1249-1256.
Nusbaum et al, Pulmonary Tuberculosis in Humanized Mice Infected with HIV-1, Scientific Reports, 6:21522, Feb. 24, 2016, 11 pgs.
Obach et al, Can In Vitro Metabolism-Dependent Covalent Binding Data in Liver Microsomes Distinguish Hepatotoxic from Nonhepatotoxic Drugs? An Analysis of 18 Drugs with Consideration of Intrinsic Clearance and Daily Dose, Chem. Res. Toxicol. 2008, 21, 1814-1822.
Ott et al, The Control of HIV Transcription: Keeping RNA Polymerase II on Track, Cell Host & Microbe 10, Nov. 17, 2011, 10 pgs.
Padmanabhan et al, Bromodomain and extra-terminal (BET) family proteins: New therapeutic targets in major diseases, Indian Academy of Sciences J. Biosci. 41(2), Jun. 2016, 295-311.
Perez et al, Establishment of HIV-1 resistance in CD4+ T cells by genome editing using zinc-finger nucleases, Nature Biotechnology, vol. 26, No. 7, Jul. 2008.
Pires DE, Blundell TL, & Ascher DB (2015) pkCSM: Predicting Small-Molecule Pharmacokinetic and Toxicity Properties Using Graph-Based Signatures. J Med Chem 58(9):4066-4072.
Quinonez et al, Lentiviral Vectors for Gene Delivery into Cells, DNA and Cell Biology, vol. 21, No. 12, 2002, pp. 937-951.
Ruelas DS & Greene WC (2013) An integrated overview of HIV-1 latency. Cell 155(3):519-529.
Sarzotti-Kelsoe et al, Optimization and validation of the TZM-bl assay for standardized assessments of neutralizing antibodies against HIV-1, Journal of Immunological Methods 409 (2014) 131-146.
Sedaghat AR, Siliciano RF, & Wilke CO (2008) Low-level HIV-1 replication and the dynamics of the resting CD4+ T cell reservoir for HIV-1 in the setting of HAART. BMC Infect Dis 8:2.
Siliciano RF & Greene WC (2011) HIV latency. Cold Spring Harb Perspect Med 1(1):a007096.
Sobhian et al, HIV-1 Tat Assembles a Multifunctional Transcription Elongation Complex and Stably Associates with the 7SK snRNP, Molecular Cell 38, 439-451, May 14, 2010.
Spina CA, et al. (2013) An in-depth comparison of latent HIV-1 reactivation in multiple cell model systems and resting CD4+ T cells from aviremic patients. PLoS Pathog 9(12):e1003834.
Suzuki et al, Prolonged transcriptional silencing and CpG methylation induced by siRNAs targeted to the HIV-1 promoter region, Journal of RNAi and Gene Silencing, Oct. 2005, vol. 1, No. 2, 66-78.
Suzuki et al, Promoter Targeting shRNA Suppresses HIV-1 Infection In vivo Through Transcriptional Gene Silencing, Molecular Therapy-Nucleic Acids (2013) 2, e137, 10 pgs.
Swan et al, T-cell protection and enrichment through lentiviral CCR5 intrabody gene delivery, Gene Therapy (2006) 13, 1480-1492.
Takahashi et al, Human Mediator Subunit MED26 Functions as a Docking Site for Transcription Elongation Factors, Cell 146, 92-104, Jul. 8, 2011.
Tetko IV (2005) Computing chemistry on the web. Drug discovery today 10(22):1497-1500.
Tetko IV, et al. (2005) Virtual computational chemistry laboratory—design and description. Journal of computer-aided molecular design 19(6):453-463.
Turner et al, Characterization of an HIV-Targeted Transcriptional Gene-Silencing RNA in Primary Cells, Human Gene Therapy, 23:473-483 (May 2012).
Turner et al, Mobilization-competent Lentiviral Vector-mediated Sustained Transcriptional Modulation of HIV-1 Expression, www.moleculartherapy.org, vol. 17, No. 2, 360-368, Feb. 2009.
Tyagi et al, CBF-1 promotes transcriptional silencing during the establishment of HIV-1 latency, The EMBO Journal (2007) 26, 4985-4995.
Van Lint C, Bouchat S, & Marcello A (2013) HIV-1 transcription and latency: an update. Retrovirology 10:67.
Vollmuth et al, Structures of the Dual Bromodomains of the P-TEFb-activating Protein Brd4 at Atomic Resolution, The Journal of Biological Chemistry, vol. 284, No. 52, pp. 36547-36556, Dec. 25, 2009.
Wang et al, CCR5 Gene Disruption via Lentiviral Vectors Expressing Cas9 and Single Guided RNA Renders Cells Resistant to HIV-1 Infection, PLOS ONE, Dec. 26, 2014, 26 pgs.
Watanabe et al, Humanized NOD/SCID/IL2Rγnull Mice Transplanted with Hematopoietic Stem Cells under Nonmyeloablative Conditions Show Prolonged Life Spans and Allow Detailed Analysis of Human Immunodeficiency Virus Type 1 Pathogenesis, Journal of Virology, Dec. 2007, p. 13259-13264, vol. 81, No. 23.
Wild CT, et al. (2016) Functionalized N,N-Diphenylamines as Potent and Selective EPAC2 Inhibitors. ACS Med Chem Lett 7(5):460-464.
Wilen et al, Engineering HIV-Resistant Human CD4+ T Cells with CXCR4-Specific Zinc-Finger Nucleases, PLoS Pathogens, Apr. 2011, vol. 7, Issue 4, 15 pgs.
Williams et al, NF-κB p50 promotes HIV latency through HDAC recruitment and repression of transcriptional initiation, The EMBO Journal (2006) 25, 139-149.
Wu et al, The Double Bromodomain-containing Chromatin Adaptor Brd4 and Transcriptional Regulation, The Journal of Biological Chemistry, vol. 282, No. 18, pp. 13141-13145, May 4, 2007.
Xing S, et al. (2011) Disulfiram reactivates latent HIV-1 in a Bcl-2-transduced primary CD4+ T cell model without inducing global T cell activation. J Virol 85(12):6060-6064.
Yamagishi et al, Retroviral delivery of promoter-targeted shRNA induces long-term silencing of HIV-1 transcription, Microbes and Infection 11 (2009) 500-508.
Yang et al, Recruitment of P-TEFb for Stimulation of Transcriptional Elongation by the Bromodomain Protein Brd4, Molecular Cell, vol. 19, 535-545, Aug. 19, 2005.

(56) References Cited

OTHER PUBLICATIONS

Ye N, et al. (2015) Structure-Activity Relationship Studies of Substituted 2-(Isoxazol-3-yl)-2-oxo-N'-phenyl-acetohydrazonoyl Cyanide Analogues: Identification of Potent Exchange Proteins Directly Activated by cAMP (EPAC) Antagonists. J Med Chem 58(15):6033-6047.

Ye n, et al. (2017) Identification of novel 2-(benzo[ d]isoxazol-3-yl)-2-oxo-Nphenylacetohydrazonoyl cyanide analogues as potent EPAC antagonists.

Zhou et al, RNA Polymerase II Elongation Control, Annual Review of Biochemistry, 2012, 81:119-43.

Zhu et al, Reactivation of Latent HIV-1 by Inhibition of BRD4, Cell Reports 2, 807-816, Oct. 25, 2012.

Zhu Y, et al. (2015) Biochemical and pharmacological characterizations of ESI-09 based EPAC inhibitors: defining the ESI-09 "therapeutic window". Sci Rep 5:9344.

Hu et al, Distinct gene-expression profiles associated with the susceptibility of pathogen-specific CD4 T cells to HIV-1 infection, Immunobiology, Blood, Feb. 14, 2013, vol. 121, No. 7, 1136-1144.

Jang et al, The Bromodomain Protein Brd4 Is a Positive Regulatory Component of P-TEFb and Stimulated RNA Polymerase II-Dependent Transcription, Molecular Cell, vol. 19, 523-534, Aug. 19, 2005.

Tian et al, Selective Antagonists of the Brochiolar Epithelial NF-kB-Bromodomain-Containing Protein 4 Pathway in Viral-Induced Airway Inflammation, Cell Reports 23, 1138-1151, Apr. 24, 2018.

\* cited by examiner

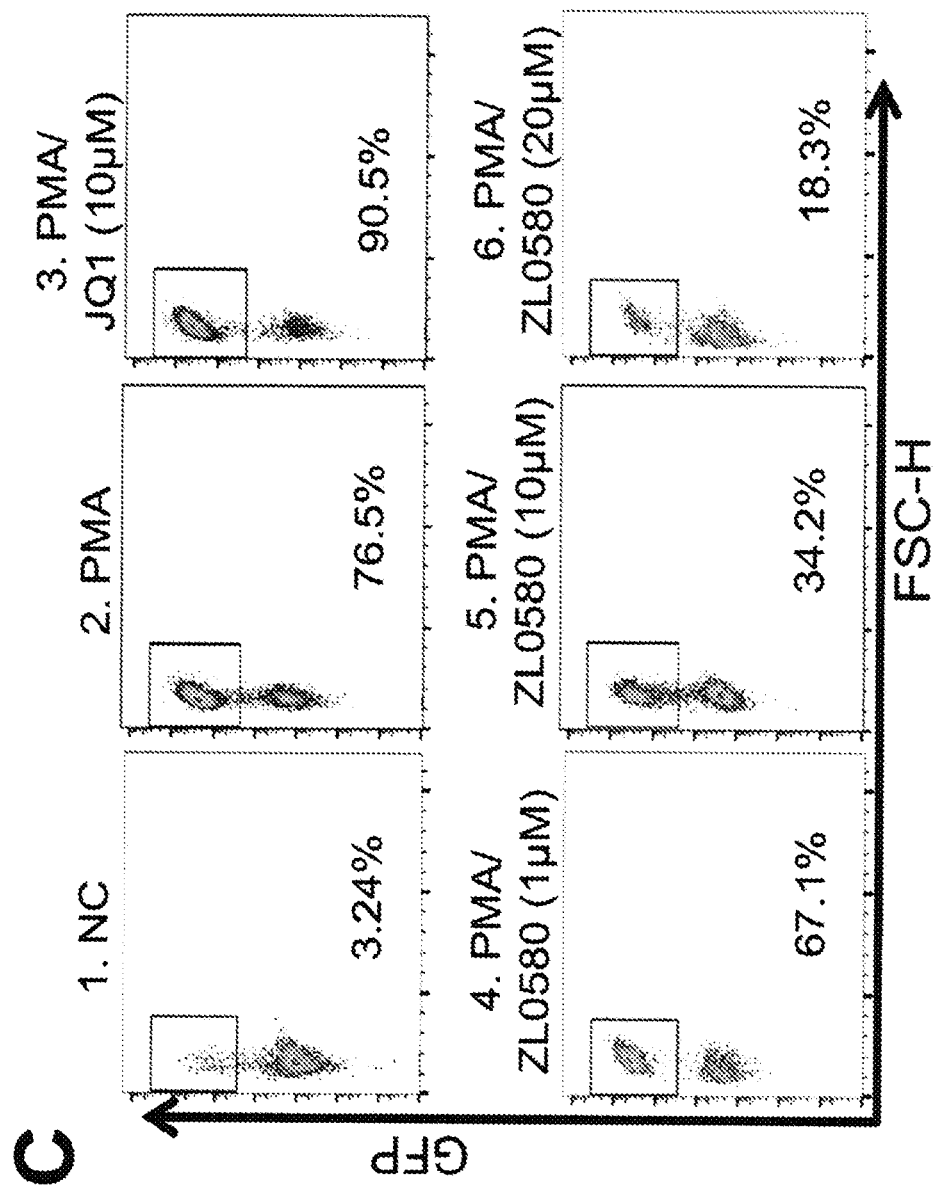

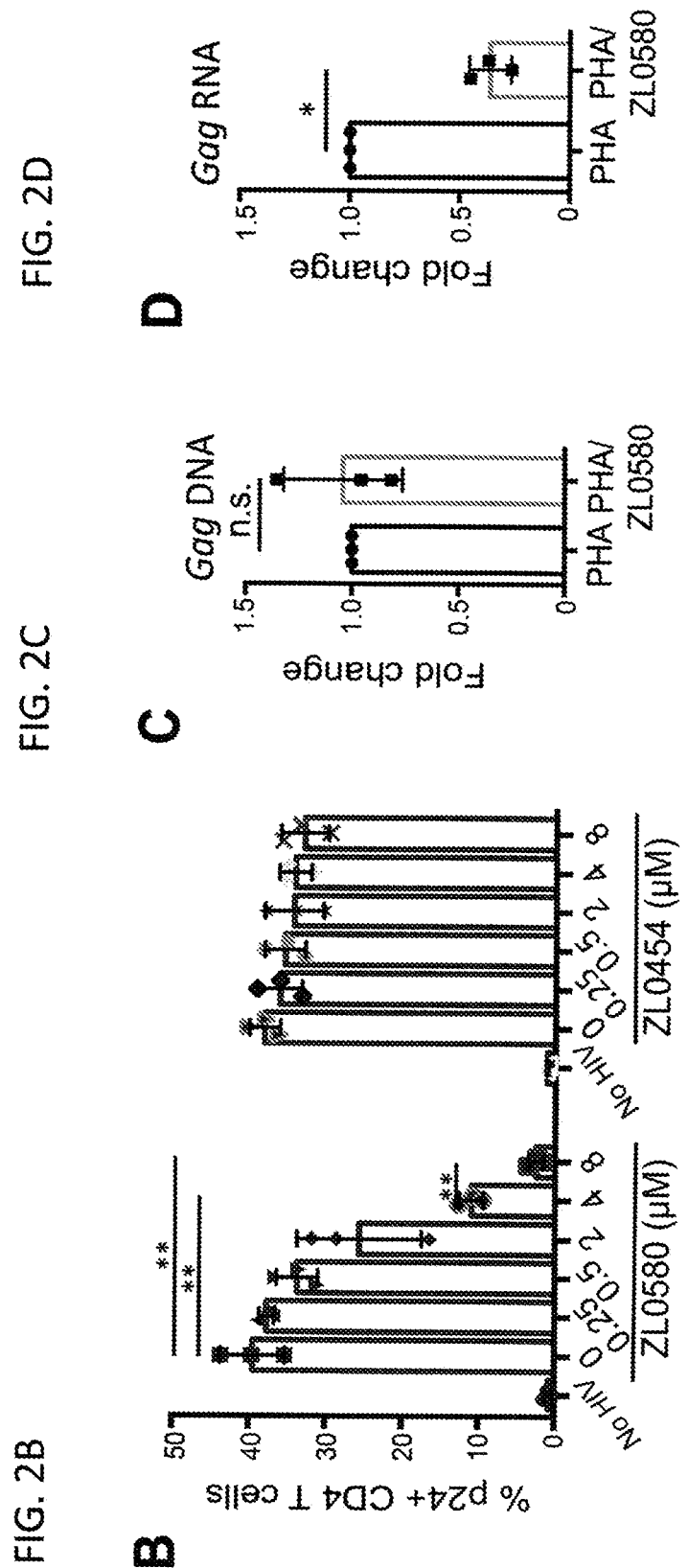

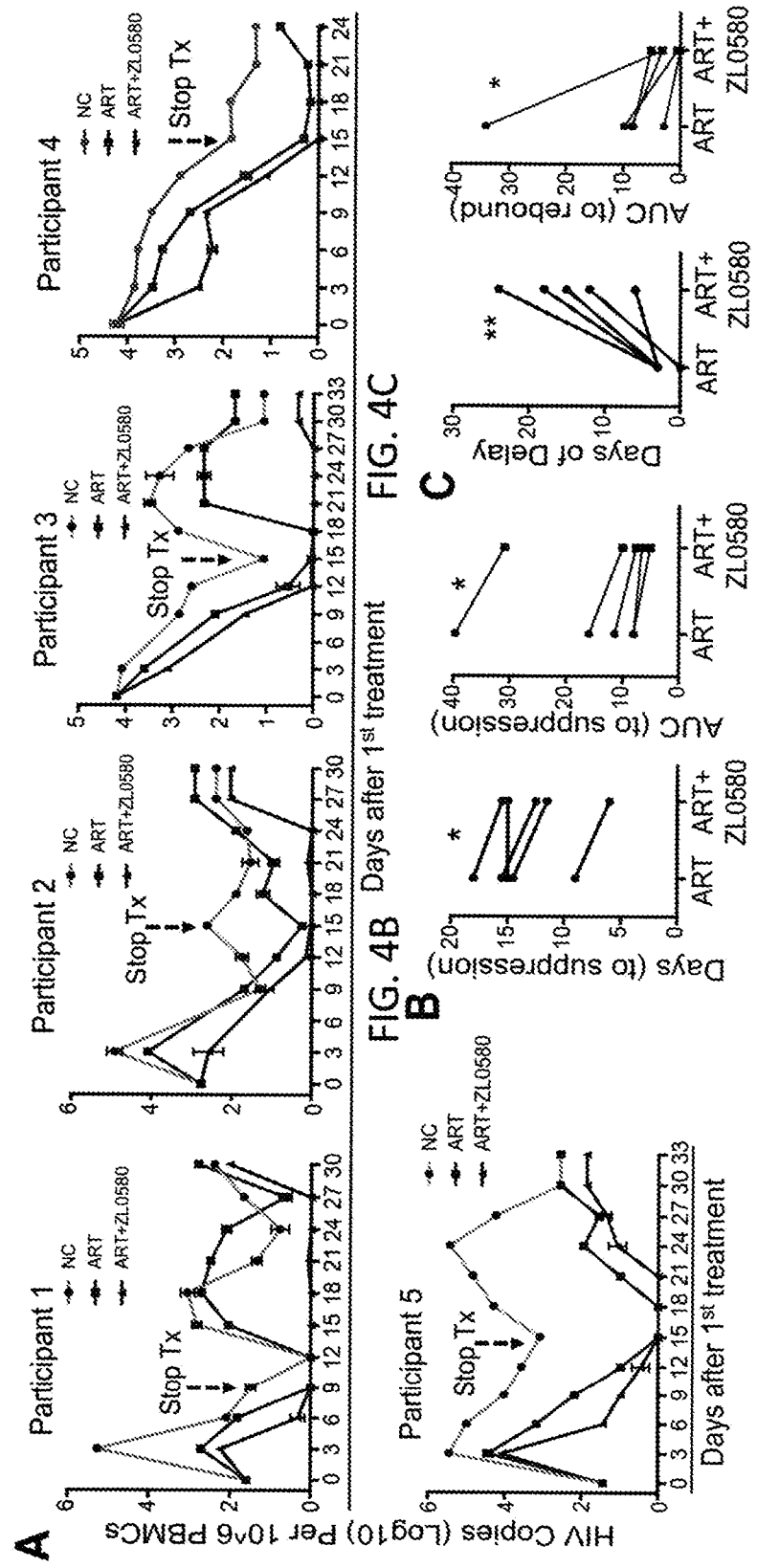

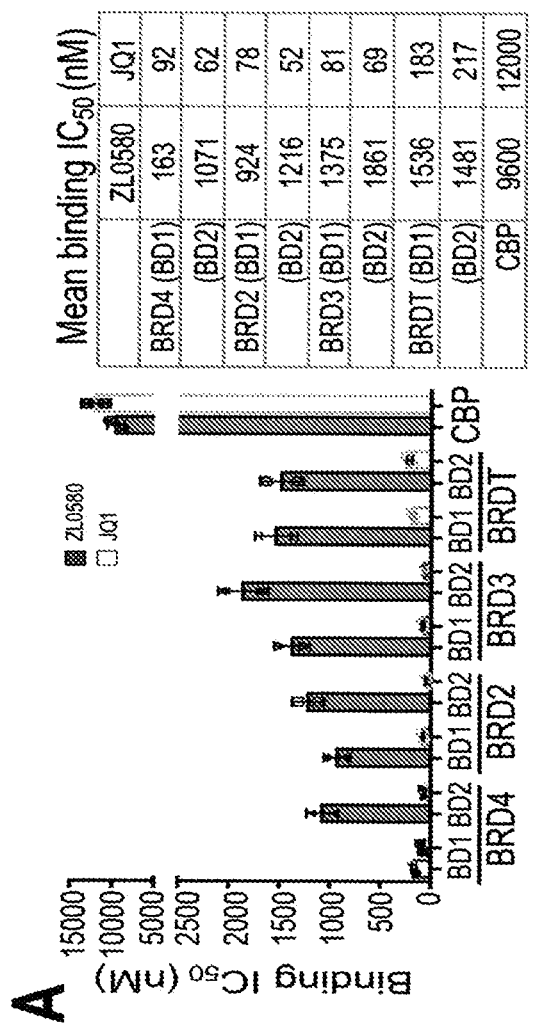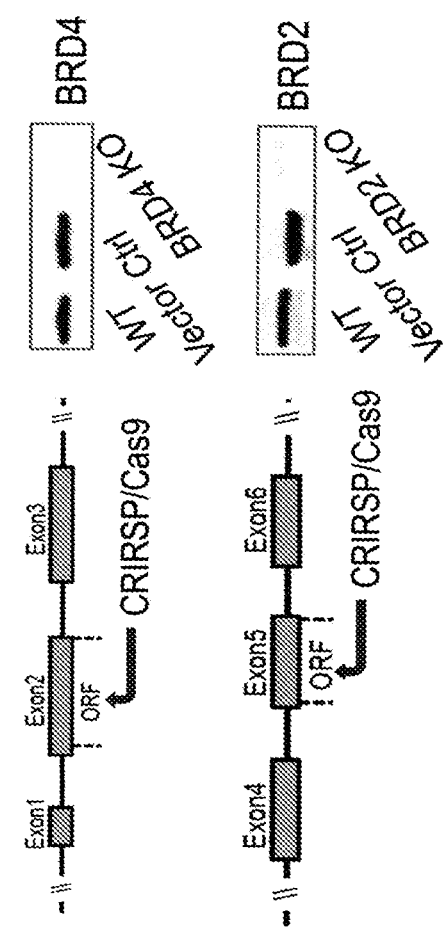
FIG. 5A
FIG. 5B

FIG. 9

| Days | Treatment | Cq (3'-LTR) | | Cq (GAPDH) | |
|---|---|---|---|---|---|
| | | Replicate 1 | Replicate 2 | Replicate 1 | Replicate 2 |
| 2 | NC | 27.04 | 26.46 | 18.08 | 18.02 |
| | ZL0580 | 26.19 | 25.23 | 17.57 | 17.73 |
| | JQ1 | 21.69 | 21.18 | 17.56 | 17.88 |
| 7 | NC | 28.38 | 27.94 | 19.57 | 19.26 |
| | ZL0580 | 31.08 | 31.92 | 19.57 | 19.26 |
| | JQ1 | 24.08 | 24.10 | 19.79 | 19.52 |
| 14 | NC | 26.67 | 26.40 | 18.34 | 18.13 |
| | ZL0580 | 31.12 | 31.23 | 18.55 | 18.69 |
| | JQ1 | 25.40 | 25.42 | 18.92 | 19.08 |
| No cDNA-Template Control | | 0 | 0 | 0 | 0 |

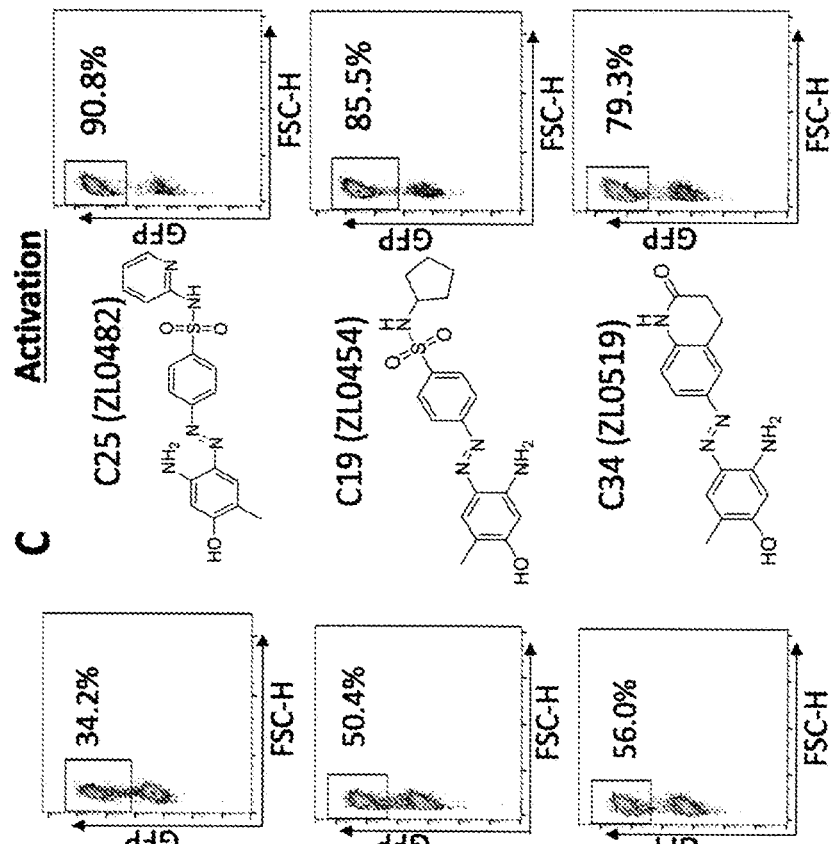
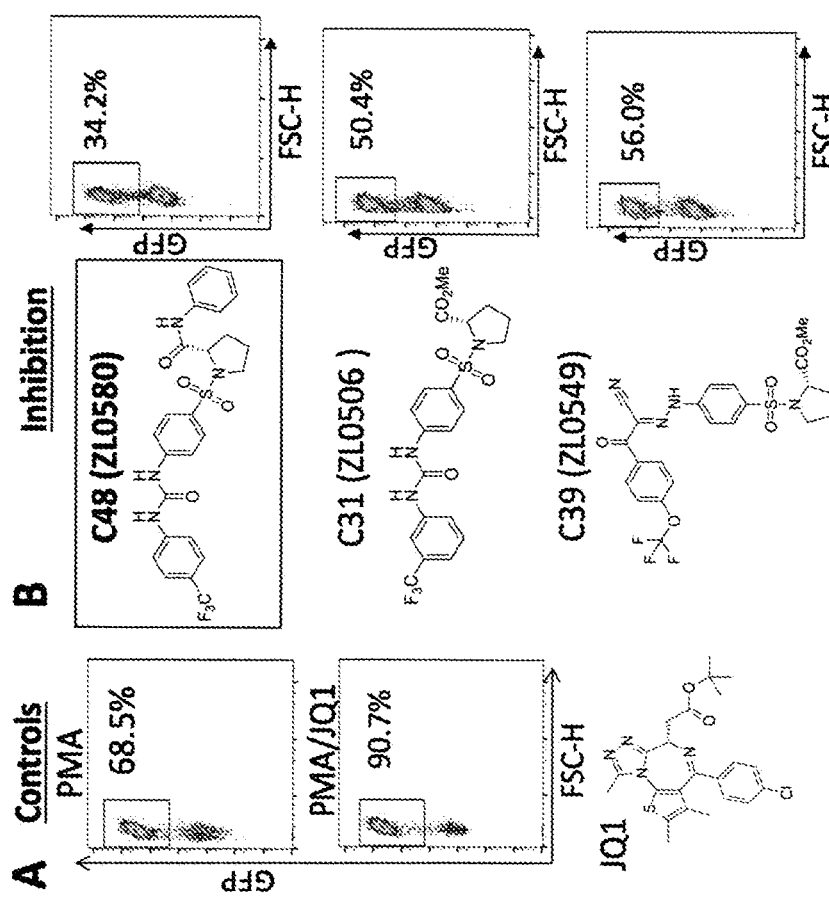

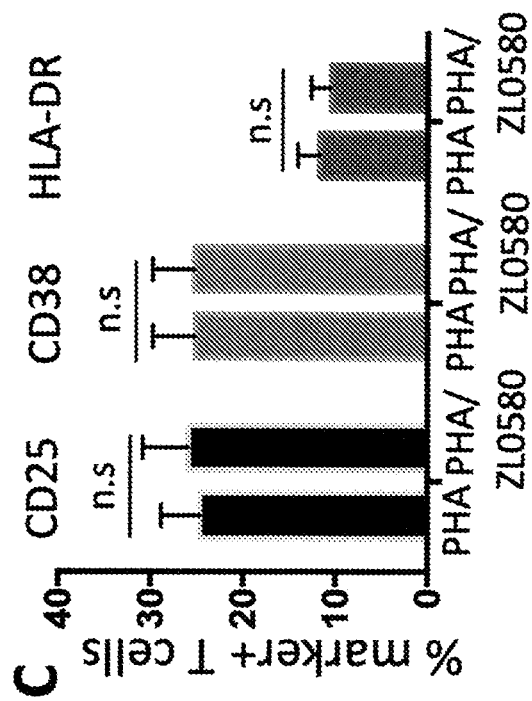
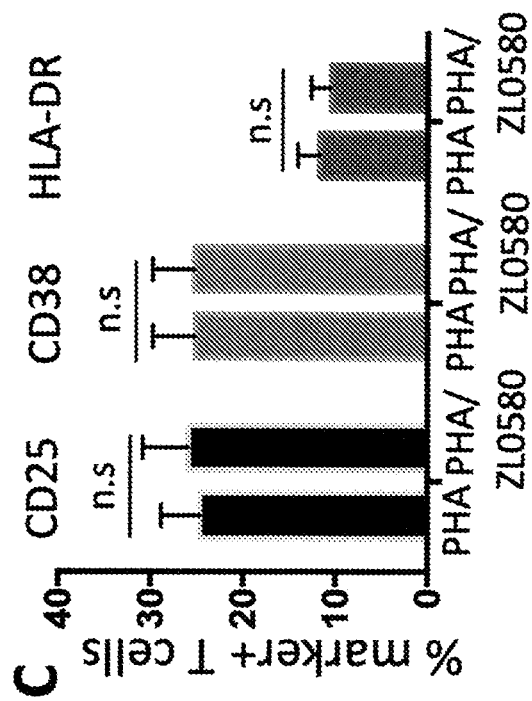
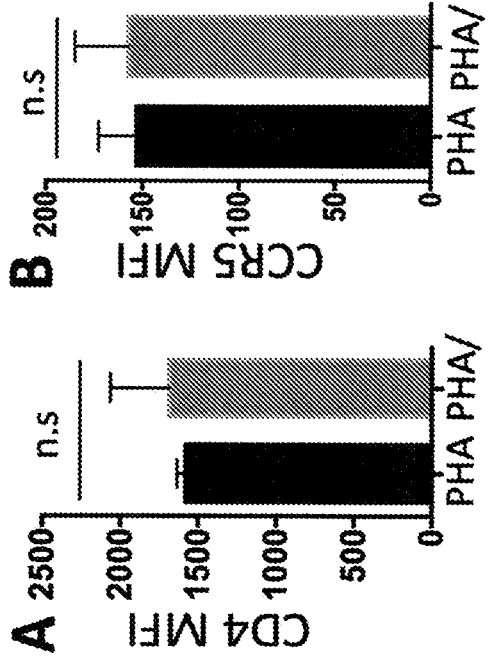
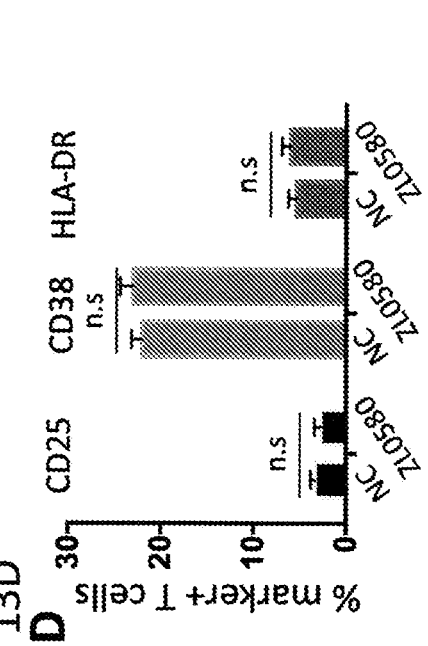

SMALL MOLECULE BRD4 MODULATORS FOR HIV EPIGENETIC REGULATION

CROSS-REFERENCE TO RELATED APPLICATIONS

This application claims the benefit of International Appl. No. PCT/US2017/066107, filed Dec. 13, 2017 and Provisional Appl. No. 62/727,942, filed Sep. 6, 2018. The content of the aforesaid applications are relied upon and are incorporated by reference herein in their entirety.

FIELD OF THE INVENTION

The field of the invention relates generally to novel BRD4 modulators for HIV epigenetic regulation, and the preparation thereof and the use thereof.

BACKGROUND

Human immunodeficiency virus-1 (HIV) causes persistent and latent infection, posing a major obstacle for eradication of the virus (1-4). While anti-retroviral therapy (ART) is highly effective in controlling HIV replication and reducing viremia, it cannot eradicate the virus and manifests significant limitations. Low levels of HIV replication continuously occur in ART-suppressed individuals and the latent reservoir is capable of rapidly producing infectious virus when ART is discontinued (2, 5). The effects of residual HIV infection remain evident even under ART, including a range of metabolic, immunologic, and neurologic co-morbidities (6). In addition, ART treatment requires life-long administration to achieve sustained viral suppression. With the expanded usage of ART, HIV has become more drug resistant, which also erodes the efficacy of ART (1). Due to these limitations, new treatment paradigm that aims to target latent HIV reservoirs for eradication or cure is urgently needed.

A current strategy for HIV eradication involves reactivation of latent HIV from latent reservoirs so that the latently infected cells can be eliminated by direct cytopathic effect or immune-mediated destruction ("shock and kill" approach) (7-10). However, this strategy has so far produced less convincing results and has faced significant challenges (11-13). Current latency reversing agents (LRAs) manifest limited in vivo efficacy and cannot thoroughly wake up HIV in some "deep" non-inducible latent reservoirs (12). Alternative approaches aiming to transcriptionally repress HIV provirus to induce an aviremic state in the absence of ART, called "functional cure", have gained substantial interest and been a focus of research (reviewed in (13, 14). Integrated HIV proviral transcription in infected cells undergo multiple layers of epigenetic regulation (15, 16). It has been suggested that cellular epigenetic machinery involved in HIV transcriptional regulation can be promising targets for modulation to repress or silencing HIV provirus. However, to this end, while substantial work has been conducted to understand epigenetic mechanisms underlying HIV transcriptional regulation (15-17)), effective approaches for targeting these mechanisms to repress HIV provirus remain limited.

The Bromodomain and Extra-Terminal Domain (BET) protein family member BRD4 is an important epigenetic regulator that localizes to DNA via binding acetylated histones and participates in the control of cellular and integrated HIV gene transcription through multiple functional activities (18-21). BRD4 has been shown to repress HIV transcription by competing with HIV Tat for cellular active p-TEFb/CDK9 (20). Inhibition of BET/BRD4 by the pan-BET inhibitor, JQ1, can relieve such competition between BRD4 and Tat and therefore reactivate latent HIV (19, 20). Given the roles of BET/BRD4 in HIV transcriptional regulation, there has been interested in identifying novel modulatory agents that can selectively target BET/BRD4 to modulate HIV transcriptional activation or repression. After screening a novel class of small-molecule modulators of BRD4 designed and synthesized in house (reviewed in (22)), the inventors surprisingly discovered report identification of a novel lead compound, named ZL0580, that selectively targets BRD4 but intriguingly induces a functional impact on HIV transcription distinct from JQ1. Instead of activating HIV, compound ZL0580, an exemplary embodiment of the invention, can suppress HIV transcription and viral replication. Functional analysis shows that this compound can potently suppress HIV in various cellular models, including transformed cell line (J-Lat cells), and human primary PBMCs (both in vitro and ex vivo HIV-infected models). The inventors found that unlike JQ1 which binds to multiple BET proteins, ZL0580 is highly specific to BRD4, but not to other BET proteins. CRISPR/Cas9 knockout experiments show that BRD4 functionally mediates the HIV suppressive effect of the lead compound ZL0580. Mechanistically, it was discovered that ZL0580 suppresses HIV by inhibiting Tat transactivation and HIV transcription elongation, including reduced p-TEFb/CDK9 binding to Tat, reduced cellular ELL2 expression and decreased RNA polymerase II (RNAPII) activation.

This background information is provided for the purpose of making information believed by the applicant to be of possible relevance to the present invention. No admission is necessarily intended, nor should it be construed, that any of the preceding information constitutes prior art against the present invention.

SUMMARY

It is to be understood that both the foregoing general description of the invention and the following detailed description are exemplary, and thus do not restrict the scope of the invention.

The inventors have surprisingly discovered certain novel small molecules that may be used as BRD4 modulators. In some aspects of the invention these novel small molecules may be used to suppress HIV. In some aspects of the invention these novel small molecules may be used to suppress HIV in J-Lat cells.

One aspect of the invention pertains to a compound of Formula I, or a pharmaceutically acceptable salt thereof, having the formula:

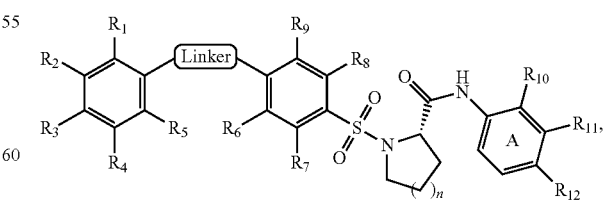

Formula I wherein
R1, R2, R3, R4, R5, R6, R7, R8 and R9 are independently H, —OH, alkyl, alkoxy, halogen, —NH2, —OCF3 or —CF3;

R10, R11 and R12 are independently H, —OH, halogen, alkoxy, —NH2, —CF3, —(CO)R13 where R13 is alkyl, alkoxy, amino, or alkylamino; —NR22R23, where R22 and R23 are independently H, alkyl; or R22 and R23 are optionally joined to form a 3-6 membered substituted or unsubstituted heterocycle having 1-3 heteroatoms;

Linker is —(CO)NR25-, NR26 or —R27(CO)—, wherein R25, R26 and R27 are independently H or C1-C6 alkyl;

n is 0-3 and

Ring A is chosen from 5-6 membered aromatic rings containing 0-3 nitrogen atoms.

Another aspect of the invention pertains to a compound of Formula II, or a pharmaceutically acceptable salt thereof, having the formula:

Formula II

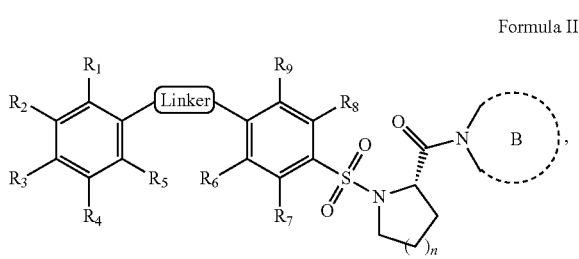

wherein

R1, R2, R3, R4, R5, R6, R7, R8 and R9 are independently H, —OH, alkyl, alkoxy, halogen, —NH2, —OCF3 or —CF3;

Ring B is chosen from substituted or unsubstituted C4-C7 aliphatic rings;

Linker is —NHCONR24-, —CONR25-, NR26 or —R27CO—, where R24, R25, R26 and R27 are independently H or C1-C6 alkyl; and n is 0-3.

Another aspect of the invention pertains to a compound of Formula III, or a pharmaceutically acceptable salt thereof, having the formula:

Formula III

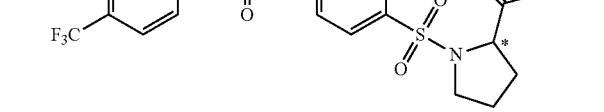

wherein

R1, R2, R3, R4, R5, R6, R7, R8 and R9 are independently H, —OH, alkyl, alkoxy, halogen, —NH2, —OCF3 or —CF3; and R10, R11 and R12 are independently H, —OH, halogen, alkoxy, —NH2, —CF3, —(CO)R13 where R13 is alkyl, alkoxy, amino, or alkylamino; —NR22R23, where R22 and R23 are independently H, alkyl; or R22 and R23 are optionally joined to form a 3-6 membered substituted or unsubstituted heterocycle having 1-3 heteroatoms.

Another aspect of the invention pertains to a compound of Formula IV, where R1, R2, R4, R5, R6, R7, R8, R9, R10 and R11 are H and R3 is CF3 or alkoxy:

Formula IV

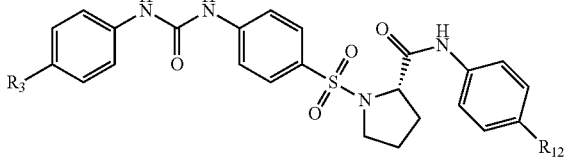

Another aspect of the invention pertains to a compound of Formula V, or a pharmaceutically acceptable salt thereof, having the formula:

Formula V

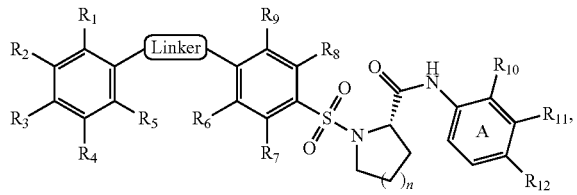

Another aspect of the invention pertains to a compound of Formula Ia, or a pharmaceutically acceptable salt thereof, having the formula:

Formula Ia

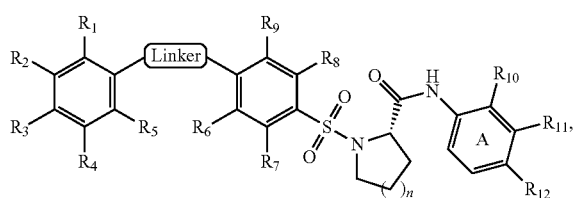

wherein

R1, R2, R3, R4, R5, R6, R7, R8 and R9 are independently H, —OH, alkyl, alkoxy, halogen, —NH2, —OCF3 or —CF3;

R10, R11 and R12 are independently H, —OH, halogen, alkoxy, —NH2, —CF3, —(CO)R13, where R13 is alkyl, alkoxy, amino, or alkylamino; —NR22R23, where R22 and R23 are independently H, alkyl; or R22 and R23 are optionally joined to form a 3-6 membered substituted or unsubstituted heterocycle having 1-3 heteroatoms;

Linker is —NH(CO)NR24-, wherein R24 is C1-C6 alkyl;

n is 0-3; and

Ring A is chosen from 5-6 membered aromatic rings containing 0-3 nitrogen atoms.

Another aspect of the invention pertains to a compound of Formula Ib, or a pharmaceutically acceptable salt thereof, having the formula:

Formula Ib wherein

R1, R2, R3, R4, R5, R6, R7, R8 and R9 are independently H, —OH, alkyl, alkoxy, halogen, —NH2, —OCF3 or —CF3;

R10, R11 and R12 are independently H, —OH, halogen, alkoxy, —NH2, —CF3, —(CO)R13, where R13 is alkyl, alkoxy, amino, or alkylamino; —NR22R23 where R22 and R23 are independently H, alkyl; or R22 and R23 are optionally joined to form a 3-6 membered substituted or unsubstituted heterocycle having 1-3 heteroatoms;

Linker is —NH(CO)NH—;

n is 0-3; and

Ring A is chosen from 5-6 membered aromatic rings containing 0-3 nitrogen atoms.

Another aspect of the invention pertains to a method comprising contacting one or more cells with:

a compound of Formula I, or a pharmaceutically acceptable salt thereof, having the formula:

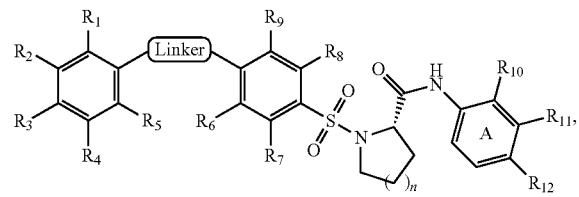

Formula I wherein

R1, R2, R3, R4, R5, R6, R7, R8 and R9 are independently H, —OH, alkyl, alkoxy, halogen, —NH2, —OCF3 or —CF3;

R10, R11 and R12 are independently H, —OH, halogen, alkoxy, —NH2, —CF3, —(CO)R13, where R13 is alkyl, alkoxy, amino, or alkylamino; —NR22R23, where R22 and R23 are independently H, alkyl; or R22 and R23 are optionally joined to form a 3-6 membered substituted or unsubstituted heterocycle having 1-3 heteroatoms;

Linker is —(CO)NR25-, NR26 or —R27(CO)—, wherein R25, R26 and R27 are independently H or C1-C6 alkyl;

n is 0-3; and

Ring A is chosen from 5-6 membered aromatic rings containing 0-3 nitrogen atoms.

Another aspect of the invention pertains to a method comprising contacting one or more cells with:

a compound of Formula II, or a pharmaceutically acceptable salt thereof, having the formula:

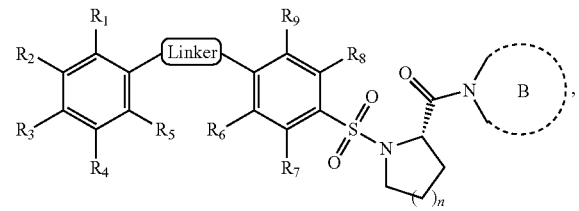

Formula II wherein

R1, R2, R3, R4, R5, R6, R7, R8 and R9 are independently H, —OH, alkyl, alkoxy, halogen, —NH2, —OCF3 or —CF3;

Ring B is chosen from substituted or unsubstituted C4-C7 aliphatic rings;

Linker is —NHCONR24-, —CONR25-, NR26 or —R27CO—, where R24, R25, R26 and R27 are independently H or C1-C6 alkyl; and n is 0-3.

Another aspect of the invention pertains to a method comprising contacting one or more cells with:

a compound, or a pharmaceutically acceptable salt thereof, having the formula:

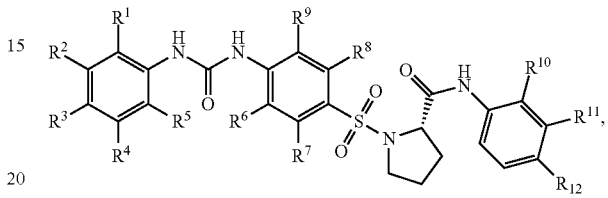

Formula III wherein

R1, R2, R3, R4, R5, R6, R7, R8 and R9 are independently H, —OH, alkyl, alkoxy, halogen, —NH2, —OCF3 or —CF3; and R10, R11 and R12 are independently H, —OH, halogen, alkoxy, —NH2, —CF3, —(CO)R13 where R13 is alkyl, alkoxy, amino, or alkylamino; —NR22R23, where R22 and R23 are independently H, alkyl; or R22 and R23 are optionally joined to form a 3-6 membered substituted or unsubstituted heterocycle having 1-3 heteroatoms.

Another aspect of the invention pertains to a method comprising contacting one or more cells with:

a compound of Formula IV, where R1, R2, R4, R5, R6, R7, R8, R9, R10 and R11 are H:

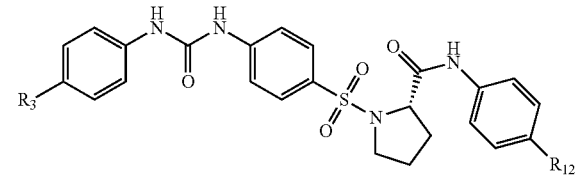

Formula IV

Another aspect of the invention pertains to a method comprising contacting one or more cells with one or more of the following compounds:

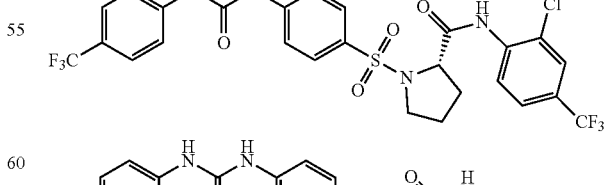

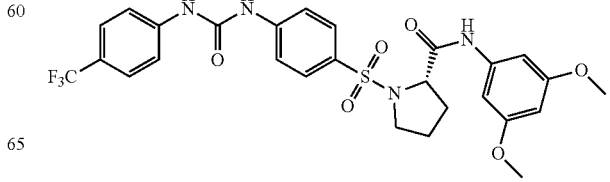

-continued

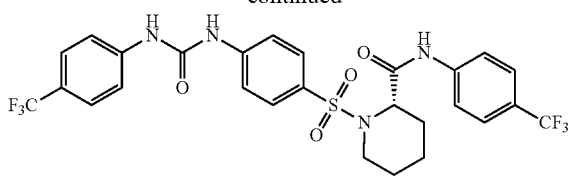

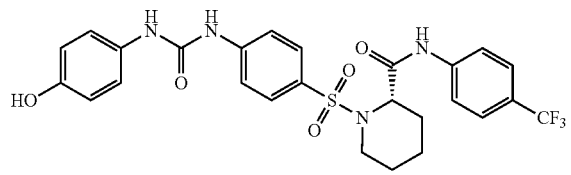

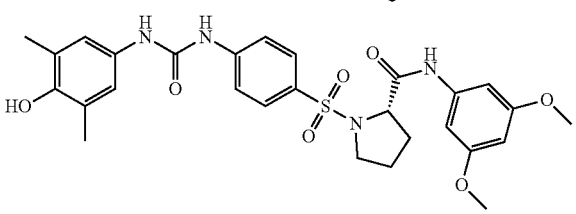

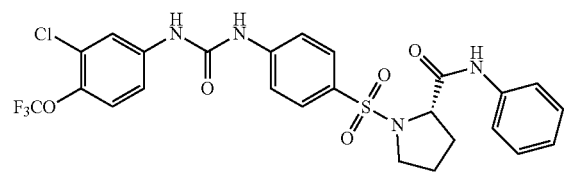

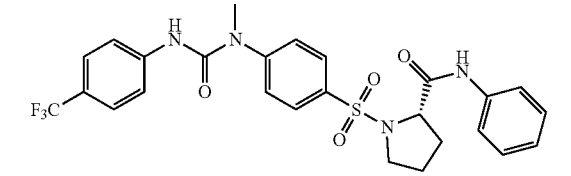

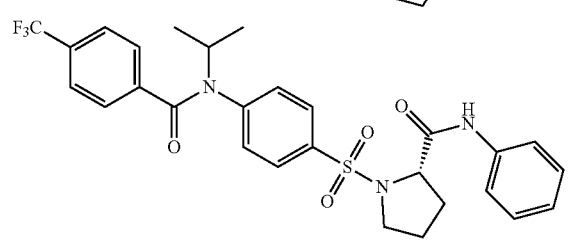

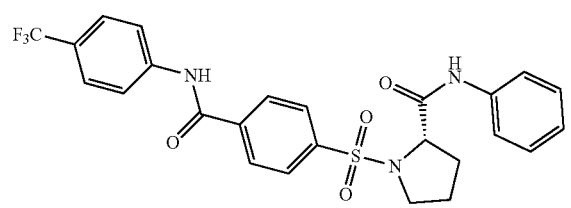

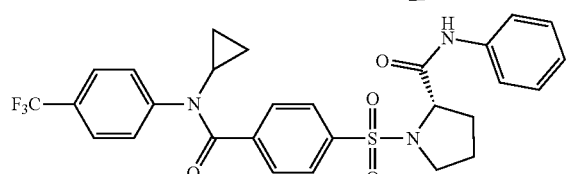

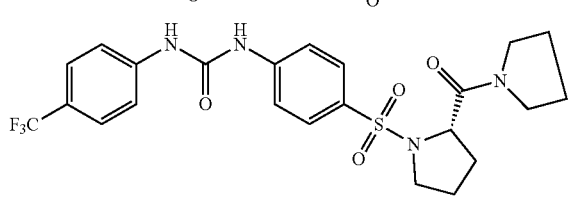

-continued

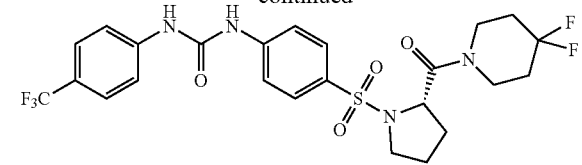

A further aspect of the invention pertains to a method comprising contacting one or more cells with a compound of Formula V, or a pharmaceutically acceptable salt thereof:

Formula V

Another aspect of the invention pertains to a method comprising contacting one or more cells with ZL0580, or a pharmaceutically acceptable salt thereof.

ZL0580

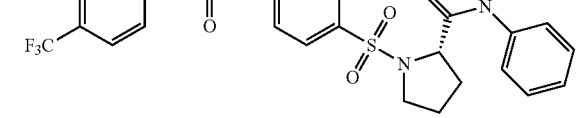

In some embodiments, the invention pertains to a method of suppressing HIV comprising, said method contacting one or more cells with ZL0580 or a pharmaceutically acceptable salt thereof.

In some embodiments, the invention pertains to a method of suppressing HIV transcription, said method comprising contacting one or more cells with ZL0580 or a pharmaceutically acceptable salt thereof.

In some embodiments, the invention pertains to a method of suppressing HIV activation by selectively targeting BRD4, said method comprising contacting one or more cells with ZL0580 or a pharmaceutically acceptable salt thereof.

In further embodiments, the invention pertains to a method of inhibiting Tat transactivation, said method comprising contacting one or more cells with ZL0580 or a pharmaceutically acceptable salt thereof.

In some embodiments, the invention pertains to a method of suppressing HIV comprising, said method contacting one or more cells with one or more compounds of Formulas I, II, III, IV, V, Va', Va", Vb, Vb', Vb", Ia, and Ib disclosed herein, or a pharmaceutically acceptable salt thereof.

In some embodiments, the invention pertains to a method of suppressing HIV transcription, said method comprising contacting one or more cells with one or more compounds of Formulas I, II, III, IV, V, Va', Va", Vb, Vb', Vb", Ia, or Ib disclosed herein, or a pharmaceutically acceptable salt thereof.

In some embodiments, the invention pertains to a method of suppressing HIV activation by selectively targeting BRD4, said method comprising contacting one or more cells with one or more compounds of Formulas I, II, III, IV, V, Va', Va", Vb, Vb', Vb", Ia, or Ib disclosed herein, or a pharmaceutically acceptable salt thereof.

In some embodiments, the invention pertains to a method of inhibiting Tat transactivation, said method comprising contacting one or more cells with one or more compounds of Formulas I, II, III, IV, V, Va', Va", Vb, Vb', Vb", Ia, or Ib disclosed herein, or a pharmaceutically acceptable salt thereof.

In further embodiments, the invention encompasses a method comprising contacting one or more cells with one or more compounds of Formulas I, II, III, IV, Ia, or Ib, or a pharmaceutically acceptable salt thereof.

J-Lat cells among different treatments (I) are shown. In this figure, error bars show SD of experimental replicates in (D and I) and of PCR duplicate in (E-F). Experiments were repeated at least 3 times. ** p<0.005, n.s.: non-significant by paired student t-test (Panel D-F, I).

FIG. 6. ZL0580 inhibits Tat transactivation and of key factors in HIV transcription elongation. (A-B) WB measurement of Tat and NF-kB (A) and cellular proteins involved in transcription elongation (B) in WT J-Lat cells 24 hours after treatments. (C) Co-IP analysis for binding of CDK9 to Tat or BRD4 in WT J-Lat cells 24 hours after treatments. Control IgG Co-IP and input CDK9 were shown as controls. Total/input CDK9 blot in panel (B and C) represents the same experiment. (D) ELL2 protein expression in WT and BRD4-KO J-Lat cells 24 hours after treatments. (E) ELL2 mRNA expression by Q-PCR in WT J-Lat cells 24 hours after treatments. (F) Effect of protease inhibition by MG132 on ELL2 protein level in WT J-Lat cells. Cells were pre-treated with proteasome inhibitor MG-132 for 6 hours (bottom) or not (top), followed by treatment with PMA or PMA+ZL0580 (10 µM) for 18 hours. ELL2 protein was measured by WB. (G) Phosphorylated RNAPII (Ser 2 CTD) in WT (top) and BRD4-KO (bottom) J-Lat cells after different treatments. Loading control GAPDH in panel (D and G) represents the same experiment. (H-I) CHIP-qPCR analysis for recruitment of Tat (H) or BRD4 (I) to HIV 5'-LTR in PMA-activated or un-stimulated J-Lat cells 24 hours after treatments. CHIP using control IgG was included for normalization. q-PCR was conducted to quantify the precipitated HIV 5'-LTR region. Data were normalized to NC. Error bars (E and H-I) show SD of qPCR replicate. All experiments were independently conducted at least three times. *p<0.05; **p<0.005 by one-way ANOVA (Panel H-I). N.D.: non-detectable.

Figure 7A:
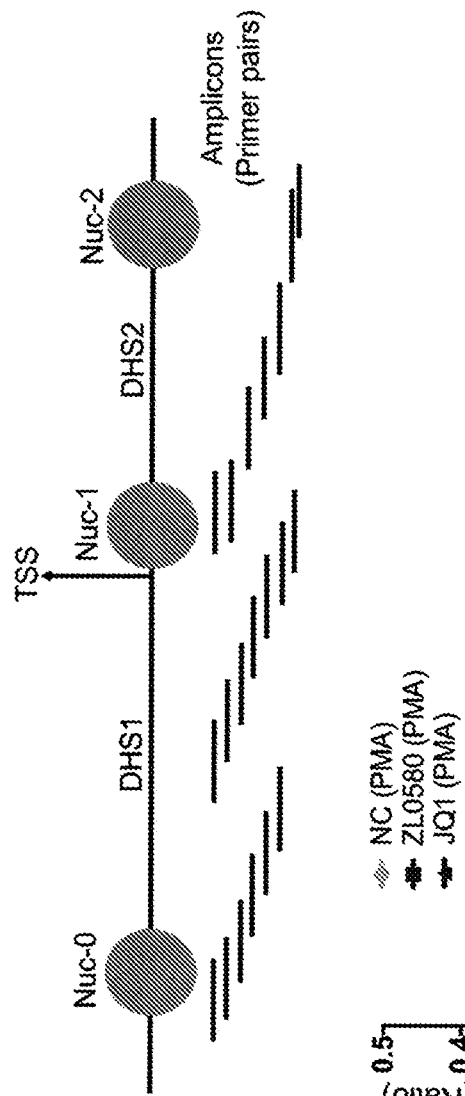

FIG. 7. Analysis of chromatin structure in HIV LTR by high-resolution MNase nucleosomal mapping. (A) Schematic diagram illustrating PCR amplicons at the HIV LTR covering 40-902 nucleotides that correspond to Nuc-0, DNase hypersensitive site 1 (DHS1), Nuc-1, DHS2, and Nuc-2. PCR product sizes are 100±10 bp with ~30 bp apart from each other. (B) Profile of chromatin structure in the HIV LTR in J-Lat cells after different treatments. Cells were either untreated (NC), or treated with ZL0580 (10 µM) or JQ1 (10 µM) for 24 hours, followed by activation with PMA for 24 hours. Chromatin profile was determined by calculating the ratio (Y axis) for the amount of PCR product in the MNase digested DNA to that of the undigested control DNA for each primer pair. X-axis shows corresponding PCR amplicon with base pair units with 0 as the start of LTR Nuc-0. The MNase assay was independently repeated twice. Error bars show SD of PCR replicates. *** (p<0.001) denotes statistical comparison among NC, ZL0580 and JQ1 by one-way ANOVA.

Figure 8:
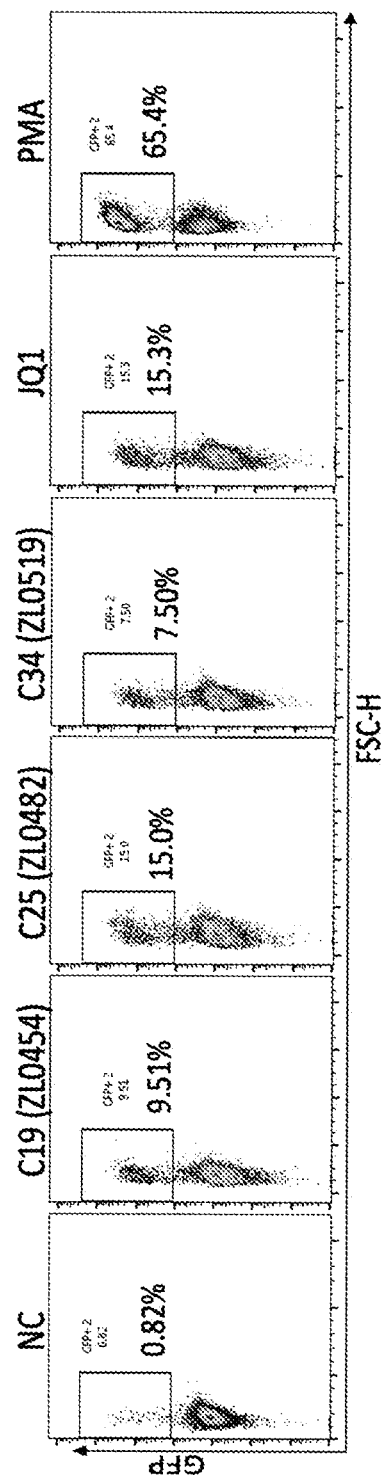

FIG. 8. Ability of compounds to activate latent HIV in J-Lat cells. J-Lat cells were treated with individual compounds (C1-C62) (10 µM) for 24 hours. Cells treated with DMSO (NC), JQ1 (10 µM) or PMA (100 ng/ml) were included as controls. HIV activation was expressed as % GFP+ in J-Lat cells, which was measured by flow cytometry. Among the 62 compounds, we identified that only C19 (ZL0454), C25 (ZL0482) and C34 (ZL0519) modestly activated HIV in this model. Results of these three compounds, together with NC, JQ1 and PMA, for activation of GFP expression were shown.

FIG. 9. qPCR raw Cq values for HIV 3'-LTR and cellular GAPDH RNAs in unstimulated/resting J-Lat cells. J-Lat cells were treated with NC, ZL0580 and JQ1 as described in FIG. 1G of main text. qPCR for HIV 3'-LTR and cellular GAPDH RNAs was performed on Day 2, 7 and Day 14 following treatment. The raw data indicates that basal HIV transcription can be readily and reliably detectable in un-stimulated J-Lat cells.

Figure 10A:
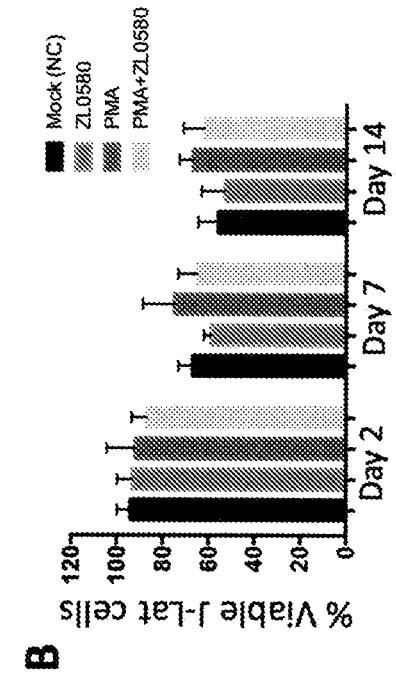
Figure 10B:
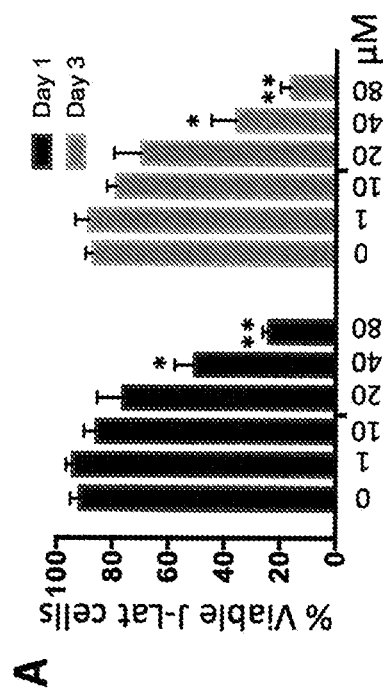

FIG. 10. J-Lat cell viability after ZL0580 treatments. (A) Viability of PMA-activated J-Lat cells after treatment with various concentrations of ZL0580 (0-80 µM). Cells were stimulated with PMA and treated with ZL0580 at indicated concentrations. Day 1 and Day 3 after treatments, cells viability was measured by flow cytometry based on Aqua blue staining. (B) Viability of un-stimulated and PMA-activated J-Lat cells after ZL0580 treatment (10 µM). Cells were mock treated (NC), or treated with ZL0580 alone (10 µM), PMA alone, or PMA+ZL0580 (10 µM). Cell viability was measured on Day 2, Day 7 and Day 14 after treatments. * p<0.05; ** p<0.005 (comparison with 0 µM).

FIG. 11. Specificity of ZL0580 in suppressing HIV in J-Lat: a preliminary structure-activity relationship. (A) Structure of JQ1 and its synergistic effect on enhancing PMA-stimulated HIV activation were shown as control. (B) In addition to ZL0580, another two compounds (ZL0506 & ZL0549) were identified to suppress HIV but at weaker levels. (C) Three other compounds in this library (ZL0482, ZL0454, & ZL0519) manifest an effect similar to JQ1 and enhance PMA-induced HIV activation. The chemical structures of these compounds and their regulatory effects on PMA-stimulated HIV activation were shown in (B & C).

Figure 12C:
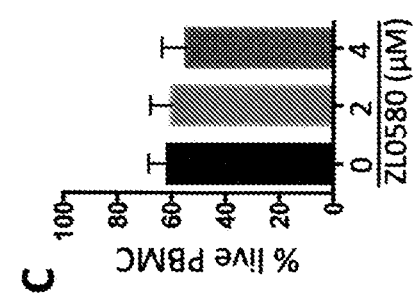

FIG. 12. Cellular toxicity of ZL0580 on activated or resting human PBMCs. (A-B) PBMCs (n=3) were activated with PHA for 2 days and treated with low-range (0-8 µM) (A) or high-range (0-80 µM) concentrations of ZL0580. JQ (10 µM) treatment was included as a control (B). 3 days after treatment, cells were stained with aqua blue and cell viability was measured by flow cytometry. (C) Cell viability of resting PBMCs (n=3) that were presented in FIG. 2E-F. Resting PBMCs (infected with HIV for 24 hours) were treated with ZL0580 (0, 2, 4 µM). Cell viability was measured by flow cytometry as described above on Day 6 after treatment (on the day when intracellular p24 was examined by FACS in FIG. 2E-F). * p<0.05; ** p<0.005.

Figure 13E:
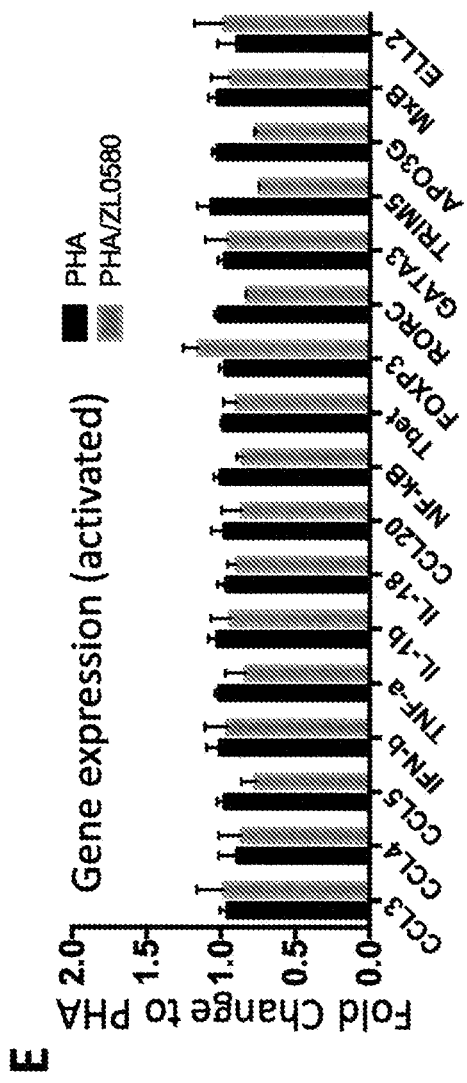
Figure 13F:
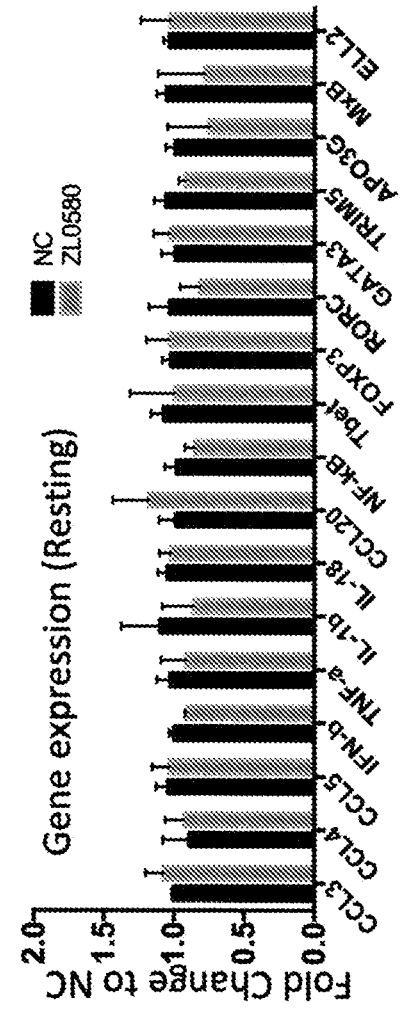

FIG. 13. Effects of ZL0580 on T cell phenotypes and gene expression of PBMCs. (A-C) Normal human PBMCs (n=3) were activated with PHA for 2 days and treated with ZL0580 (8 µM) (PHA/ZL0580) or not (PHA alone) for 3 days (as described in FIG. 2A). Surface expression of CD4 (A), CCR5 (B), and activation markers (CD25, CD38 and HLA-DR) (C) on activated T cells were examined by flow cytometry and compared between PHA and PHA/ZL0580. (D) Effect of ZL0580 on T-cell activation markers in un-stimulated PBMCs. PBMCs (n=3) (without PHA activation) were treated with ZL0580 (8 µM) or not (NC) for 3 days. Expression of activation markers (CD25, CD38 and HLA-DR) on T cells was measured and compared between NC and ZL0580. Error bars represent standard deviations of the 3 PBMC donors. (E-F) Impact of ZL0580 treatment on gene-expression profile in PHA-activated (E) or resting (F) PBMCs. PHA-activated or un-stimulated human PBMCs (n=2) were treated with ZL0580 (8 µM) or NC as described above. Two days after treatment, cellular RNAs were extracted and the expression of a wide range of genes associated with T-cell phenotype, lineage, differentiation and functions were measured by quantitative PCR. The data were compared between PHA and PHA/ZL0580 for activated PBMCs (E) or between NC and ZL0580 for un-stimulated PBMCs (F). Error bars represent standard deviations of PCR replicate. n.s. non-significant.

Figure 14:
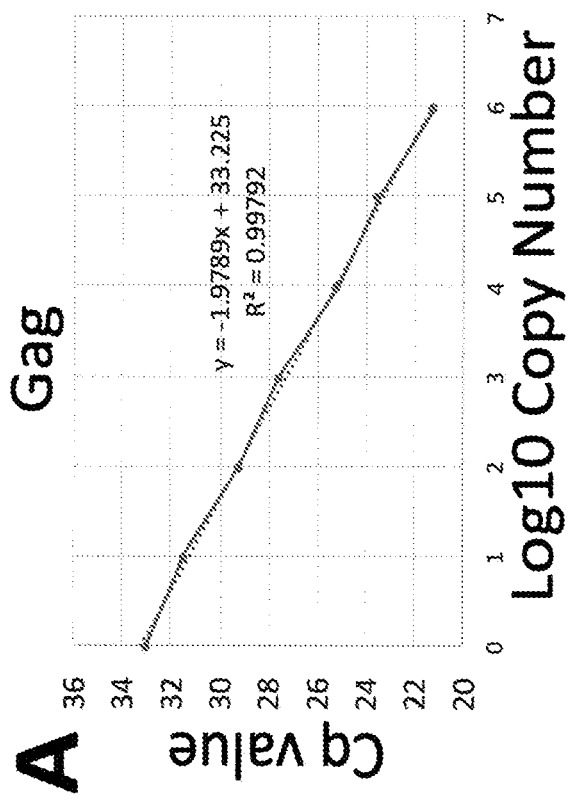

FIG. 14. Generation of standard curve for quantification of HIV RNA copies by nested PCR. To generate Gag-expressing plasmid, HIV RNA was extracted from the virus and cDNA was synthesized. Gag gene was amplified, gel purified and cloned into pGEM®-T Easy Vector Systems. The standard plasmid was 10 times diluted from $10^6\sim10^0$ and subjected to the first round PCR of 16 cycles of amplification with the primers Gag-out-F/R (Table S5), followed by the second round ultra-sensitive nested PCR for 40 cycles using the primers Gag-F/R (Table S5). The standard curve was generated according to the Cq values of the nested real-time PCR.

Figure 15:
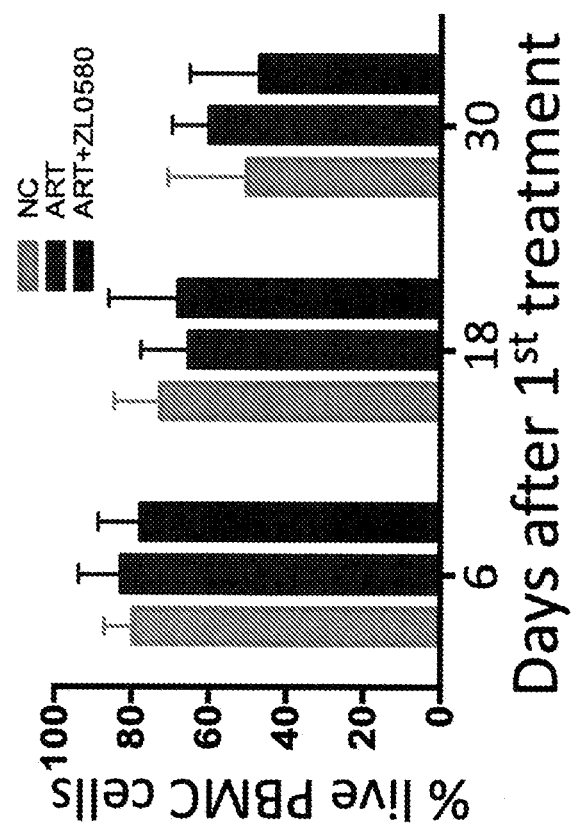

FIG. 15. Cell viability of RV254 PBMCs at various days after treatments. PBMC cell viability was determined based on Aqua Blue staining and flow cytometric analysis as described earlier.

Figure 16A:
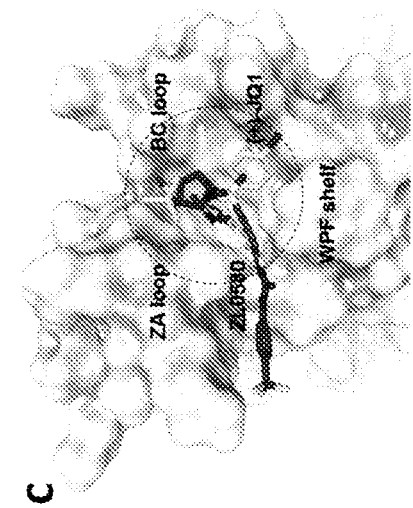
Figure 16B:
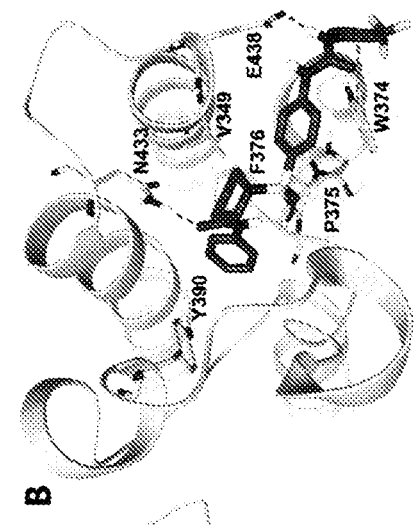
Figure 16C:
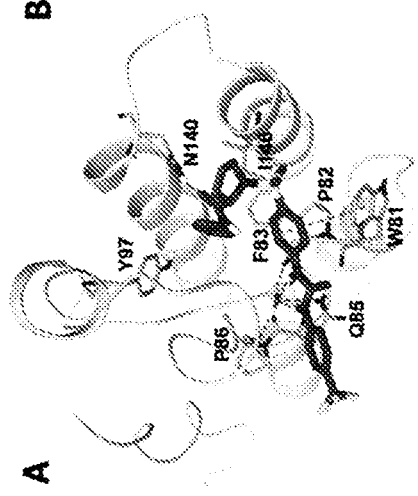

FIG. 16. Docking analysis of ZL0580 binding to BD1 and BD2 domains of BRD4. (A) Docking pose of ZL0580 with BRD4 (BD1) (PDB code: 3MXF) in ribbon representation. ZL0580 is shown in magenta sticks, key residues of N140, Y97, I146, W81, P82, F83, Q85 and P86 in gray sticks and conserved water in red sticks. H-bond is shown in purple dotted lines and π stacking in blue dotted line. demonstrates ZL0580 can well access the conserved KAc binding pocket of BRD4 (BD1). The amide ketone of ZL0580 forms H-bond with the critical conserved residue Asn140. One terminal phenyl ring interacts with Y97 of ZA loop, and the proline fragment interacts with the gatekeeper I146 through hydrophobic interaction. Both of NH on the urea linker interact with Q85 and P86 with water-mediated H-bonds. The middle phenyl ring forms a π stacking with W81. The phenyl urea sulfonamide fragment extends to the region between WPF shelf and ZA channel, suggesting ZL0580 is further stabilized by hydrophobic interactions with this region of binding site. (B) Docking pose of ZL0580 with BRD4(BD2) (PDB code: 4Z93) in ribbon representation. ZL0580 is shown in magenta sticks, key residues of N433, Y390, V349, W374, P375, F376, and E438 in gray sticks. H-bond is shown in purple dotted lines and π stacking in blue dotted line. It shows ZL0580 can access the conserved KAc binding pocket of BRD4 (BD2) in a pose substantially different from that binds at BRD4(BD1). ZL0580 can still form a H-bond with the conserved residue Asn433 (Asn 140 in BRD4(BD1)). However, one NH on the urea linker forms a H-bond with E438, making the phenylurea sulfonamide fragment swinging to the other side of WPF shelf and shifted away from ZA loop, resulting in less interaction with the conserved Y390 (Y97 in BRD4(BD1)) of ZA loop and hydrophobic residues of WPF shelf overall. Such difference on the binding poses may lead to the selectivity of ZL0580 towards BRD4(BD1). (C) Surface representation of ZL0580 (magenta) docked pose superimposed with BRD4 (BD1)/(+)-JQ1 complex structure and overlay analysis comparison (PDB code: 3MXF). It depicts ZL0580 can well access into the KAc binding pocket of BRD4(BD1) with partial scaffold extending to an additional region. The proline sulfonamide fragment of ZL0580 can overlap nicely with the crystallographically determined JQ1 binding mode (circled area), while the phenylurea sulfonamide moiety extends to the region between WPF shelf and ZA channel, which further stabilizes ligand-target interactions.

Figure 17:
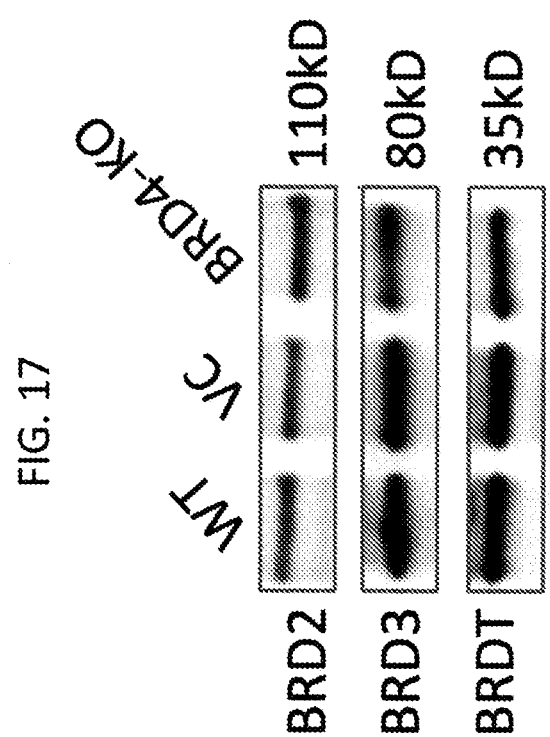

FIG. 17. Expression of other BET proteins in BRD4-KO J-Lat cells. Expression of other BET proteins (BRD2, BRD3, BRDT) in WT, VC and BRD4-KO J-Lat cells was measured by WB. Protein sizes are indicated.

Figure 18:
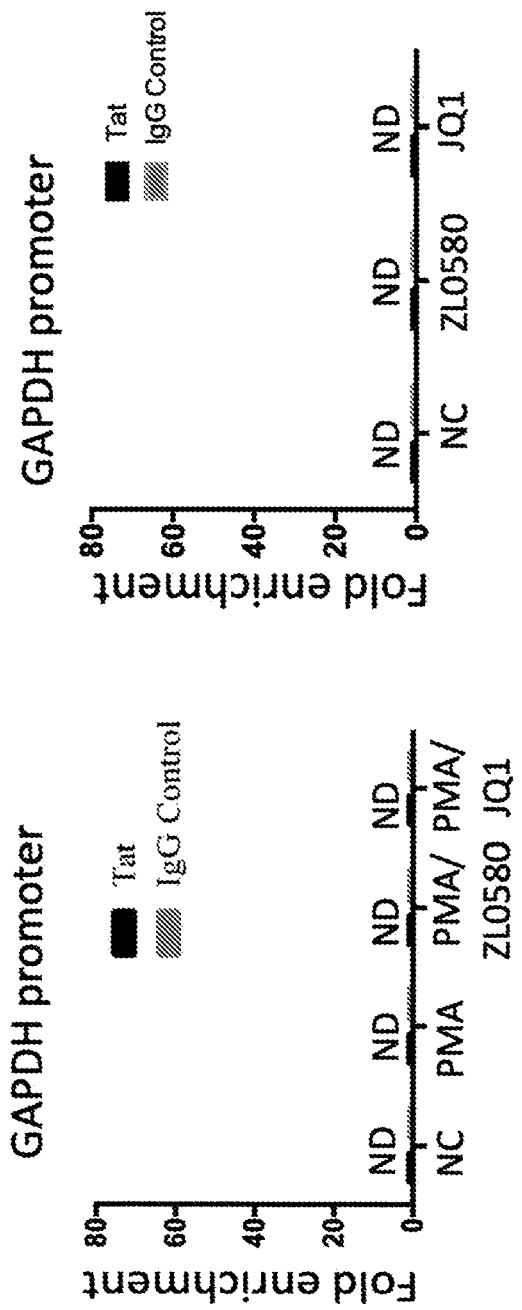

FIG. 18. CHIP-qPCR analysis for binding of Tat to GAPDH promoter region. PMA-activated (left) or resting (right) J-Lat cells were treated as indicated. 24 hours after treatment, cells were subjected to CHIP-qPCR analysis using Tat or control IgG antibody to detect the specific binding Tat to GAPDH promoter region. Data were normalized to control IgG as well as to NC and expressed as fold enrichment. ND represents "non-detectable".

DETAILED DESCRIPTION

1.0. Definitions

For the purposes of promoting an understanding of the principles of the invention, reference will now be made to certain embodiments and specific language will be used to describe the same. It will nevertheless be understood that no limitation of the scope of the invention is thereby intended, and alterations and modifications in the illustrated invention, and further applications of the principles of the invention as illustrated therein are herein contemplated as would normally occur to one skilled in the art to which the invention relates.

Unless defined otherwise, all technical and scientific terms used herein have the same meaning as commonly understood by one of ordinary skill in the art to which this invention pertains.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used).

The use of "or" means "and/or" unless stated otherwise.

The use of "a" or "an" herein means "one or more" unless stated otherwise or where the use of "one or more" is clearly inappropriate.

The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "about" refers to a ±10% variation from the nominal value. It is to be understood that such a variation is always included in any given value provided herein, whether or not it is specifically referred to.

As used herein, the terms "cell" and "cells" refer to any types of cells from any animal, such as, without limitation, rat, mice, monkey, and human.

The term "alkyl" as used herein by itself or as part of another group refers to both straight and branched chain radicals, and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The term "alkyl" may include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, and dodecyl.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O, and N. The heteroatom(s) may be placed at any interior position of the heteroalkyl group or at the position at which the alkyl group is attached to the remainder of the molecule. Up to two heteroatoms may be consecutive.

The term "alkylene" as used herein refers to straight and branched chain alkyl linking groups, i.e., an alkyl group that links one group to another group in a molecule. In some embodiments, the term "alkylene" may include —$(CH_2)_n$— where n is 2-8.

The term "aryl" means a polyunsaturated hydrocarbon substituent. Aryl groups can be monocyclic or polycyclic (e.g., 2 to 3 rings that are fused together or linked covalently). Non-limiting examples of aryl and heteroaryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

The term "heteroaryl" as used herein refers to groups having 5 to 14 ring atoms; 6, 10 or 14 7π-electrons shared in a cyclic array; and containing carbon atoms and 1, 2 or 3 oxygen, nitrogen or sulfur heteroatoms. A heteroaryl group can be attached to the remainder of the molecule through a carbon or heteroatom. Especially preferred heteroaryl groups include 1,2,3-triazole, 1,2,4-triazole, 5-amino 1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, 2-aminopyridine, 4-aminopyridine, 2-aminoimidazoline, and 4-aminoimidazoline.

An "amino" group refers to an —$NH_2$ group.

A "carboxylic acid" group refers to a $CO_2H$ group.

An "alkynyl group" refers to a straight or branched chain radical of 2-20 carbon atoms, unless the chain length is limited thereto, wherein there is at least one triple bond between two of the carbon atoms in the chain, including, but not limited to, acetylene, 1-propylene, 2-propylene, and the like. In some embodiments, "alkynyl group" refers to an alkynyl chain, which is 2 to 10 carbon atoms in length. In other embodiments, "alkynyl group" refers to an alkynyl chain, which is more 2 to 8 carbon atoms in length. In further embodiments, "alkynyl group" refers to an alkynyl chain, which is from 2 to 4 carbon atoms in length.

An "amido" group refers to an —$CONH_2$ group. An alkylamido group refers to an —CONHR group wherein R is a straight chained, or branched alkyl. In some embodiments, R may be taken together with the —(C=O)— group to form a ring, which may be fused with, or bonded to, to a substituted or unsubstituted aryl, heteroaryl, or heterocyclic ring.

A dialkylamido group refers to an —CONRR' group wherein R and R' are may straight-chained, or branched, alkyl or may be taken together to form a ring, which may be fused with, or bonded to, to a substituted or unsubstituted aryl, heteroaryl, or heterocyclic ring.

The term "halogen" or "halo" or "halide" as used herein by itself or as part of another group refers to chlorine, bromine, fluorine or iodine.

The term "hydroxy" or "hydroxyl" as used herein by itself or as part of another group refers to an —OH group.

An "alkoxy" group refers to an —O-alkyl group wherein "alkyl" is as defined above. In one embodiment, the alkyl group has 1-12 carbons. In another embodiment, the alkyl group has 1-7 carbons. In a further embodiment, the alkyl group has 1-6 carbons. In another embodiment, the alkyl group has 1-4 carbons.

The term "heterocycle" or "heterocyclic ring", as used herein except where noted, represents a stable 5- to 7-membered monocyclic-, or stable 7- to 11-membered bicyclic heterocyclic ring system, any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Rings may contain one oxygen or sulfur, one to three nitrogen atoms, or one oxygen or sulfur combined with one or two nitrogen atoms. The heterocyclic ring may be attached at any heteroatom or carbon atom that results in the creation of a stable structure.

The term "alkylamino" as used herein by itself or as part of another group refers to an amino group which is substituted with one alkyl group having from 1 to 6 carbon atoms. The term "dialkylamino" as used herein by itself or as part of another group refers to an amino group which is substituted with two alkyl groups, each having from 1 to 6 carbon atoms.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, alkyl, heteroalkyl, alkoxy, alkylthio, alkylamino, (alkyl)$_2$amino, alkylsulfinyl, alkylsulfonyl, arylsulfonyl, substituted or unsubstituted cycloalkyl, substituted or unsubstituted heterocyclyl, substituted or unsubstituted aryl, and substituted or unsubstituted heteroaryl. In certain aspects, the optional substituents may be further substituted with one or more substituents independently selected from: halogen, nitro, cyano, hydroxy, amino, mercapto, formyl, carboxy, carbamoyl (—$C(O)NR_2$), unsubstituted alkyl, unsubstituted heteroalkyl, alkoxy, alkylthio, alkylamino, (alkyl)$_2$amino, alkylsulfinyl, alkyl sulfonyl, aryl sulfonyl, unsubstituted cycloalkyl, unsubstituted heterocyclyl, unsubstituted aryl, or unsubstituted heteroaryl. Exemplary optional substituents include, but are not limited to: —OH, oxo (=O), —Cl, —F, Br, $C_{1-4}$alkyl, phenyl, benzyl, —$NH_2$, —$NH(C_{1-4}alkyl)$, —$N(C1-4alkyl)_2$, —NO2, —$S(C_{1-4}alkyl)$, —$SO_2(C_{1-4}alkyl)$, —$CO_2(C_{1-4}alkyl)$, and —$O(C_{1-4}alkyl)$.

The term "pharmaceutically acceptable salt" refers to those salts of the compounds of the present invention which are, within the scope of sound medical judgment, suitable for use in contact with the tissues of patients without undue toxicity, and the like. As used herein, the term "pharmaceutically acceptable salt" may include acetate, hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. (See S. M. Barge et al., "Pharmaceutical Salts," J. Pharm. Sci., 66:1-19 (1977)), which is incorporated herein by reference in its entirety, for further examples of pharmaceutically acceptable salt).

The terms "treating," "treatment" and the like as used herein includes the management and care of a subject (preferably a mammal, more preferably a human) for the purpose of combating a disease, condition, or disorder and includes the administration of a compound of the present disclosure to prevent the onset of the symptoms or complications, alleviate the symptoms or complications, or eliminate the disease, condition, or disorder.

The term "subject" as used herein refers to an animal, preferably a mammal, most preferably a human, who has been the object of treatment, observation or experiment. Preferably, the subject has experienced and/or exhibited at least one symptom of the disease or disorder to be treated and/or prevented. Further, a subject may not have exhibited any symptoms of the disorder, disease or condition to be treated and/prevented, but has been deemed by a physician, clinician or other medical professional to be at risk for developing said disorder, disease or condition.

The symbol (*) is used herein to indicate the presence of a chiral carbon.

2.0. Compounds

The inventors surprisingly discovered that certain novel small molecules BRD4 modulators.

The present invention encompasses the following embodiments:

1. A compound, or a pharmaceutically acceptable salt thereof, having the formula:

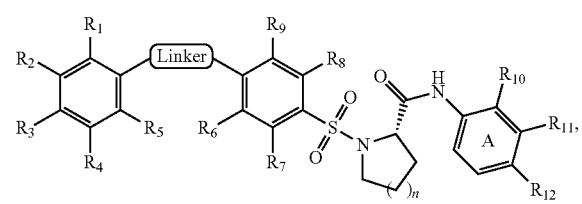

Formula I wherein

R1, R2, R3, R4, R5, R6, R7, R8 and R9 are independently H, —OH, alkyl, alkoxy, halogen, —NH2, —OCF3 or —CF3;

R10, R11 and R12 are independently H, —OH, halogen, alkoxy, —NH2, —CF3, —(CO)R13 where R13 is alkyl, alkoxy, amino, or alkylamino; —NR22R23 where R22 and R23 are independently H, alkyl; or R22 and R23 are optionally joined to form a 3-6 membered substituted or unsubstituted heterocycle having 1-3 heteroatoms.

Linker is —(CO)NR25-, NR26 or —R27(CO)—, wherein R25, R26 and R27 are independently H or C1-C6 alkyl.

n is 0-3.

Ring A is chosen from 5-6 membered aromatic rings containing 0-3 nitrogen atoms.

2. A compound, or a pharmaceutically acceptable salt thereof, having the formula:

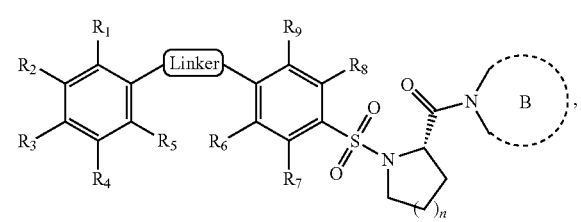

Formula II wherein

R1, R2, R3, R4, R5, R6, R7, R8 and R9 are independently H, —OH, alkyl, alkoxy, halogen, —NH2, —OCF3 or —CF3;

Ring B is chosen from substituted or unsubstituted C4-C7 aliphatic rings;

Linker is —NHCONR24-, —CONR25-, NR26 or —R27CO—. R24, R25, R26 and R27 are independently H or C1-C6 alkyl; and n is 0-3.

3. A compound, or a pharmaceutically acceptable salt thereof, having the formula:

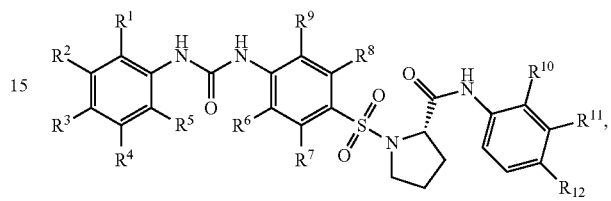

Formula III wherein

R1, R2, R3, R4, R5, R6, R7, R8 and R9 are independently H, —OH, alkyl, alkoxy, halogen, —NH2, —OCF3 or —CF3; and R10, R11 and R12 are independently H, —OH, halogen, alkoxy, —NH2, —CF3, —(CO)R13 where R13 is alkyl, alkoxy, amino, or alkylamino; —NR22R23, where R22 and R23 are independently H, alkyl; or R22 and R23 are optionally joined to form a 3-6 membered substituted or unsubstituted heterocycle having 1-3 heteroatoms.

4. A compound of embodiment 1, where R1, R2, R4, R5, R6, R7, R8, R9, R10 and R11 are H and R3 is CF3 or alkoxy:

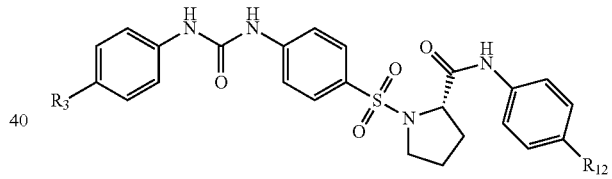

Formula IV

6. A compound of any of the preceding embodiments where the compound is:

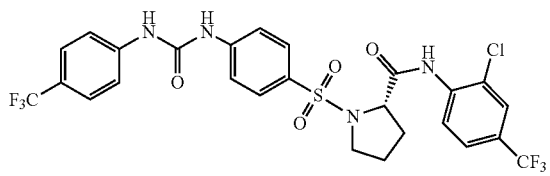

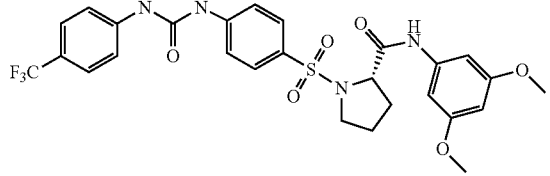

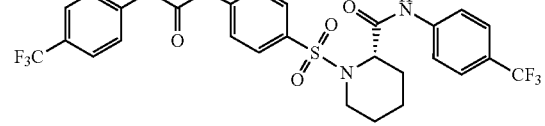

-continued

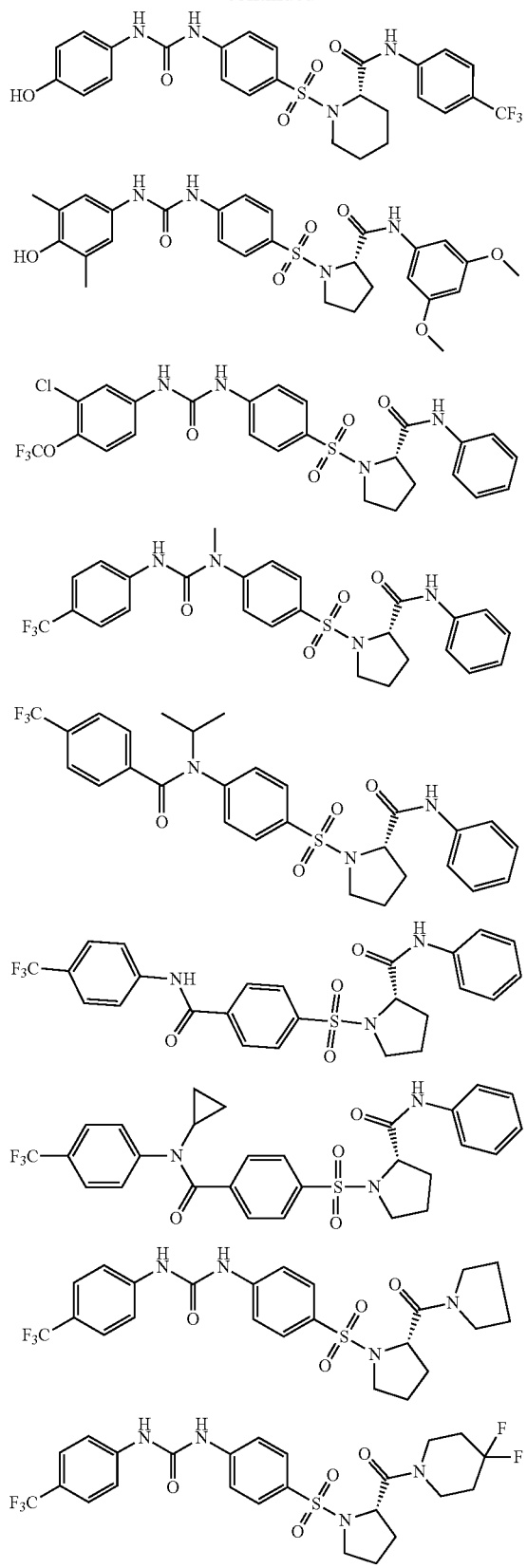

7. A compound, or a pharmaceutically acceptable salt thereof, having the formula:

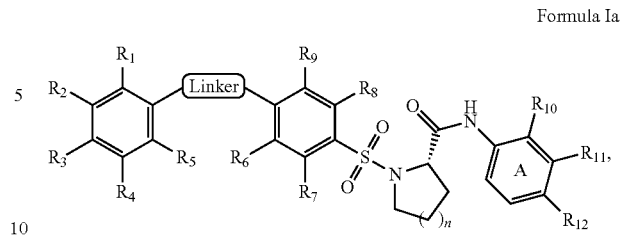

Formula Ia wherein
R1, R2, R3, R4, R5, R6, R7, R8 and R9 are independently H, —OH, alkyl, alkoxy, halogen, —NH2, —OCF3 or —CF3;
R10, R11 and R12 are independently H, —OH, halogen, alkoxy, —NH2, —CF3, —(CO)R13 where R13 is alkyl, alkoxy, amino, or alkylamino; —NR22R23 where R22 and R23 are independently H, alkyl; or R22 and R23 are optionally joined to form a 3-6 membered substituted or unsubstituted heterocycle having 1-3 heteroatoms;
Linker is —NH(CO)NR24-, wherein R24 is C1-C6 alkyl;
n is 0-3; and
Ring A is chosen from 5-6 membered aromatic rings containing 0-3 nitrogen atoms.

8. A compound, or a pharmaceutically acceptable salt thereof, having the formula:

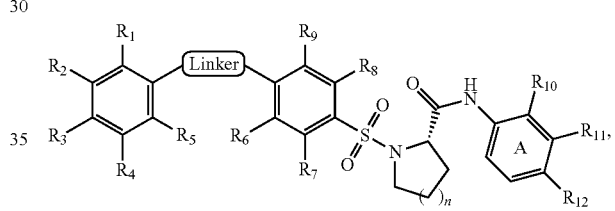

Formula Ib wherein
R1, R2, R3, R4, R5, R6, R7, R8 and R9 are independently H, —OH, alkyl, alkoxy, halogen, —NH2, —OCF3 or —CF3;
R10, R11 and R12 are independently H, —OH, halogen, alkoxy, —NH2, —CF3, —(CO)R13 where R13 is alkyl, alkoxy, amino, or alkylamino; —NR22R23 where R22 and R23 are independently H, alkyl; or R22 and R23 are optionally joined to form a 3-6 membered substituted or unsubstituted heterocycle having 1-3 heteroatoms;
Linker is —NH(CO)NH—;
n is 0-3; and
Ring A is chosen from 5-6 membered aromatic rings containing 0-3 nitrogen atoms.

9. A compound of Formula V, or a pharmaceutically acceptable salt thereof, having the formula:

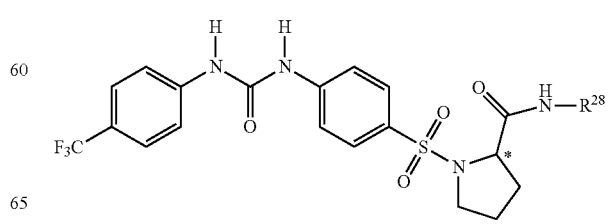

Formula V wherein $R^{28}$ is substituted or unsubstituted aryl.

In one aspect of the invention, Formula V is a racemic mixture. Furthermore, Formula V maybe a racemate. In some embodiments, Formula V is a (R)- or (S)-enantiomer, or a combination thereof.

10. A compound of Formula Va', or a pharmaceutically acceptable salt thereof, having the formula:

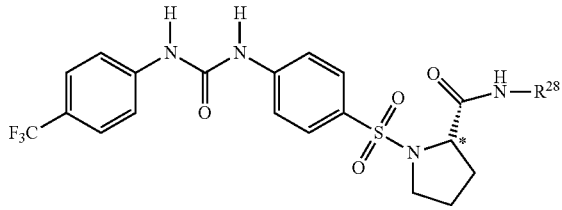

Formula Va' wherein R²⁸ is substituted or unsubstituted aryl.

11. A compound of Formula Va", or a pharmaceutically acceptable salt thereof, having the formula:

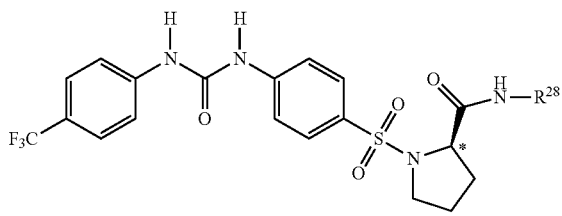

Formula Va"

12. A compound of Formula Vb, or a pharmaceutically acceptable salt thereof, having the formula:

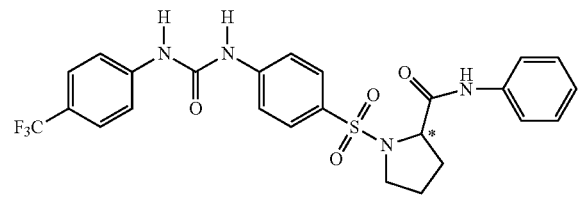

Formula Vb

13. A compound of Formula Vb', or a pharmaceutically acceptable salt thereof, having the formula:

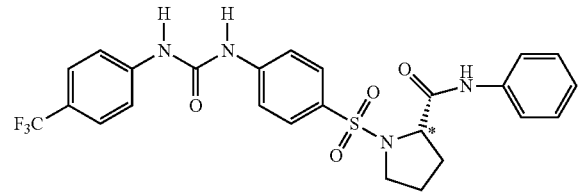

Formula Vb'

14. A compound of Formula Vb", or a pharmaceutically acceptable salt thereof, having the formula:

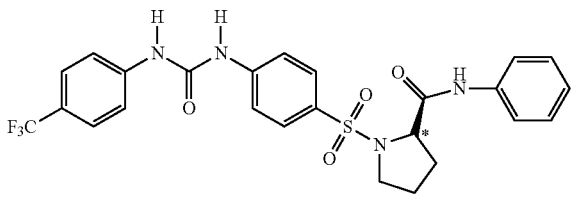

Formula Vb"

3.0. Method of Use

The inventors have surprisingly discovered that certain novel small molecules that may be used as BRD4 modulators. In certain aspects of the invention any of the compounds of Formulas I, II, III, IV, V, Va', Va", Vb, Vb', Vb", Ia, and Ib, or a pharmaceutically acceptable salt thereof, may be contacted with one or more cells to at least, for example, to suppress HIV; suppress HIV transcription, suppress HIV activation, inhibit Tat transactivation, suppressing HIV activation by selectively targeting BRD4, suppress HIV in J-Lat cells, etc.

Formula I

A compound having the formula:

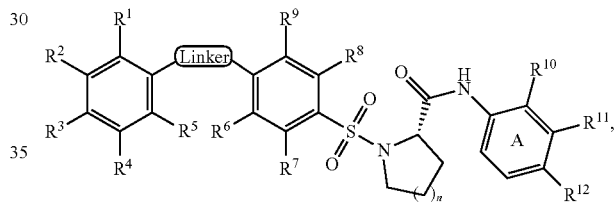

Formula I wherein

R1, R2, R3, R4, R5, R6, R7, R8 and R9 are independently H, —OH, alkyl, alkoxy, halogen, —NH2, —OCF3 or —CF3;

R10, R11 and R12 are independently H, —OH, halogen, alkoxy, —NH2, —CF3, —(CO)R13 where R13 is alkyl, alkoxy, amino, or alkylamino; —NR22R23, where R22 and R23 are independently H, alkyl; or R22 and R23 are optionally joined to form a 3-6 membered substituted or unsubstituted heterocycle having 1-3 heteroatoms;

Linker is —(CO)NR25-, NR26 or —R27(CO)—, wherein R25, R26 and R27 are independently H or C1-C6 alkyl;

n is 0-3; and

Ring A is chosen from 5-6 membered aromatic rings containing 0-3 nitrogen atoms.

Formula II

A compound of Formula II having the formula:

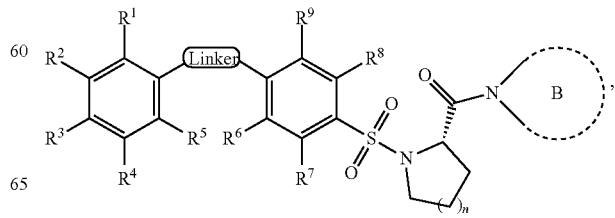

Formula II

23 wherein
R1, R2, R3, R4, R5, R6, R7, R8 and R9 are independently H, —OH, alkyl, alkoxy, halogen, —NH2, —OCF3 or —CF3;
Ring B is chosen from substituted or unsubstituted C4-C7 aliphatic rings;
Linker is —NHCONR24-, —CONR25-, NR26 or —R27CO—. R24, R25, R26 and R27 are independently H or C1-C6 alkyl; and
n is 0-3.

Formula III
A compound having the formula:

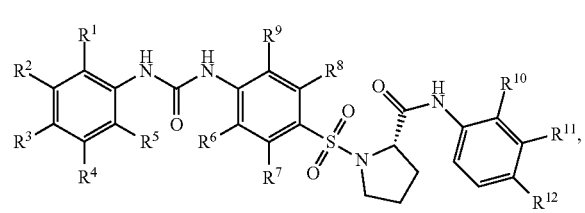

Formula III wherein
R1, R2, R3, R4, R5, R6, R7, R8 and R9 are independently H, —OH, alkyl, alkoxy, halogen, —NH2, —OCF3 or —CF3; and
R10, R11 and R12 are independently H, —OH, halogen, alkoxy, —NH2, —CF3, —(CO)R13 where R13 is alkyl, alkoxy, amino, or alkylamino; —NR22R23 where R22 and R23 are independently H, alkyl; or R22 and R23 are optionally joined to form a 3-6 membered substituted or unsubstituted heterocycle having 1-3 heteroatoms.

Formula IV
A compound of Formula IV, where R1, R2, R4, R5, R6, R7, R8, R9, R10 and R11 are H:

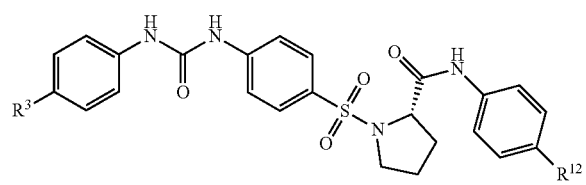

Formula IV

Formula Ia
A compound of Formula Ia having the formula:

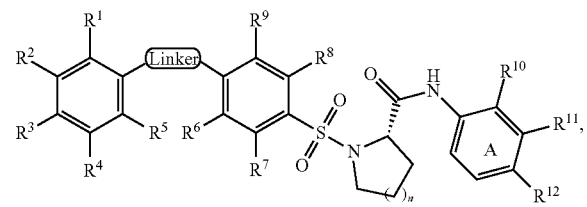

Formula Ia wherein
R1, R2, R3, R4, R5, R6, R7, R8 and R9 are independently H, —OH, alkyl, alkoxy, halogen, —NH2, —OCF3 or —CF3;
R10, R11 and R12 are independently H, —OH, halogen, alkoxy, —NH2, —CF3, —(CO)R13 where R13 is alkyl,

24 alkoxy, amino, or alkylamino; —NR22R23 where R22 and R23 are independently H, alkyl; or R22 and R23 are optionally joined to form a 3-6 membered substituted or unsubstituted heterocycle having 1-3 heteroatoms;
Linker is —NH(CO)NR24-, wherein R24 is C1-C6 alkyl;
n is 0-3; and
Ring A is chosen from 5-6 membered aromatic rings containing 0-3 nitrogen atoms.

Formula Ib
A compound of Formula Ib having the formula:

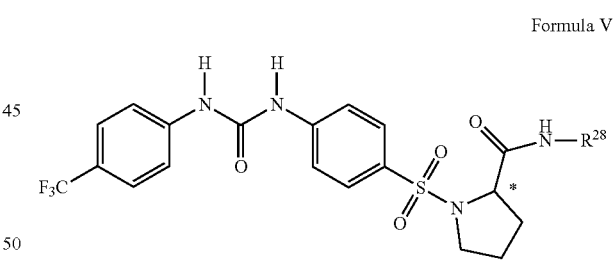

Formula Ib wherein
R1, R2, R3, R4, R5, R6, R7, R8 and R9 are independently H, —OH, alkyl, alkoxy, halogen, —NH2, —OCF3 or —CF3;
R10, R11 and R12 are independently H, —OH, halogen, alkoxy, —NH2, —CF3, —(CO)R13 where R13 is alkyl, alkoxy, amino, or alkylamino; —NR22R23 where R22 and R23 are independently H, alkyl; or R22 and R23 are optionally joined to form a 3-6 membered substituted or unsubstituted heterocycle having 1-3 heteroatoms;
Linker is —NH(CO)NH—;
n is 0-3; and
Ring A is chosen from 5-6 membered aromatic rings containing 0-3 nitrogen atoms.

Formula V
A compound of Formula V, or a pharmaceutically acceptable salt thereof, having the formula:

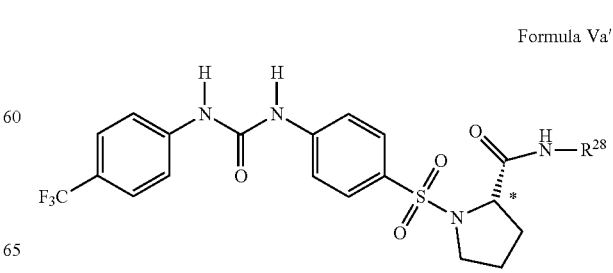

Formula V wherein $R^{28}$ is substituted or unsubstituted aryl.

A compound of Formula Va', or a pharmaceutically acceptable salt thereof, having the formula:

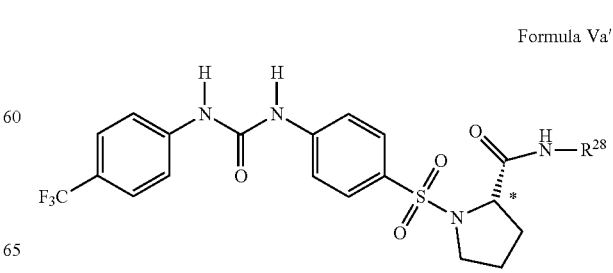

Formula Va' wherein $R^{28}$ is substituted or unsubstituted aryl.

A compound of Formula Va", or a pharmaceutically acceptable salt thereof, having the formula:

Formula Va"

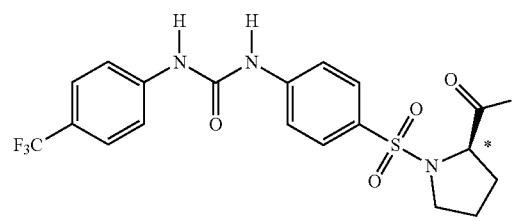

A compound of Formula Vb, or a pharmaceutically acceptable salt thereof, having the formula:

Formula Vb

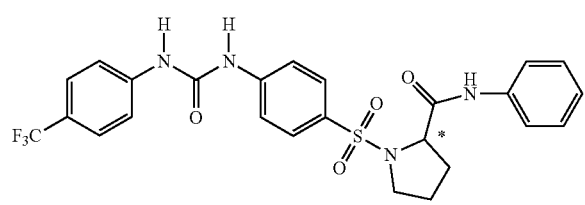

A compound of Formula Vb', or a pharmaceutically acceptable salt thereof, having the formula:

Formula Vb'

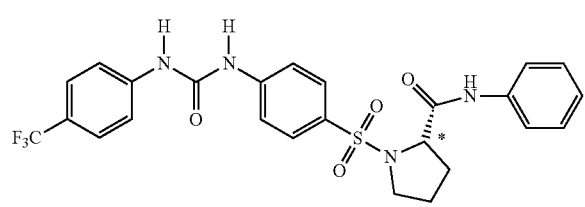

A compound of Formula Vb", or a pharmaceutically acceptable salt thereof, having the formula:

Formula Vb"

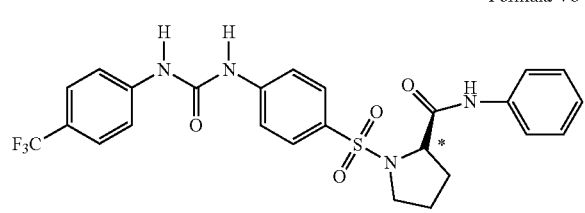

Another aspect of the invention pertains to a method comprising contacting one or more cells with one or more of the following compounds, or a pharmaceutically acceptable salt thereof, to, for example, suppress HIV transcription, suppress HIV activation, inhibit Tat transactivation, suppressing HIV activation by selectively targeting BRD4, suppress HIV in J-Lat cells, human peripheral blood mononuclear cells (PBMCs), and human CD4 T cells, etc.:

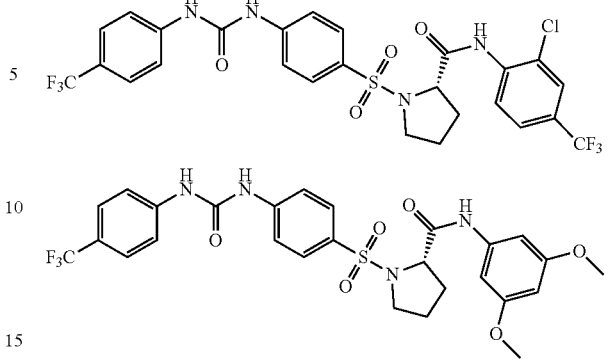

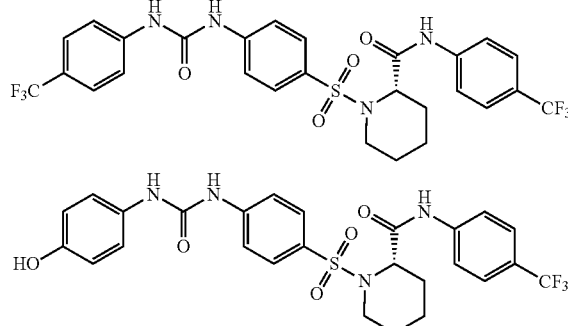

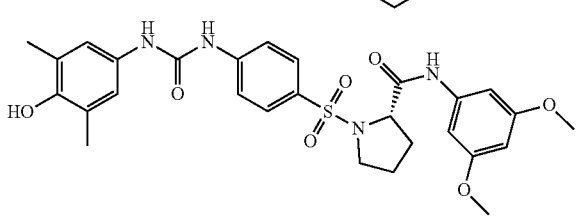

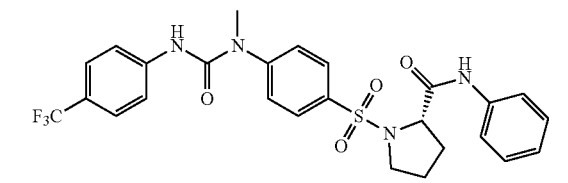

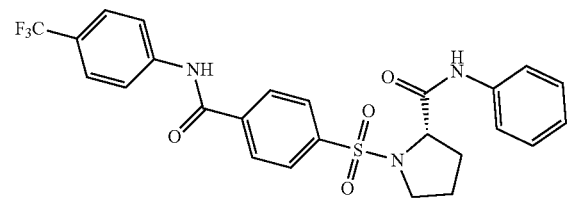

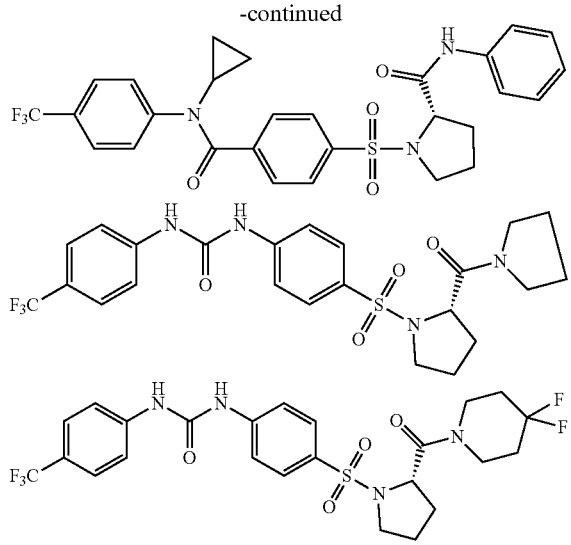

Another aspect of the invention pertains to a method comprising contacting one or more cells with one or more compounds of Formulas V, Va', Va", Vb, Vb', and Vb", or a pharmaceutically acceptable salt thereof; to, for example, suppress HIV transcription, suppress HIV activation, inhibit Tat transactivation, suppressing HIV activation by selectively targeting BRD4, suppress HIV in J-Lat cells, human peripheral blood mononuclear cells (PBMCs), and human CD4 T cells.

Another further of the invention pertains to a method comprising contacting one or more cells with ZL0580, or a pharmaceutically acceptable salt thereof; to, for example, suppress HIV transcription, suppress HIV activation, inhibit Tat transactivation, suppressing HIV activation by selectively targeting BRD4, suppress HIV in J-Lat cells, human peripheral blood mononuclear cells (PBMCs), and human CD4 T cells.

ZL0580

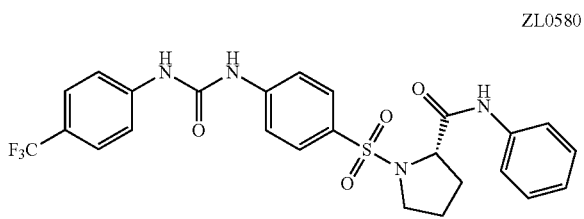

In some embodiments, the invention pertains to a method of suppressing HIV comprising, said method contacting one or more cells with ZL0580 or a pharmaceutically acceptable salt thereof.

In some embodiments, the invention pertains to a method of suppressing HIV transcription, said method comprising contacting one or more cells with ZL0580 or a pharmaceutically acceptable salt thereof.

In some embodiments, the invention pertains to a method of suppressing HIV activation by selectively targeting BRD4, said method comprising contacting one or more cells with ZL0580 or a pharmaceutically acceptable salt thereof.

In further embodiments, the invention pertains to a method of inhibiting Tat transactivation, said method comprising contacting one or more cells with ZL0580 or a pharmaceutically acceptable salt thereof.

In some embodiments, the invention pertains to a method of suppressing HIV comprising, said method contacting one or more cells with one or more compounds of Formulas I, II, III, IV, V, Va', Va", Vb, Vb', Vb", Ia, or Ib, or a pharmaceutically acceptable salt thereof.

In some embodiments, the invention pertains to a method of suppressing HIV transcription, said method comprising contacting one or more cells with one or more compounds of Formulas I, II, III, IV, V, Va', Va", Vb, Vb', Vb", Ia, or Ib, or a pharmaceutically acceptable salt thereof.

In some embodiments, the invention pertains to a method of suppressing HIV activation by selectively targeting BRD4, said method comprising contacting one or more cells with one or more compounds of Formulas I, II, III, IV, V, Va', Va", Vb, Vb', Vb", Ia, or Ib, or a pharmaceutically acceptable salt thereof.

In some embodiments, the invention pertains to a method of inhibiting Tat transactivation, said method comprising contacting one or more cells with one or more compounds of Formulas I, II, III, IV, V, Va', Va", Vb, Vb', Vb", Ia, or Ib, or a pharmaceutically acceptable salt thereof.

In further embodiments, the invention encompasses a method comprising contacting one or more cells with one or more compounds of Formulas I, II, III, IV, V, Va', Va", Vb, Vb', Vb", Ia, or Ib, or a pharmaceutically acceptable salt thereof, to, for example, suppress HIV transcription, suppress HIV activation, inhibit Tat transactivation, suppressing HIV activation by selectively targeting BRD4, suppress HIV in J-Lat cells, human peripheral blood mononuclear cells (PBMCs), and human CD4 T cells, etc.

In other aspects of the invention the preceding molecules (namely compounds of Formulas I, II, III, IV, V, Va', Va", Vb, Vb', Vb", Ia, or Ib, including ZL0580) may be used to suppress HIV in J-Lat cells. In other aspects of the invention these novel small molecules may be used to suppress HIV transcription. These novel small molecules may also be used to suppress HIV activation by selectively targeting BRD4. These molecules may also be used to inhibit Tat transactivation.

In further embodiments, the invention encompasses a method of treating HIV comprising administration of one or more compounds of Formulas I, II, III, IV, V, Va', Va", Vb, Vb', Vb", Ia, or Ib, or a pharmaceutically acceptable salt thereof to a subject.

In further embodiments, the invention encompasses a method of treating HIV comprising administration of one or more of the following compounds, or a pharmaceutically acceptable salt thereof:

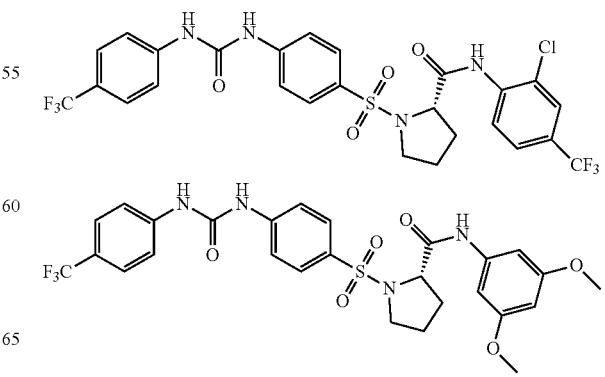

-continued

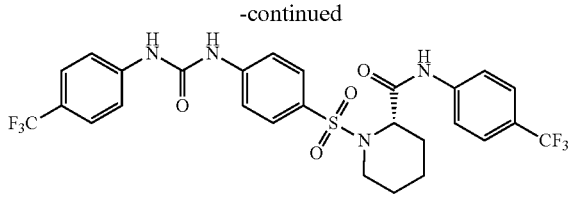
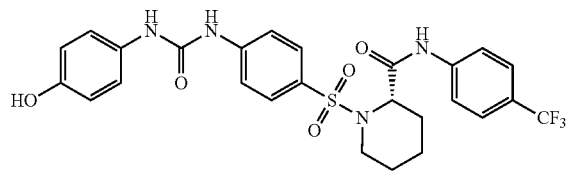
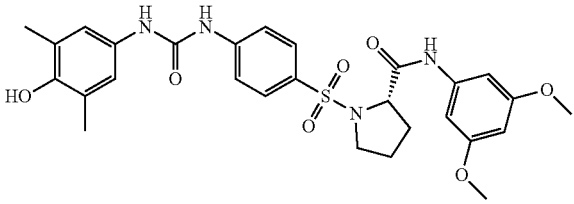
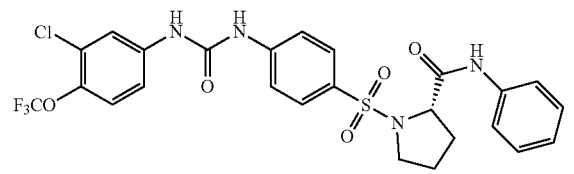
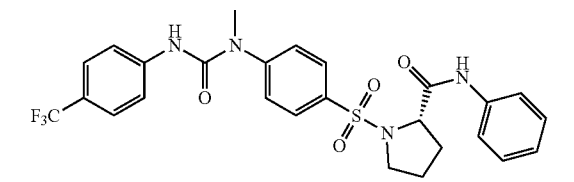
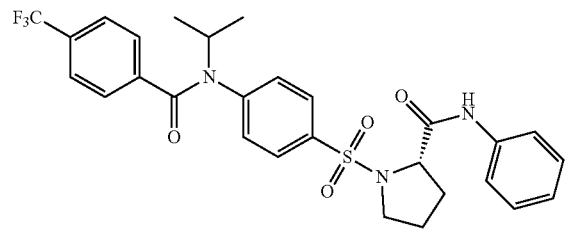
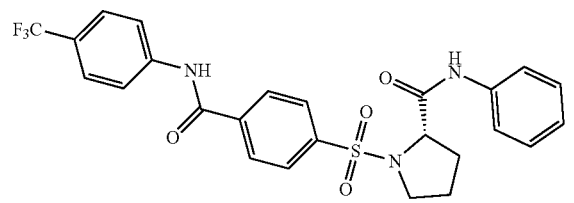
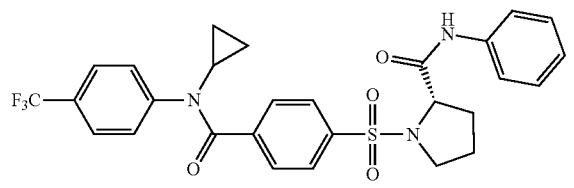
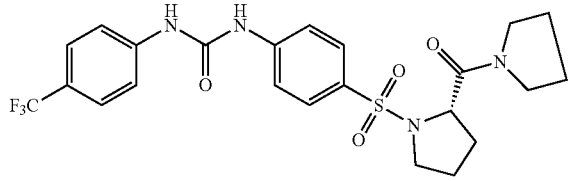

-continued

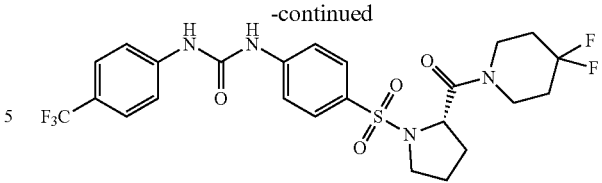

In further embodiments, the invention encompasses a method of treating HIV comprising administration of ZL0580, or a pharmaceutically acceptable salt thereof to a subject.

4.0 Examples

Example 1

Methods

Human Peripheral Blood Mononuclear Cells (PBMC).

This study involves use of PBMC samples from healthy human donors as well as from HIV-infected subjects. Healthy human donor PBMCs were obtained from the University of Texas Medical Branch (UTMB) blood bank and PBMCs of HIV-infected subjects were obtained from US Military HIV Research Program (MHRP) (RV21 cohort). All samples were analyzed anonymously and investigators of this study have no access to any subject identification information. The study was determined as non-human subject research and approved by both UTMB and MHRP IRBs. Written informed consents were obtained from study participants.

Cell Lines.

The J-Lat cell lines, including J-Lat Full Length Cells (clone 10.6, Cat. #9849), were obtained from the NIH AIDS Reagent Program. J-Lat cells were maintained in RPMI 1640 medium (Gibco) supplemented with penicillin G (100 U/mL), streptomycin (100 µg/mL), L-glutamine (2 mM, 0.3 mg/mL) and 10% (v/v) FBS. TZM-bl cells were maintained in DMEM medium (Gibco), with 10% FBS, 100 units of Penicillin and 0.1 mg/ml of Streptomycin. The cells were grown at 37° C. in humidified 5% $CO_2$ incubator.

Compound Design and Synthesis.

Compounds examined this study were designed and synthesized in the Chemical Biology Laboratory (Dr. Jia Zhou) of UTMB. Details regarding compound design and synthesis are available in the Supplementary Methods.

Binding Affinity Analysis.

Binding affinities of ZL0580 and JQ1 to bromodomains (BDs) of BRD4, BRD2, BRD3, and BRDT were determined using the Time-Resolved Fluorescence Energy Transfer (TR-FRET) assay (29). Details are available in the Supplementary Methods.

J-Lat Cell Treatments and Flow Cytometric GFP Analysis.

J-Lat full length 10.6 cells were used in majority of the compound screening and functional experiments. $0.25 \times 10^6$/well of J-Lat cells were plated in 96-well plates in culture medium (RPMI 1640 supplemented with 10% FBS, 1% L-glutamine and 1% penicillin/streptomycin). In HIV-activation screening experiment, cells were treated with individual compounds (10 µM) for 24 hours. Cells treated with DMSO (NC), JQ1 (10 µM) or PMA (100 ng/ml) were included as controls for comparison. In HIV-suppression screening experiments, cells were co-treated with PMA (100 ng/ml) and individual compound (10 µM) for 24 hours. Cells treated with PMA alone, PMA+JQ1 (10 µM) or DMSO (NC) were included as controls. In ZL0580 dose-response experiments, cells were treated with PMA (100 ng/ml) and various concentrations of ZL0580 (0, 1, 10 and 20 µM). In some experiments, cells were treated with ZL0580 24 hours prior to PMA stimulation to examine different treatment conditions. A2, 10.6 and A72 J-Lat cells were also used for similar treatment with ZL0580 in some experiment to determine Tat dependency. Cells were cultured in CO2 incubator at 37° C. during treatment. After treatments, cells were harvested, washed and stained for viability (Aqua Blue) and analyzed for GFP expression by flow cytometry.

In Vitro HIV Infection of PBMC, Compound Treatments and Flow Cytometric p24 Analysis.

Normal human PBMCs were cultured in 96-well plate ($0.4 \times 10^6$ per well) and stimulated with PHA (10 µg/ml) in the presence of various concentrations of ZL0580 (0, 0.25, 0.5, 2, 4 and 8 µM) or ZL0454 (0, 0.25, 0.5, 2, 4 and 8 µM) for 2 days. Cells were then infected with pre-titrated HIV (US-1 strain) (25, 47). No HIV infection of PHA-stimulated PBMC was included as control. 3 days after HIV exposure, cells were harvested and analyzed by flow cytometry for intracellular HIV p24 expression. Cells were stained for viability (Aqua Blue) and surface markers (CD3, CD4, and CD8), followed by fixation and permeabilization. Cells were then subjected to intracellular HIV p24 staining to measure productive HIV infection in CD4 T cells. Cells were analyzed by LSR-II.

Treatments of PBMC of HIV-Infected Subjects.

PBMCs of each subject were equally divided and stimulated with PHA (10 µg/ml) in the absence (DMSO: NC) or presence of ZL0580 treatment (10 µM). 2 days after treatment, cells were lysed and total RNA were extracted for PCR quantification of HIV Gag RNA as an indication of HIV transcription (described below).

Q-PCR Measurement of HIV RNA.

Total RNA was extracted from treated J-Lat cells or RV21 PBMC (as descried above), using the Quick-RNA Micro-Prep Kit (Zymo) according to the manufacturer's instructions. cDNA was synthesized from RNA using the iScript™ Reverse Transcription Supermix for RT-qPCR (Bio-Rad). HIV Gag or 3'TLR RNA was quantified by quantitative PCR using iTaq Universal SYBR Green Supermix (Bio-Rad) and the CFX Connect Real-Time PCR Detection System (Bio-Rad). Primer sequences for HIV Gag and 3'-LTR were shown in Table S1. PCR reactions (20 µl) contained 10 µM primers, 90 ng of cDNA, 10 µl iTaq universal SYBR Green supermix (2×) (Bio-Rad) and molecular grade water. PCR cycling conditions were as follows: 95° C. for 3 min, 45 cycles of 95° C. for 5 sec, 60° C. for 30 sec. Each reaction was performed in duplicate, and the mean Ct values were used. HIV Gag and 3'-LTR copy numbers were normalized to GAPDH and calculated using the $2^{-\Delta\Delta Ct}$ method.

TABLE S1

Primer sequences for Q-PCR in gene expression and CHIP analysis

| Primers | Sequence |
|---|---|
| Gag-f | 5'-GGAAGCTGCAGAATGGGATA-3' |
| Gag-r | 5'-GCTATGTCACTTCCCCTTGG-3' |
| 3'LTR-f | 5'-CAGATGCTGCATATAAGCAGCTG-3' |
| 3'LTR-r | 5'-TTTTTTTTTTTTTTTTTTTTTTTGAAG-3' |
| 5'LTR-f | 5'-GTTAGACCAGATCTGAGCCT-3' |
| 5'LTR-r | 5'-GTGGGTTCCCTAGTTAGCCA-3' |

CRISPR/Cas9 BRD4 and BRD2 Knockout.

BRD4 and BRD2 gene editing and protein knockout (KO) in J-Lat cells were carried out using CRISPR/Cas9 as we previously reported (48). Briefly, gene specific guide sequences (Supplementary Table 1) were designed to target BRD2 or BRD4 using the online tool (http://crispr.mit.edu/) and were cloned into lentiCRISPR v2 vector (a gift from Dr. F. Zhang; Addgene plasmid number 52961). The constructed plasmids or empty lentiCRISPR V2 plasmid together with lentivirus packaging plasmids, psPAX2 (a gift from D. Trono; Addgene plasmid number 12260) and pCMV-VSV-G (a gift from B. Weinberg; Addgene plasmid number 8454), were used to co-transfect 293T cells for producing lentivirus. Packaged lentiviruses were then used to transduce J-Lat full cells. Target gene KO and the KO control (empty vector) J-Lat cells were selected and maintained in complete RPMI 1640 medium supplemented with 10 µg/ml puromycin. To validate the efficacy of CRISPR/Cas9-mediated gene KO, BRD4 and BRD2 protein expression was measured by western blotting in gene-KO and control J-Lat cells.

Western Blotting.

Target protein expression in WT and BRD4-KO J-Lat cells (10.6 full length) were measured by western blotting. $15 \times 10^6$ cells were treated with PMA alone, PMA+ZL0580, PMA+JQ1, or untreated (NC) as described above. The cells were harvested, washed and then lysed in NP-40 cell lysis buffer (containing 20 mM Tris-HCl, 0.15 mM of NaCl, 0.2 mM EDTA, 1% NP40, protease inhibitor cocktail, and 1 mM PMSF) by rotation at RT for 1 hour. Cell lysates were centrifuged at 4° C. and the supernatants were collected, followed by measurement of total protein concentration in the supernatants by using Microplate BCA Protein Assay Kit. 20 µg proteins were separated using SDS-PAGE gel and then transferred to Immuno-Blot PVDF Membrane. The membrane was blocked (5% skimmed milk powder in TBST) and then incubated with individual protein-specific antibodies (CDK9, Cyclin T1, Cyclin T2, ELL2, p-RNA Pol II-CTD (Ser2), BRD2, BRD4, NF-κB, or cellular GAPDH) for overnight at 4° C. After washing three times in TBST, the membrane was incubated with anti-rabbit or anti-mouse IgG-HRP, depending on the primary antibody used. The membrane was incubated in Super Signal West Pico Chemiluminescent Substrate. Molecular weights of target proteins were assessed by comparing with markers.

Co-Immunoprecipitation.

Treated J-Lat cells were harvested, washed and lysed in 1 ml NP-40 cell lysis buffer as described above in western blotting. The lysate was cleared by centrifugation and the supernatant was collected. Protein concentration in collected supernatant was measured (Microplate BCA Protein Assay Kit). Equal amounts of proteins from different treatments were incubated with 2 g of anti-Tat (Thermo Fisher, Cat. No. MA1-71509) or anti-BRD4 (Thermo Fisher, Cat. No. 730037) antibody or normal mouse IgG (Cell Signaling, Cat. No. 5415) for overnight at 4° C. The immune complexes were precipitated by 50 µl protein G-conjugated magnetic beads (Thermo Fisher, Cat. No. 10003D). Beads were washed 6 times using cold NP-40 cell lysis buffer and then subjected to SDS-PAGE electrophoresis. The membranes were immunoblotted with anti-CDK9 primary antibody, followed by incubation with HRP-conjugated secondary antibody.

Chromatin Immunoprecipitation (ChIP).

ChIP assay was performed using a ChIP-IT Express Kit (Active Modify, USA) according to the manufacturer's instructions. Briefly, $15 \times 10^6$ cells were transferred to 6-well plate and treated with PMA (100 ng/ml)+ZL0580 (10 µM), PMA (100 ng/ml)+JQ1 (10 µM), PMA alone or untreated (NC), for 24 hours. Cells were harvested and washed. Cell pellets were re-suspended in 10 ml PBS buffer and fixed with 37% formaldehyde to cross-link DNA and proteins. The fixation reaction was stopped by adding 1.1 ml of 10× Glycine for 5 min at RT. Cells were centrifuged and the supernatants were removed, followed by re-suspension of cells in ice-cold Lysis Buffer on ice for 30 min. Cells were centrifuged at 5,000 rpm for 10 min to pellet the nuclei. Nuclei pellets were re-suspended in 700 µl shearing buffer plus 3.2 µl of PIC and 3.2 µl of PMSF, and were then sonicated using the determined conditions. Sheared chromatin samples were used to set up ChIP reactions by adding the magnetic beads and 5 µg of anti-Tat (1 mg/ml, Thermo Fisher, MA1-71509) or control mouse IgG (2.5 mg/ml, Cell Signaling, #5415) antibody (overnight rotation at 4° C.). After several times of washing by ChIP buffers 2, the chromatin was reverse cross-linked and treated with proteinase K. The eluted DNA were cleaned up with phenol-chloroform and used in real time-PCR. The primer sequences used in CHIP-qPCR were shown in Table S1. The results were analyzed by the fold enrichment method with the formula % enrichment=2−(CT IP−CT mock).

MNase Nucleosomal Mapping.

Following treatments, J-Lat cells were cross-linked using the same method as described in the CHIP assay. Cells were then washed with 1 ml buffer B (0.25% Triton-X 100, 1 mM EDTA, 0.5 mM EGTA, 20 mM Herpes, pH 7.6) and 1 ml buffer C (150 mM NaCl, 1 mM EDTA, 0.5 mM EGTA, 20 mM Herpes, pH 7.6). Following one wash in cold PBS, ~15×10$^6$ cross-linked cells were suspended in 1 ml buffer A (300 mM sucrose, 2 mM Mg acetate, 3 mM Cacl2, 10 mM Tris pH 8.0, 0.1% Triton X-100, 0.5 mM DTT), incubated on ice for 5 min, and then dounced with 2 ml dounce grinders (Tight Pestle, Kontes) for 20 times. Nuclei were collected by centrifuging at 4° C., 750×g for 5 min. Pellets were washed twice in 1 ml buffer D (25% glycerol, 5 mM Mg acetate, 50 mM Tris pH 8.0, 0.1 mM EDTA, 5 mMDTT) at 15×10$^6$ nuclei/ml. Chromatin was collected by centrifuging at 4° C., 750×g for 5 min. The pellets were suspended in 1 ml buffer MN (60 mM KCl, 15 mM NaCl, 15 mM Tris pH 7.4, 0.5 mM DTT, 0.25 mM sucrose, 1.0 mM CaCl$_2$) at 1.5×10$^7$ nuclei/ml. 150 µl aliquots (2.25×10$^6$ nuclei) were treated with 0, 0.5, 5, 20, 50, or 500 U/ml of MNase (USB) for 30 min at 37° C. Reactions were stopped by addition of EDTA (12.5 mM) and SDS (0.5%). After 4 hours of proteinase K digestion at 37° C., each reaction was processed similar to that in ChIP assay from the point of DNA elution. After measuring concentrations, digested and undigested DNA samples were diluted to the same concentration (5 ng/µl) and used for real-time qPCR analysis. Fold change was calculated using delta CT method and the ratio of the amount of digested DNA to the undigested DNA for each primer was calculated.

Statistical Analysis.

Statistical analysis was performed using Prism 6.0 (GraphPad). Statistical comparison between groups was performed using paired or non-paired t test. Two-tailed p values were denoted, and p values <0.05 were considered significant.

Discovery of a Novel Small Molecule that Suppresses HIV in J-Lat Cells

We have synthesized a batch class of small molecules designed to modulate BRD4 (35) and screened these compound libraries for their activities on HIV transcription using the HIV latently infected J-Lat cells (full-length; 10.6) (36). Our initial goal was to identify new BRD4 modulators that are superior to JQ1 in activating latent HIV and, therefore, will serve as more potent latency reversing agents (LRA). Cells were treated with individual compounds, carrier (DMSO; NC), JQ1, or PMA (positive control) singly for 24 hours. Activation of latent HIV was measured based on detection of GFP expression by flow cytometry. In one compound library (62 compounds; named as C1-C62), we identified three compounds (ZL0454, ZL0482, and ZL0519) that modestly activate HIV; however, their potency is either weaker than or comparable with JQ1 (FIG. 8).

Figure 1A:
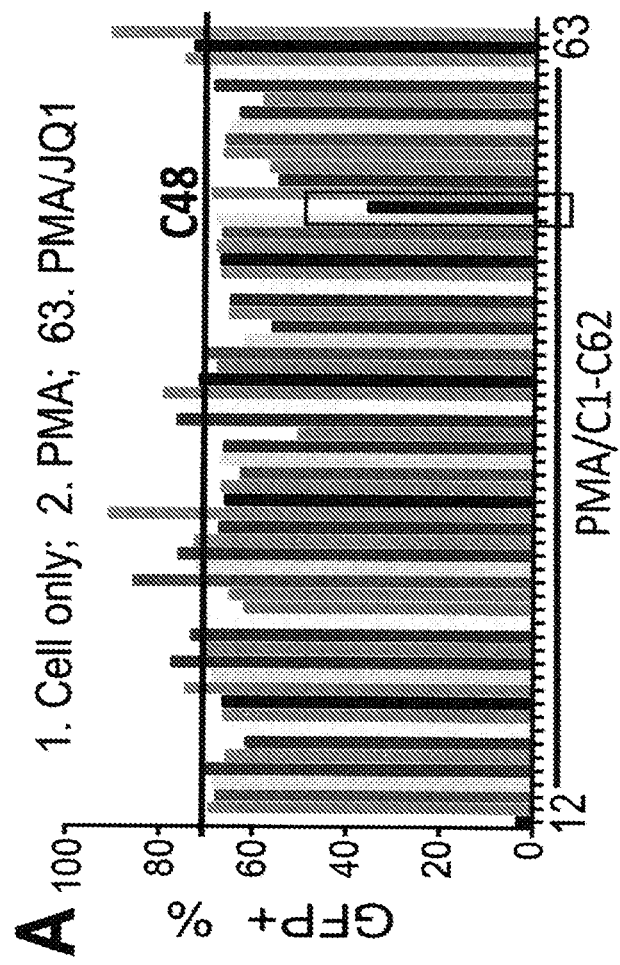
FIG. 1. Discovery of a small molecule suppressing HIV in J-Lat cells. (A) Screening of compounds (C1-C62) designed as new BRD4 modulators in J-Lat cells (10.6). Cells were stimulated with PMA (1 µg/ml) to activate HIV and treated with individual compounds (10 µM) for 24 hours (PMA/C1-C62). Cell only (NC), PMA, and PMA/JQ1 (10 µM) were included as controls (labeled as 1, 2, and 63). HIV activation was measured by flow cytometry (GFP+%). (B) Chemical structure of ZL0580. (C-D) Dose-dependent suppression of PMA-induced HIV activation by ZL0580. Cells were treated with PMA and ZL0580 (0 µM, 1 µM, 10 µM, 20 µM) for 24 hours. NC or PMA/JQ1 (10 µM) were included as controls. Representative FACS plots for GFP expression (C) and cumulative data for % GFP+ in J-Lat cells of three experimental repeats (D) (mean±SD) are shown. (E) Comparison of HIV transcription. HIV RNAs (Gag and 3'LTR) were quantified by qPCR in cells 24 hours after treatment. Results are shown as fold change to NC. (F-G) Kinetics of ZL0580-induced HIV suppression in PMA-activated (F) or resting (G) J-Lat cells. Cells were treated as indicated for 24 hours. HIV 3'-LTR RNA was quantified on Day 2, 7 and 14 after treatment. Data are shown as fold change to NC for each time point. * and ** denote comparison of PMA/ZL0580 or PMA/JQ1 with PMA (F), or comparison of ZL0580 or JQ1 with NC (G). Error bars in (E-G) represent SD of PCR duplicate. (H) Un-stimulated J-Lat cells were treated with NC or ZL0580 (10 µM), followed by stimulation with SAHA or Prostratin three days after treatment. HIV reactivation was measured based on 3'-LTR RNA and results are shown as fold change to NC. All experiments were repeated at least three times. *p<0.05; **p<0.005 by one-way ANOVA (D) and paired student t-test (E-H).
Figure 1B:
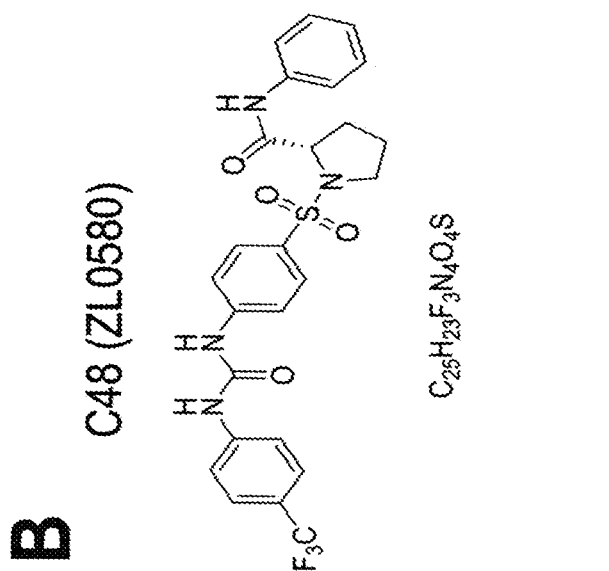
Figure 1E:
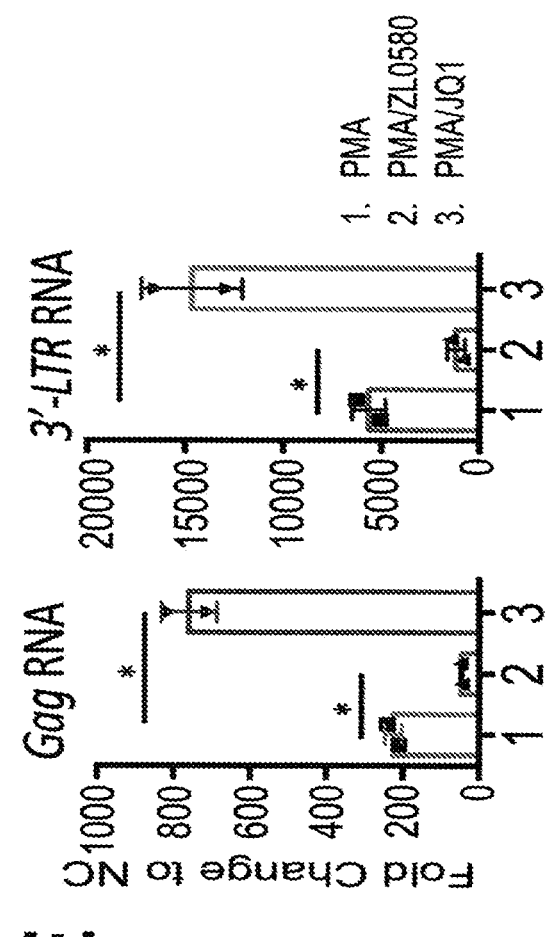
Figure 1D:
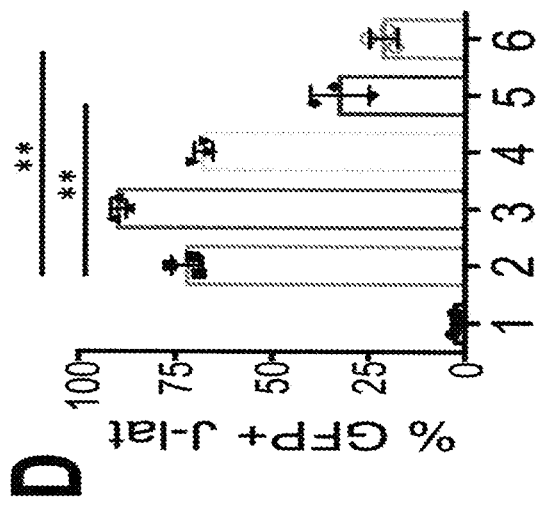
Figure 1G:
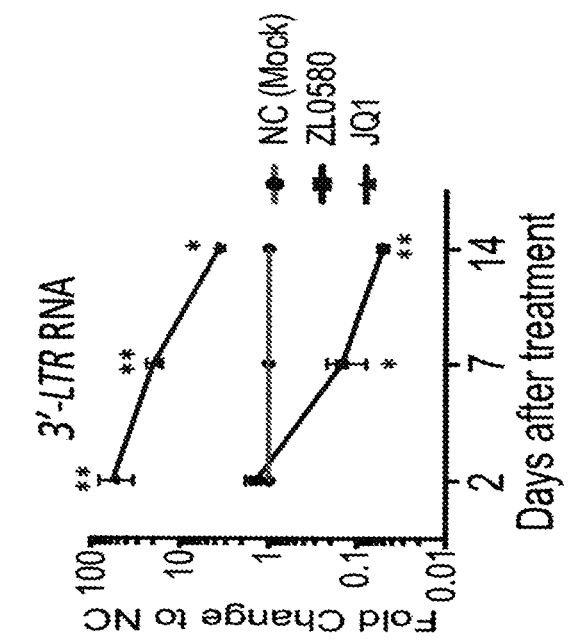
Figure 1F:
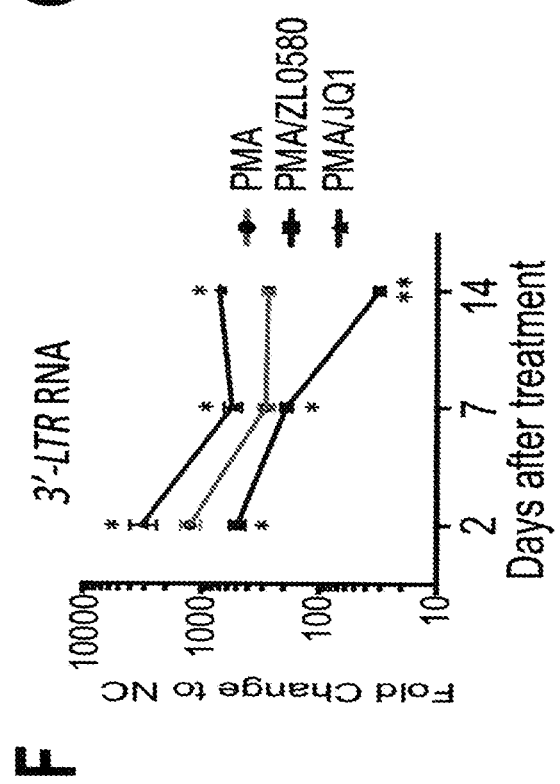
Figure 1H:
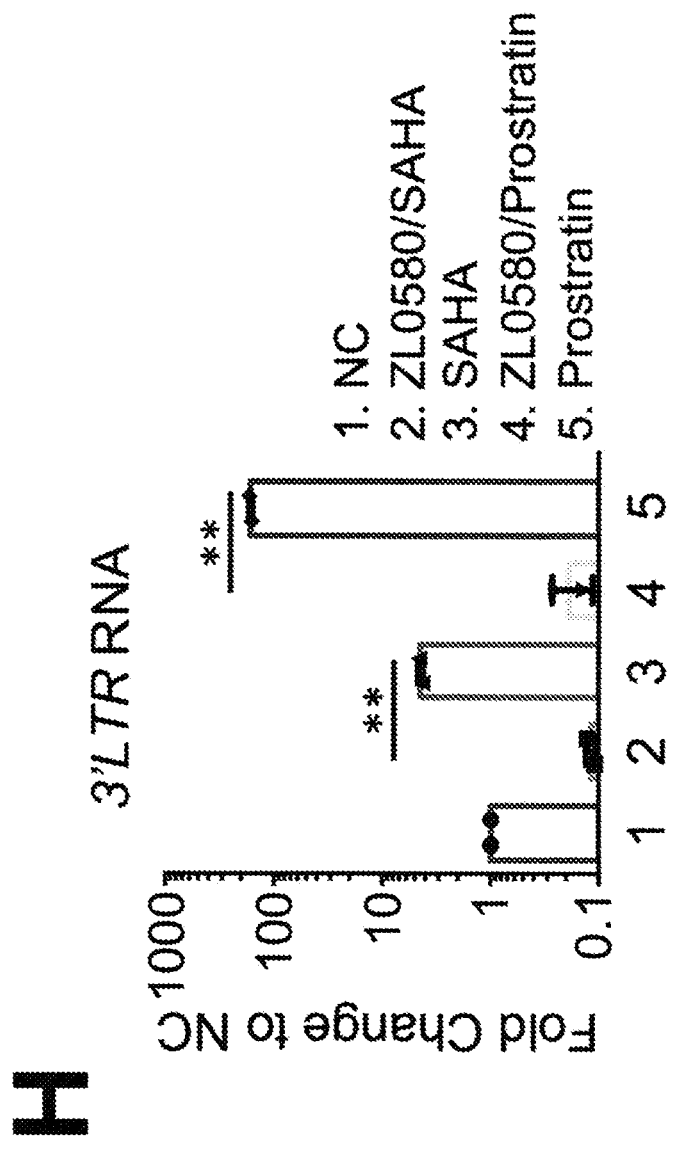

Intriguingly, in an HIV suppression model where J-Lat cells were stimulated with PMA to activate HIV and treated with individual compounds, we identified one lead compound (C48: ZL0580) that is distinct from JQ1 but suppresses PMA-induced HIV activation (FIG. 1A). The chemical structure of ZL0580 is shown in FIG. 1B with its design and synthesis detailed in the supplemental material. Further analysis showed that ZL0580 suppresses PMA-induced HIV activation in dose-dependent manner (FIG. 1C-D). As a control, JQ1 alone activates HIV and synergistically enhances PMA-stimulated HIV activation (FIG. 1C-D). To determine whether HIV suppression by ZL0580 occurs at transcriptional level, we quantified HIV mRNAs and showed that ZL0580 reduces both Gag and 3'-LTR RNA levels, while JQ1 enhances their levels (FIG. 1E), supporting that ZL0580 induces HIV transcriptional suppression. Kinetic analysis showed that single ZL0580 treatment (10 µM) suppresses both PMA-stimulated and basal HIV transcription through Day 14 after treatment (FIG. 1F-G). In J-Lat cells, basal HIV transcription in resting condition is readily detectable by qPCR (Cq values shown in FIG. 9). In addition, we treated resting J-Lat cells with a single dose of ZL0580 for 3 days, followed by reactivation by LRAs. ZL0580 pre-treatment renders J-Lat cells more resistant to HIV reactivation by SAHA or Prostratin (FIG. 1H), indicating that ZL0580 may induce epigenetic reprogramming of HIV LTR.

We examined toxic effect of ZL0580 on J-Lat cells by treating them with a wide range of ZL0580 (0-80 µM) for various lengths of time (1 & 3 days), followed by live/dead aqua blue staining and flow cytometric analysis for cell viability. ZL0580 did not cause significant cell death at concentrations below 40 µM (Part A, FIG. 10). In the HIV-suppression kinetic analysis (FIG. 1F-G), treatment of J-Lat cells with ZL0580 (10 µM) also did not cause significant cell death on Day 2, 7 and 14 as compared to NC in both PMA-activated and un-stimulated cells (Part B, FIG. 10). These data indicate that the observed effect of ZL0580 is independent of cell toxicity.

In this compound library, in addition to ZL0580, we noted that two other compounds (ZL0506 and ZL0549) can also modestly suppress HIV (FIG. 11). In contrast, the three compounds described above (ZL0482, ZL0454, and ZL0519) that could activate latent HIV manifested similar effects to JQ1 and synergistically enhanced PMA-induced HIV activation (FIG. 11C). These data suggest that instead of being a pan-assay interference compound (37), the HIV-suppressive effect of ZL0580 in J-Lat cells is specific.

ZL0580 Suppresses HIV in In Vitro HIV-Infected Human Primary CD4 T Cells

Figure 2A:
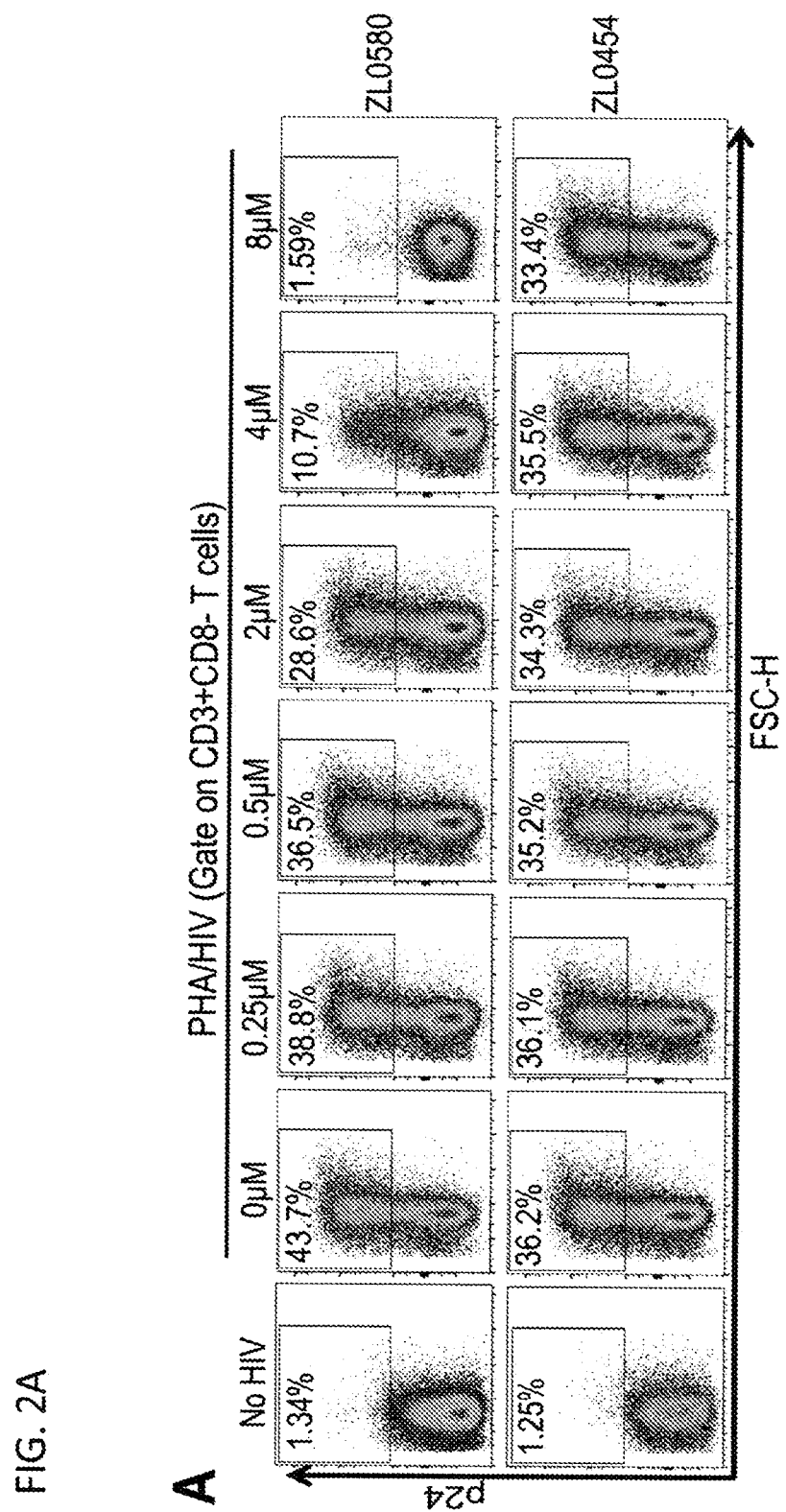
FIG. 2. HIV suppression by ZL0580 in in vitro HIV-infected human CD4 T cells. (A) HIV infection of PHA-activated CD4 T cells in normal PBMCs. PBMCs (n=3) were stimulated with PHA (1 µg/ml) for two days, followed by infection with R5 HIV (US-1) in the absence or presence of ZL0580 (top) or ZL0454 (bottom) at various concentrations as indicated. Three days after viral exposure, HIV infection in CD4 T cells was measured by flow cytometry based on intracellular p24 staining. Representative FACS plots are shown. (B) Comparison of % p24+ CD4 T cells in PBMCs. (C-D) Quantification of HIV DNA (C) and Gag RNA (D) in PBMCs following different treatments by qPCR. Data are shown as fold change of PHA/ZL0580 (4 µM) to PHA alone. (E) Representative FACS plots showing HIV infection (intracellular p24) of unactivated CD4 T cells in PBMCs on Day 6 after treatments. (F) Comparison of p24+% in unactivated CD4 T cells in PBMCs. (B-D and F) Mean±SD from three PBMC donors. * p<0.05; ** p<0.01 by one-way ANOVA (B, F) and paired student t-test (C-D).

To determine if ZL0580 can suppress HIV in a more relevant system, we used human CD4 T cells that were infected with HIV in vitro. Normal PBMCs were stimulated with PHA (typically more efficient in activating T cells than PMA for longer-term culture) for 2 days, followed by HIV infection (US-1 strain) in the presence of ZL0580 (0-8 µM) or a control compound ZL0454 (0-8 µM). ZL0454 was selected from the same library since ZL0580 did not suppress HIV in J-Lat cells (FIG. 18; FIG. 11C). HIV infection in CD4 T cells was examined three days after viral exposure by flow cytometry based on intracellular p24 expression. Consistent with the results in J-Lat cells, ZL0580 could also suppress HIV in activated human CD4 T cells in a dose-dependent manner (FIG. 2A-B). Of note, the potency of ZL0580 to suppress HIV in primary CD4 T cells appeared to be stronger than that in J-Lat cells, since single ZL0580 treatment (8 µM) led to almost complete loss of productive HIV infection in CD4 T cells (FIG. 2A-B). As a control, treatment with ZL0454 did not suppress HIV in CD4 T cells (FIG. 2A-B). To ensure that ZL0580 itself did not affect HIV infection of PBMCs, we quantified cell-associated HIV DNA and found that ZL0580 treatment did not significantly alter HIV DNA levels (FIG. 2C), but reduced HIV transcription in PBMCs (FIG. 2D).

Figure 2E:
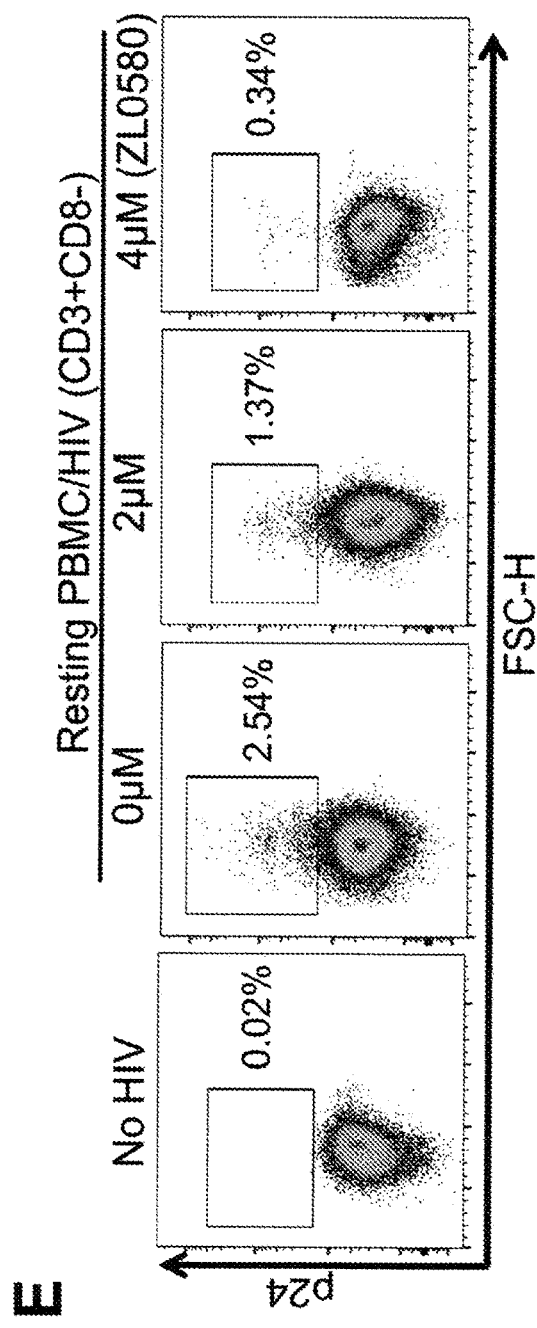
Figure 2F:
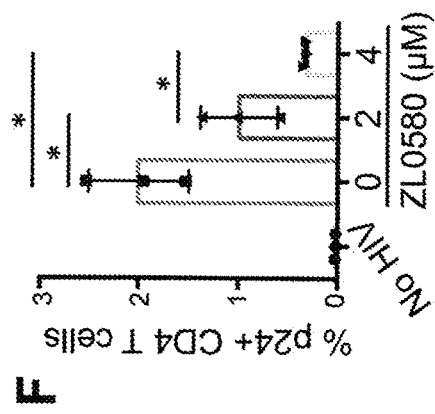

We also evaluated the impact of ZL0580 on HIV in un-activated (resting) CD4 T cells. Normal PBMCs were not stimulated but directly infected with HIV by spinoculation. 24 hours after HIV infection, cells were extensively washed and treated with ZL0580 (2 µM and 4 µM) or not (NC). As expected, compared to activated cells, HIV replication kinetics in un-activated CD4 T cells is slower. However, we were able to detect low but significant level of HIV replication (intracellular p24 expression) on Day 6 after HIV inoculation (% p24+: 2.54%) (FIG. 2E). Of importance, ZL0580 also dose-dependently suppresses HIV in unactivated CD4 T cells (FIG. 2E-F).

Figure 12B:
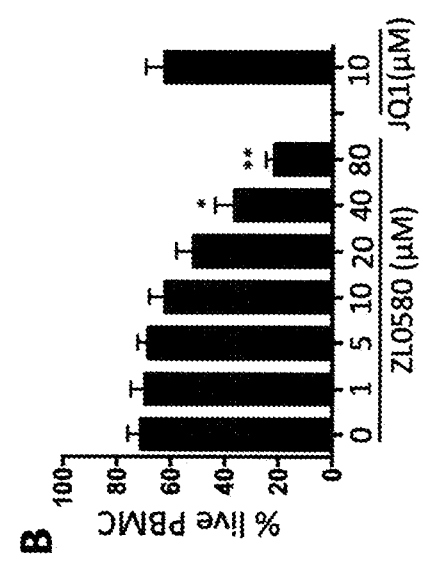
Figure 12A:
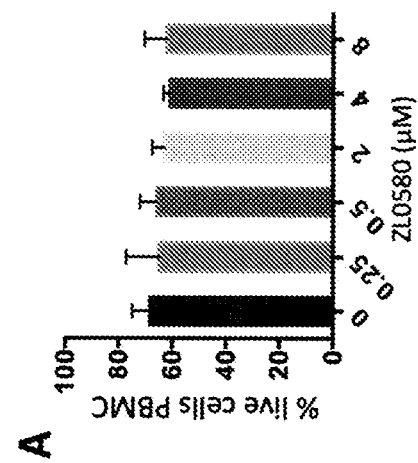

We assessed PBMC viability and found that it was comparable between NC and ZL0580 treatment (at 8 µM) (FIG. 12A), indicating that the HIV suppressive effect of ZL0580 in human CD4 T cells was not due to overt cell toxicity. Potential toxic effect of ZL0580 on PBMCs was evaluated with wider range of ZL0580 concentrations (0-80 µM). Similar to the results in J-Lat cells, ZL0580 did not cause significant PBMC death at concentrations below 40 µM (FIG. 12B).

We further examined the effects of ZL0580 on T-cell phenotypes and activation makers associated with HIV infection and replication. ZL0580 did not significantly alter the expression of HIV entry receptors (CD4 and CCR5) on CD4 T cells (FIG. 13, Part A-B). Expression of activation markers (CD25, CD38 and HLA-DR) is also comparable between NC and ZL0580 treatment for both activated and un-activated T cells (FIG. 13, Part C-D). To more broadly assess the impact of ZL0580 on T cells, we examined the expression of an array of genes in PHA-activated and resting PBMCs following ZL0580 treatment or not. A total of 17 genes closely associated with T-cell phenotypes and functions were chosen, including cytokines and chemokines, transcription factors, lineage differentiation factors, innate HIV restriction factors and transcript elongation factors (FIG. 13, Part E-F). The data showed that ZL0580 did not significantly alter the expression of these genes in PBMCs (FIG. 13, Part E-F), indicating that ZL0580 did not induce global changes in human T cells.

ZL0580 Suppresses HIV Transcription Ex Vivo in PBMC of HIV-Infected Subjects

Figure 3:
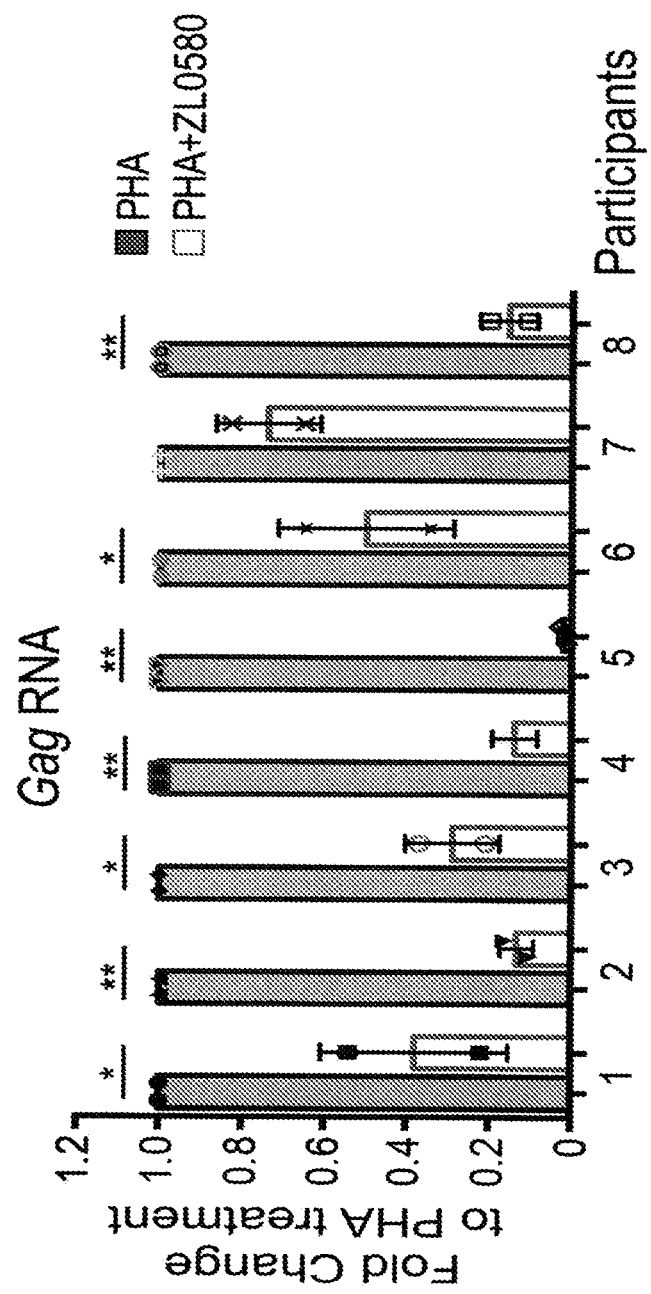
FIG. 3. ZL0580 suppresses HIV transcription ex vivo in PBMCs of viremic HIV-infected individuals. PBMCs of RV21 participants (n=8) were activated by PHA and treated with ZL0580 (8 µM) or not. Two days after treatments, cell-associated HIV Gag RNA was quantified by qPCR. For each PBMC, data is shown as fold change of PHA+ZL0580-treated cells to PHA-treated cells. PCR was conducted in duplicate and error bars represent SD of PCR replicate for each PBMC. *p<0.05; **p<0.005 by paired student t-test.

We next assessed assess the HIV-suppressive activity of ZL0580 ex vivo. RV21 is ART naïve, chronic HIV infection established by US MHRP and use of PBMC samples from this cohort in our group has been previously published (25). PBMC from RV21 subjects (n=8) were stimulated with PHA to induce HIV transcriptional activation in the absence (0 Mm) or presence of ZL0580 (8 Mm). HIV Gag mRNA was quantified by Q-PCR 2 days after treatment. Consistent with the results from in vitro HIV-infected PBMC, ZL0580 could also suppress HIV transcription ex vivo in all eight PBMC samples from HIV-infected individuals we have examined (FIG. 3A); in some subjects, the reduction of RNA levels by ZL0580 was greater than 10-fold (FIG. 3A). Consistent with the reduction in HIV transcription, production of HIV particles in cell culture supernatants, which was measured based on the reporter TZM-bl assay, was also significantly reduced by ZL0580 treatment as compared to no treatment control (FIG. 3B). Therefore, these data also suggest that ZL0580 can suppress HIV ex vivo in PBMC of HIV-infected human individuals.

ZL0580 Suppresses HIV in PBMCs of Aviremic HIV-Infected Participants

Figure 4D:
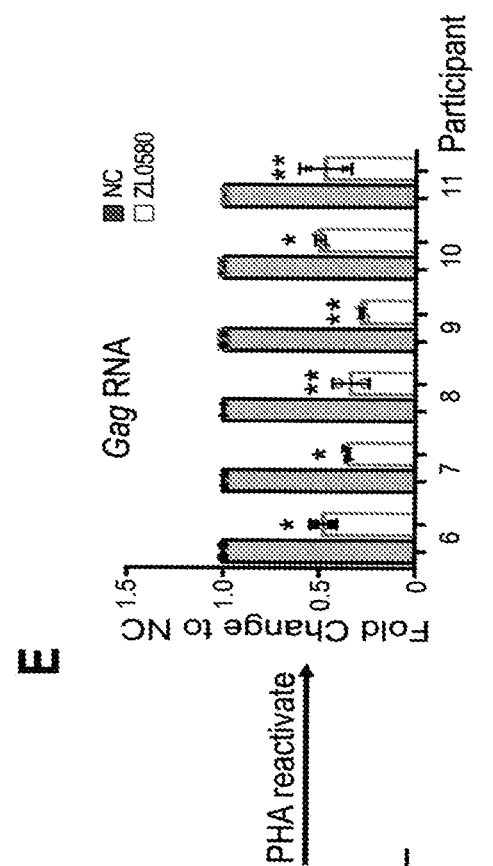
FIG. 4. Suppressive effect of ZL0580 on HIV in PBMCs of ART-suppressed, aviremic HIV-infected participants. (A) PBMCs of aviremic RV254 participants (n=5) were stimulated with anti-CD3/CD28 and cultured in IL-2 containing medium to induce latent HIV activation and CD4 T-cell expansion. Cells were treated with ART alone, ART+ZL0580 (2.5 µM), or mock treated (NC). HIV release in supernatants was quantified by the two-step nested qPCR. Following full HIV suppression, treatments were stopped and viral RNA copies were continuously monitored every three days. Data are shown as HIV copies (log 10) per 10^6 PBMCs. (B-C) Quantitative analysis of the effect of ZL0580 on promoting HIV suppression during ART (B) and on viral rebound following ART cessation (C). Comparison of length of time (Days) and area under the curve (AUC) prior to treatment cessation (B) and post treatment cessation to first viral rebound (C) between ART and ART+ZL0580 for the five PBMCs. AUC for each PBMC was quantified using Prism. (D) HIV production by unactivated RV254 PBMCs (n=6). PBMCs were directly treated with ZL0580 (2.0 µM) or not (NC) on Day 0, 3, 6 (treatment stopped on Day 9). HIV production in supernatants was measured once every 3 days as indicated. (E) After Day 18, PBMCs were stimulated with PHA to reactivate latent HIV. HIV transcriptional reactivation was measured by quantifying Gag RNA in cells. The data is shown as fold change of ZL0580 treatment to NC for each PBMC. (A and D-E) PCR was conducted in duplicate and error bars show PCR replicate SD. *p<0.05; **p<0.005 (B, C and E) by paired student t-test.
Figure 4E:
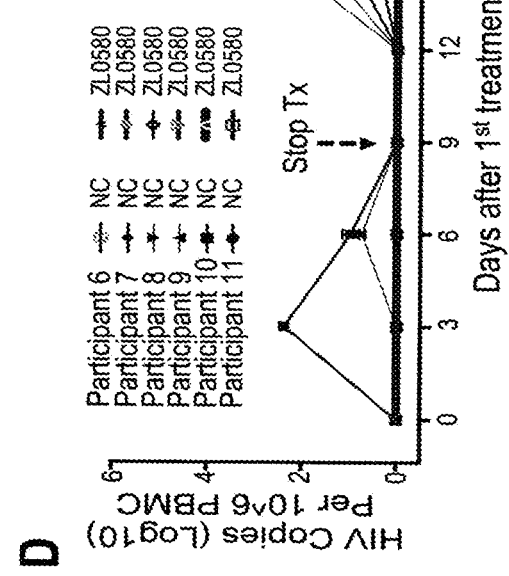

To explore impact of ZL0580 on latent HIV, PBMCs of ART suppressed, aviremic HIV-infected participants in RV254 cohort (39) were examined in two different models. First, PBMCs (n=5; 6-month post ART) were stimulated with anti-CD3/CD28 to activate latent HIV and to induce CD4 T-cell expansion. An advantage of this model is that expanded T cells can be cultured for >3-4 weeks with good viability and allow durability analysis (22). Cells were treated with ART alone (Efavirenz, Zidovudine, Raltegravir), or ART+ZL0580 (2 µM), or mock (NC) in IL-2-containing medium. ART was initiated at the beginning to control spreading infections. Medium was replaced every 3 days (maintaining the same drugs) and HIV production was measured by ultra-sensitive nested PCR (22). We showed that this PCR method can sensitively detect <10 HIV copies (FIG. 14). As shown in FIG. 4A, while HIV production kinetics varies among the five PBMCs, ZL0580 treatment promotes HIV suppression during ART and delays viral rebound after ART cessation (FIG. 4A). Quantitative analysis was performed to evaluate the impact of ZL0580 on promoting HIV suppression (before treatment cessation) and on viral rebound (after treatment cessation) by comparing the length of time (days) and area under the curve (AUC) between ART alone and ART+ZL0580. For HIV suppression, ART alone requires 15±3.3 days to induce full suppression, whereas ART+ZL0580 requires 12±3.6 days ($p<0.05$) (FIG. 4B). Comparison of AUC before treatment cessation also revealed modest, but significant, difference between ART and ART+ZL0580 (FIG. 4B). Notably, the impact of ZL0580 on viral rebound is more significant (FIG. 4C). For ART alone, viral rebound was quickly detected within 3-6 days in all 5 PBMCs after treatment removal, while ART+ZL0580 led to marked delay in viral rebound in 3 out of 5 PBMCs (FIG. 4A). Similar quantitative analysis showed that days to viral rebound in ART alone and ART+ZL0580 treatments were 2.4±1.3 and 15±6.1, respectively ($p<0.005$) (FIG. 4C). Comparison of AUC (after treatment cessation) also revealed significant difference between the two groups ($p<0.05$) (FIG. 4C). Through the experiments, we closely monitored cell viability and observed that while PBMC viability decreased over time, ZL0580 treatment did not cause significant toxicity to these cells as compared to ART alone or NC (FIG. 15). Experiments were terminated when total cell viability dropped below 30% (around 27-33 days after initial treatment).

ZL0580 Suppresses HIV Activation Via BRD4

Figure 5C:
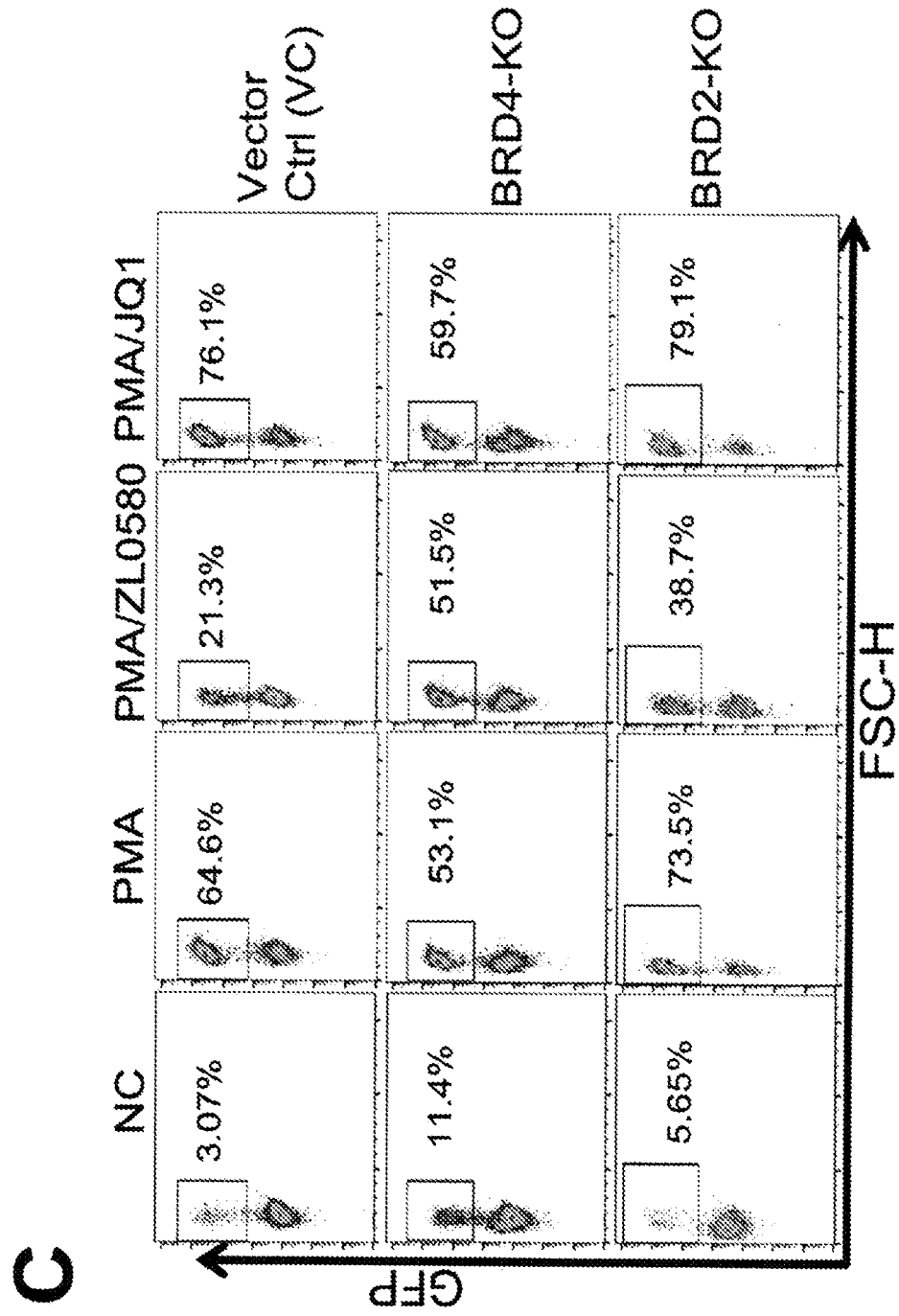
FIG. 5. ZL0580 selectively binds to BRD4 (BD1) and BRD4 is functionally required for ZL0580-induced HIV suppression. (A) In vitro binding of ZL0580 or JQ1 to BD1 and BD2 of BET proteins measured by TR-FRET (IC50: nM). Error bars represent SD of assay replicates. (B) CRISPR/Cas9 knockout (KO) of BRD4 and BRD2 in J-Lat cells. (C-D) BRD4 KO abrogates ZL5080-induced HIV suppression. Vector Ctrl (VC), BRD4-KO or BRD2-KO cells were treated as indicated. Representative FACS plots for GFP expression (C) and cumulative data comparing GFP+% in VC and KO J-Lat cells from 3 independent experiments (mean SD) (D) are shown. (E) Expression of Gag and 3'-LTR RNAs in PMA-activated, VC or BRD4-KO cells after treatments (24 hours). (F) Expression of 3'-LTR RNA in un-stimulated, VC or BRD4-KO J-Lat cells after different treatments (on Day 7). (G) Exogenous BRD4 expression in BRD4-KO J-Lat. KO cells were nucleofected with pcDNA-FLAG-BRD4 plasmid (+) or not (−). BRD4 expression was measured by WB using anti-BRD4 and anti-FLAG antibody (Day 4 after nucleofection). VC was included as a control. (H-I) Effect of BRD4 overexpression on ZL0580-induced HIV suppression. BRD4-KO cells without (top) or with BRD4 overexpression (bottom) were treated as indicated. Representative FACS plots for GFP expression (H) and cumulative data comparing GFP+%
Figure 5D:
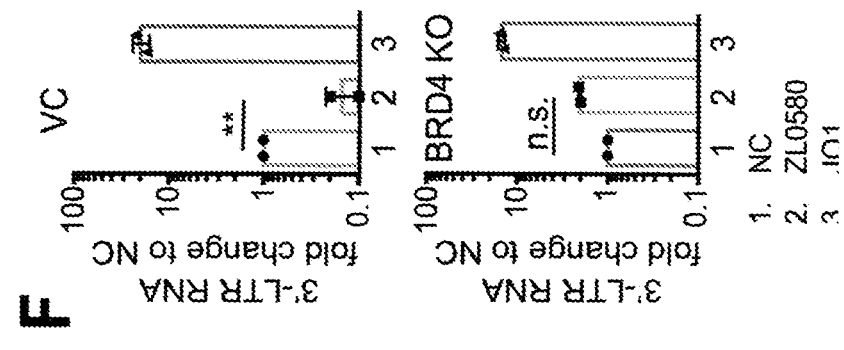

To understand mechanisms underlying ZL0580-induced HIV suppression, we explored roles of BET proteins. BET proteins consist of BRD2, BRD3, BRD4, and BRDT (25), among which BRD4 and BRD2 were shown to participate in HIV transcriptional regulation (30, 32, 40). First, we measured binding affinity of ZL0580 to BDs of BET as compared to JQ1 using TR-FRET assay and found that JQ1 non-selectively binds to both BD1 and BD2 all four BET proteins (FIG. 5A), consistent with the previously described role of JQ1 as a pan-BET inhibitor (33). In contrast, ZL0580 more selectively binds to BRD4 BD1 domain ($IC_{50}$=163 nM) instead of BD2 ($IC_{50}$=1,071 nM). ZL0580 also displays 6~11-fold selectivity for BRD4 over other BET proteins ($IC_{50}$ ranges from 0.9~1.9 µM) as well as over a non-BET bromodomain protein CBP ($IC_{50}$>10 µM) (FIG. 5A). We also assessed binding activity of ZL0580 to a broader panel of non-specific cellular proteins and showed that ZL0580 also manifests no or weak binding activity towards these non-specific targets (Table S1).

Figure 5E:
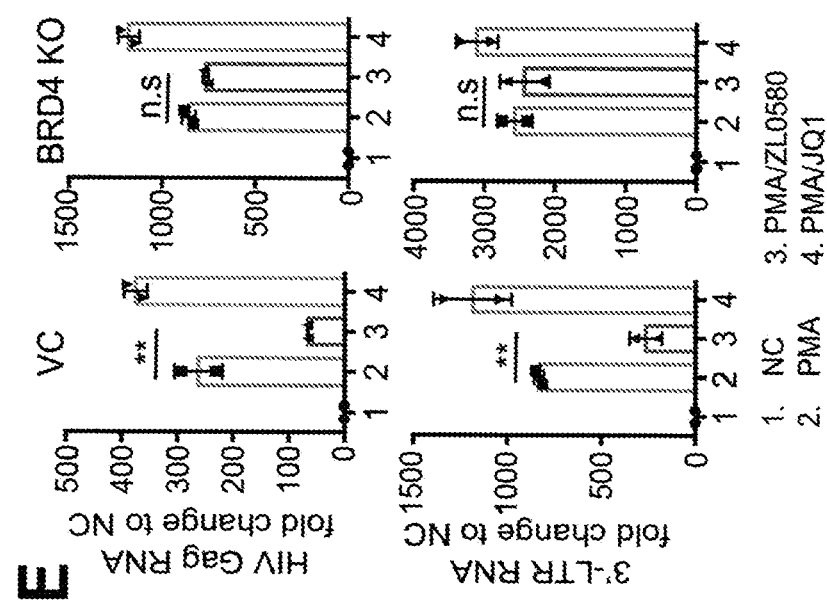
Figure 5F:
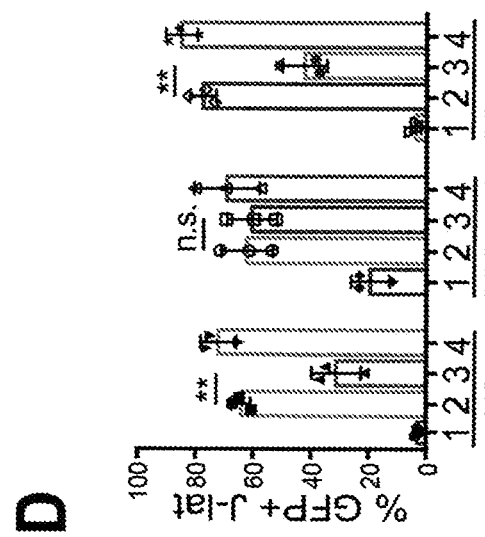

In addition to detection of GFP, we measured HIV transcription in these J-Lat cells to further verify the functional role of BRD4 (FIG. 5E). Consistent with the GFP results, ZL0580 can substantially inhibit Gag and 3'-LTR RNA expression in PMA-activated, VC J-Lat cells, which is largely abrogated in the BRD4-KO cells (FIG. 5E). A similar pattern was observed in the un-stimulated/resting J-Lat cells: while ZL0580 induced inhibition of basal HIV transcription (3'-LTR RNA on Day 7) as compared to NC and JQ1 treatment (FIG. 5F), such inhibitory effect was abrogated to large extent when BRD4 was knocked-out (FIG. 5F). Here, HIV transcription on Day 7 post treatment was chosen for comparison based on the earlier data that ZL0580 induces potent suppression of basal HIV transcription in un-stimulated J-Lat cells on this day (FIG. 1G).

Figure 5G:
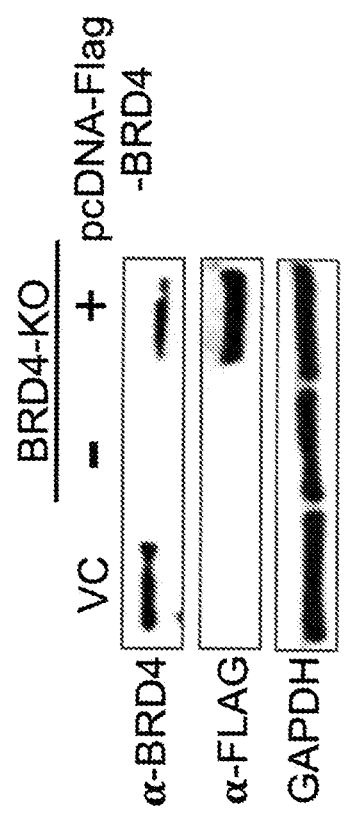
Figure 5H:
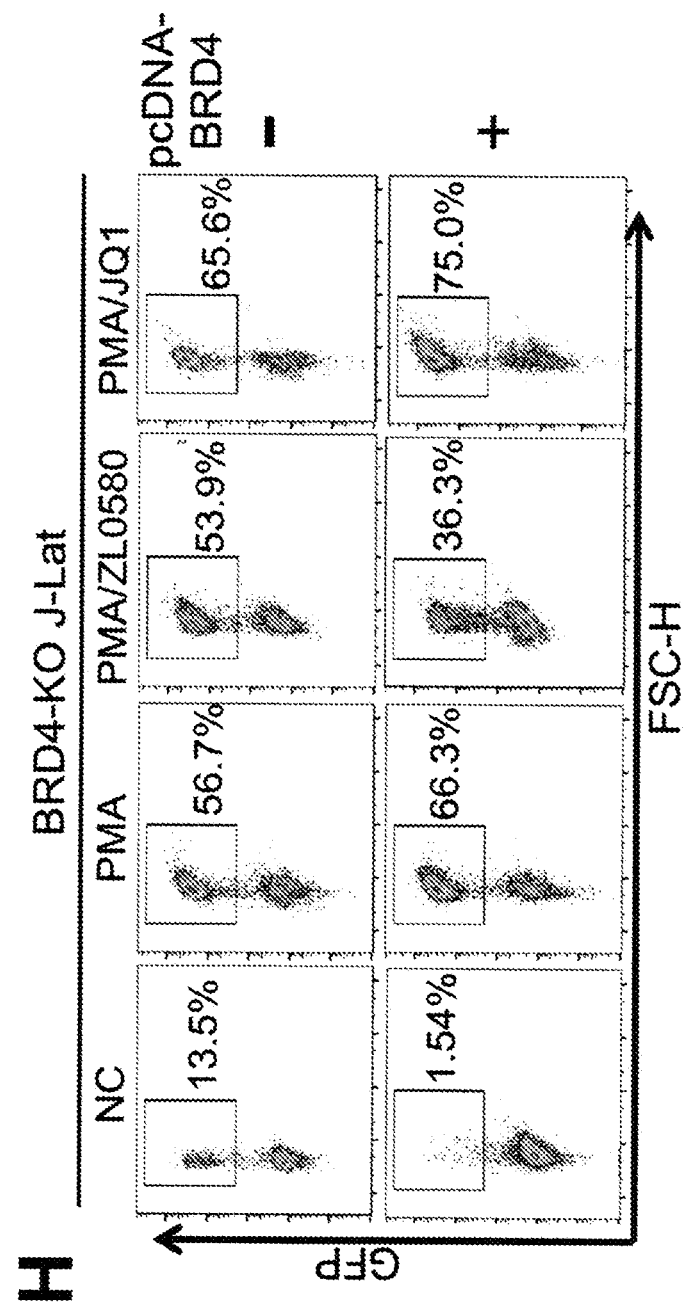
Figure 5I:
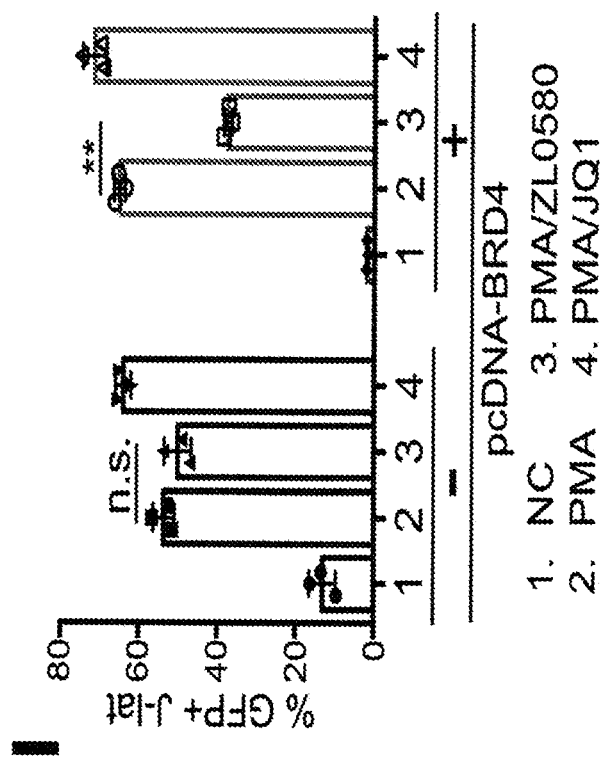

To further confirm that BRD4, instead of other BD-containing proteins (due to possible CRISPR/Cas9-induced off-target effects), is required in this process, exogenous BRD4 was over-expressed in the BRD4-KO cells by nucleofecting the cells with BRD4-encoding plasmid (pcDNA5-FLAG-BRD4; Addgene) (41). Efficient BRD4 expression was detected in the KO cells on Day 4 after nucleofection (FIG. 5G). Using an optimized protocol, nucleofection did not cause overt toxic effects to J-Lat cells. BRD4 over-expression was confirmed with both anti-BRD4 and anti-FLAG antibodies (FIG. 5G). We showed that while ZL0580 failed to induce HIV suppression in BRD4-KO cells (FIG. 5H-I), exogenous BRD4 expression restored to large extent the ability of ZL0580 to suppress HIV in these cells (FIG. 5H-I). This data provides additional evidence that ZL0580 induces HIV suppression via BRD4.

Figures 6A, 6B, 6C:
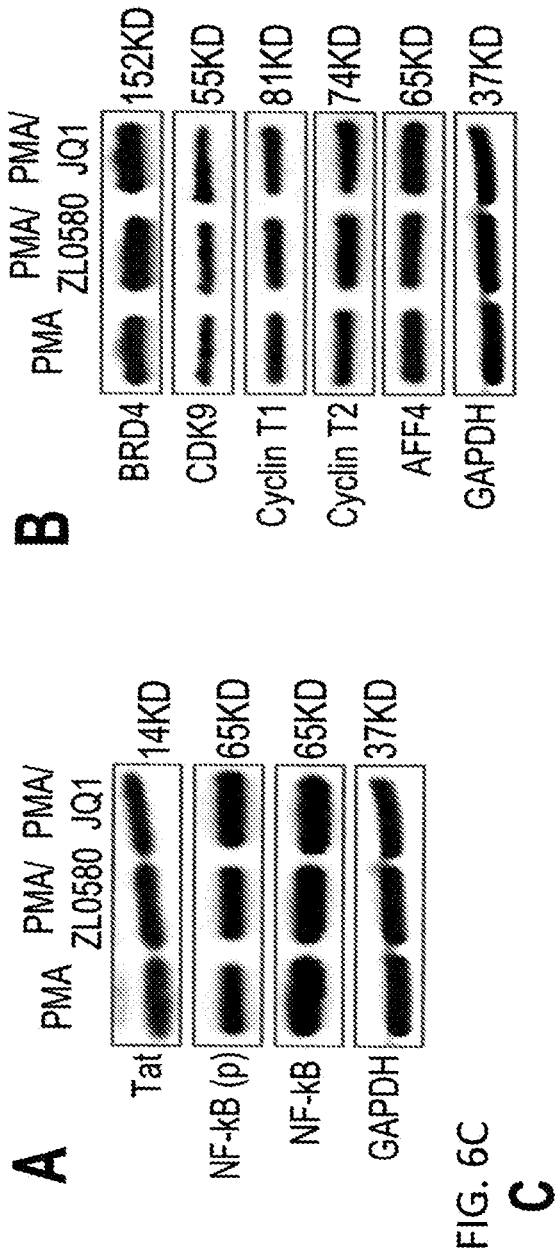

ZL0580 Inhibits Tat Transactivation and Key Factors in HIV Transcription Elongation After demonstrating functional requirement of BRD4 in ZL0580-induced HIV suppression, we next explored downstream biochemical mechanisms. We showed earlier (FIG. 1) that ZL0580 can suppress HIV in activated J-Lat cells at 24-hour after treatment. Based on this data, we first measured Tat protein expression to explore the stage(s) of HIV transcription inhibited by ZL0580. As compared to PMA alone or PMA+JQ1, treatment with PMA+ZL0580 did not significantly (or slightly) reduce Tat protein (FIG. 6A), indicating that ZL0580 may suppress HIV involving stage(s) post Tat synthesis, at least at the 24-hour time point after treatment. Consistent with this result, expression of NF-κB, which is important for HIV transcriptional initiation, was not affected by ZL0580 either (FIG. 6A).

Next, we explored mechanisms involved in Tat transactivation and transcription elongation. An established role of BRD4 is recruitment of cellular super elongation complex (SEC) (e.g. p-TEFb/CDK9) to target gene promoter, stimulating RNA Pol II (RNAPII) activation and transcription elongation (42). In HIV-infected cells, BRD4 competes with Tat for cellular reservoirs of CDK9, and negatively regulates HIV transcription elongation (30-32). First, we examined major proteins involved in HIV transcription elongation, including BRD4, CDK9, Cyclin T1/T2, and AFF4. Neither ZL0580 (PMA+ZL0580) nor JQ1 (PMA+JQ1) treatment altered expression of these proteins (FIG. 6B). However, Co-IP analysis of protein-protein interactions led to interesting findings. Tat Co-IP showed that compared to PMA alone, ZL0580 treatment (PMA+ZL0580) reduced CDK9 binding to Tat, whereas JQ1 enhanced CDK9 binding to Tat (FIG. 6C). This is not simply due to differential input Tat levels since they were comparable among different treatments (FIG. 6A). In contrast, BRD4 Co-IP revealed an opposing result: compared to PMA alone, ZL0580 induced enhanced CDK9 binding to BRD4, whereas JQ1 decreased CDK9 binding to BRD4 (FIG. 6C).

Figure 6D:
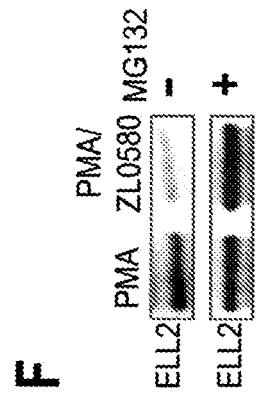
Figure 6E:
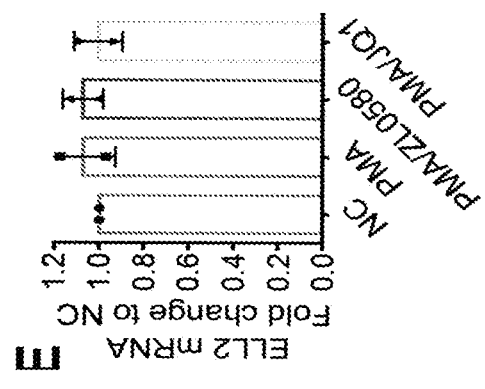
Figure 6F:
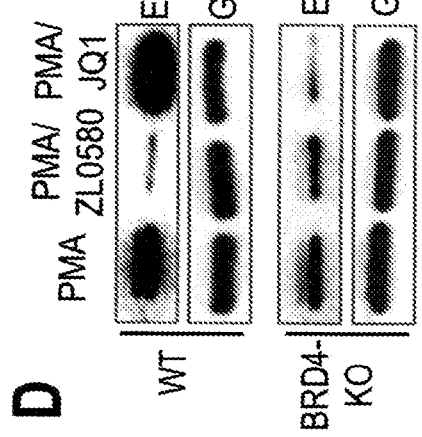

Like CDK9, ELL2 is another catalytic factor of SEC and is implicated in HIV transcriptional regulation (43). When measuring cellular proteins in these treated cells, we made an interesting observation that ZL0580 and JQ1 differentially regulated ELL2 protein. Compared to PMA alone, ZL0580 substantially reduced ELL2 protein, whereas JQ1 increased its level (FIG. 6D). Such distinct effects on ELL2 by ZL0580 and JQ1 were abrogated, to large extent, in BRD4-KO cells (FIG. 6D), supporting a functional role of BRD4 in mediating the regulatory effects of ZL0580 and JQ1 on HIV transcription. Further, we identified that ZL0580 inhibited ELL2 by reducing its protein stability, since ELL2 mRNA transcription was not altered by ZL0580 (FIG. 6E) and proteasome inhibition (by MG132) almost completely recovered ELL2 in ZL0580-treated cells (FIG. 6F). These data indicate that ZL0580 inhibits ELL2 via mechanisms involving post-translational degradation (44). Among the many proteins examined, only ELL2 was inhibited by ZL0580, indicating that this effect of ZL0580 on cellular proteins is likely selective for ELL2.

Figure 6G:
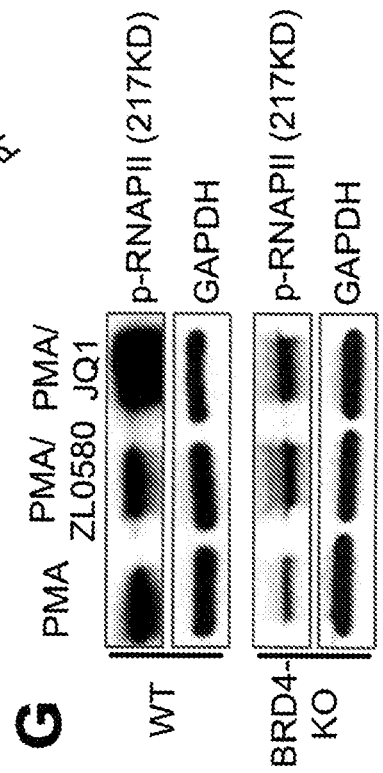

RNAPII activation is a rate-limiting step in transcription elongation (30, 31). Stimulation of RNAPII activation (phosphorylation of CTD Ser2 of RNAII) can be mediated by Tat-recruited SEC. We found that compared to PMA alone, ZL0580 reduced RNAII activation, whereas JQ1 potentiated its activation (FIG. 6G); notably, such differential effects on RNAPII activation were also abrogated to some extent when BRD4 was knocked out (FIG. 6G). This finding is consistent with the above observations of CDK9 binding to Tat or BRD4 (FIG. 6C) and the effects on ELL2 protein levels by ZL0580 and JQ1 (FIG. 6D-F), providing evidence that distinct from JQ1, ZL0580 induces inhibition of key factors in HIV transcription elongation.

Figure 6H:
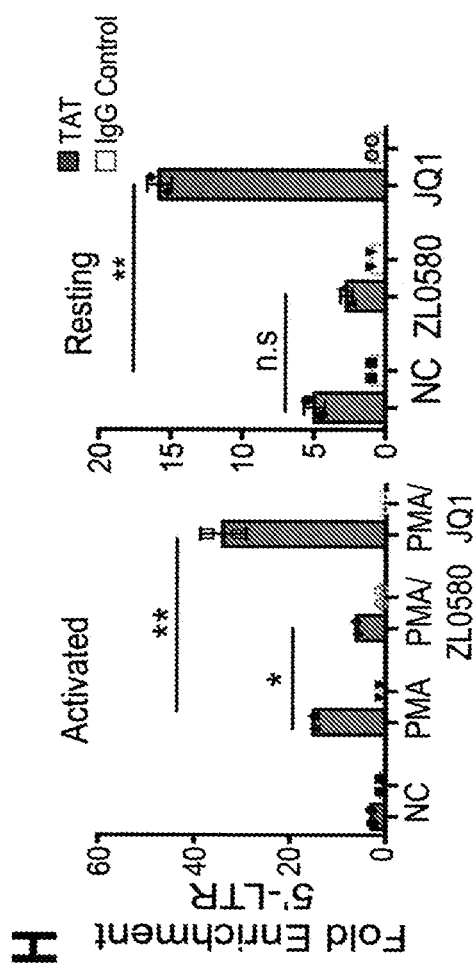
Figure 6I:
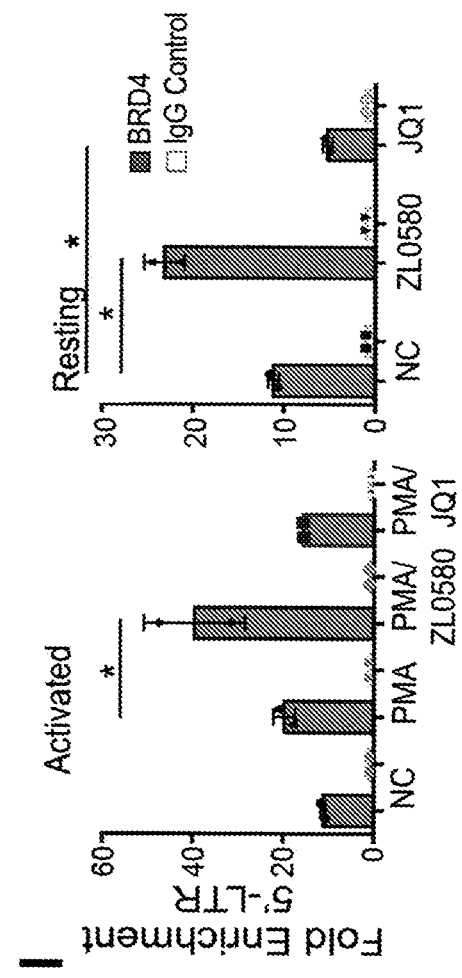

To directly examine the impact of ZL0580 on Tat transactivation, we measured recruitment of Tat to HIV promoter (a small region overlapping with HIV transcription start site) (31) by CHIP-qPCR and observed that while JQ1 enhanced binding of Tat to HIV promoter, ZL0580 reduced Tat recruitment to HIV promoter (FIG. 6H). As a control, no Tat recruitment to GAPDH promoter was detected. A similar pattern for Tat binding to HIV promoter was also observed in un-stimulated J-Lat cells (FIG. 6H). These data support that inhibition of Tat transactivation may represent a mechanism by which ZL0580 induces HIV suppression. Moreover, we measured BRD4 binding to HIV promoter in these treated cells. Of interest, BRD4 displayed a binding pattern distinct from Tat in both activated and resting J-Lat cells: compared to no compound control, ZL0580 promoted BRD4 binding to HIV promoter, whereas JQ1 reduced this binding (FIG. 6I), indicating that BRD4 may completely block or reduce Tat transactivation following ZL0580 treatment.

ZL0580 Induces a More Repressive Chromatin Structure in HIV LTR

Figure 7B:
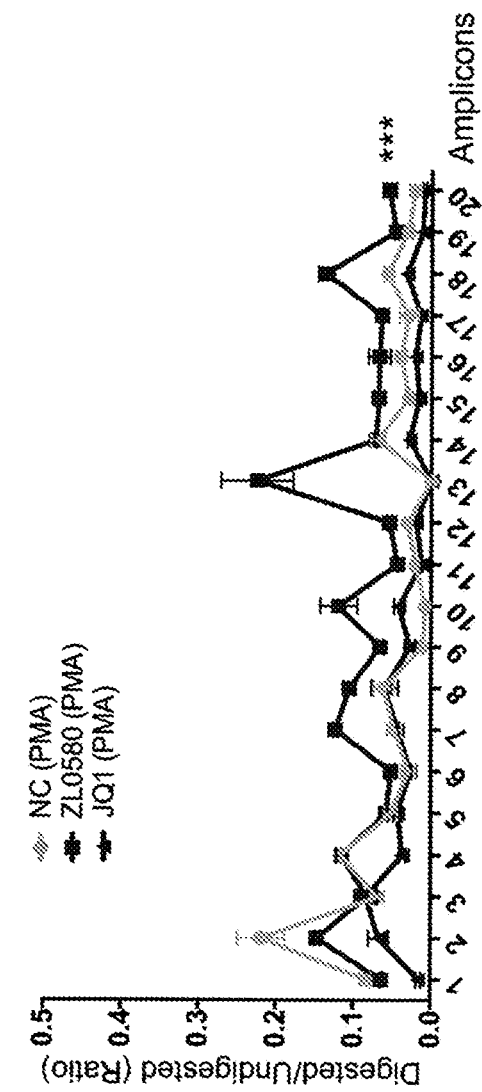

Nucleosome organization and structure in HIV LTR correlates with HIV proviral transcription (45). Positioning of a nucleosome (nuc-1) downstream of HIV transcription start site (TSS) restricts HIV transcription (FIG. 7A) (45). To this end, we have observed that in addition to induced HIV transcription in the activated cells, ZL0580 also induced suppression of basal and latent HIV in un-stimulated cells, where HIV underwent low-level transcription and Tat protein was considered low. We therefore speculate that mechanisms beyond Tat-mediated transcription may also play a role in ZL0580-induced HIV suppression. We examined effects of ZL0580 on nucleosome organization and DNA accessibility in HIV LTR, using the high-resolution MNase nucleosomal mapping (45). J-Lat cells were pre-treated with ZL0580, JQ1, or not (NC) for 24 hours, followed by PMA activation for 24 hours. Chromatin isolated from cells were divided into undigested and MNase digested samples. Digested and undigested DNA samples were probed with 20 separate sets of overlapping primers to amplify different regions along the HIV LTR (FIG. 7A) (45). The principle is that DNA within nucleosomes will be protected (at least partially) from MNase digestion, whereas nucleosome-free and linker DNAs will be cleaved. Accordingly, the ratio for PCR product in digested DNA to that of undigested control can be used to assess nucleosomal occupancy and DNA accessibility. We found that compared to the no compound treatment control (NC), treatment with ZL0580 led to enhanced nucleosomal DNA protection in the majority of amplicon regions (6-20), especially in the amplicon 13 that covers Nuc-1 immediately downstream of TSS (FIG. 7B). In contrast, compared to NC, treatment of J-Lat cells with JQ1 reduced nucleosomal DNA protection in several amplicon regions, although the effect of JQ1 appeared to be only modest (FIG. 7B). This data indicates that JQ1 may cause a less repressive nucleosomal structure in the HIV LTR, consistent with a recent report (29). These data altogether suggest that ZL0580 induces chromatin remodeling and causes a more repressive nucleosomal structure in the HIV LTR.

Example 2

ZL0580 Synthesis (4-Nitrophenyl)sulfonyl)-L-proline (2) (Also Referred to as ZL0571)

To a solution of methyl ((4-nitrophenyl)sulfonyl)-L-prolinate (1) (500 mg, 1.6 mmol) in 16 mL CH$_3$OH, LiOH.H$_2$O (334 mg, 8.0 mmol) in 8 mL H$_2$O was added. The mixture was allowed to stir at room temperature for 4 hours. After concentration, the solution was acidified by 10% HCl to pH=3 and extracted by dichloromethane (DCM) to obtain 2 (540 mg, quant.) as a white solid. The crude product was used directly in the next step.

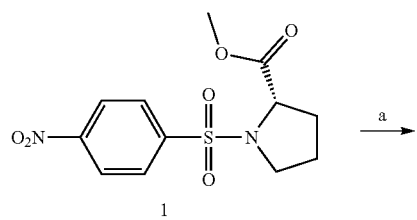

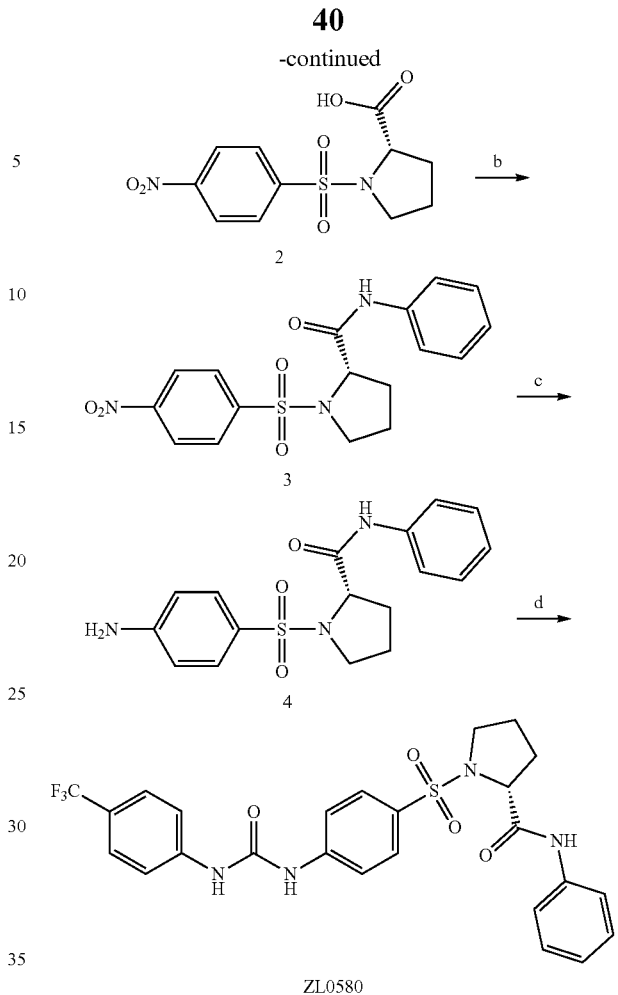

ZL0580

Reagents and conditions: (a) LiOH, CH$_3$OH/H$_2$O, rt., 4 h, quant.; (b) aniline, HBTU, DIEA, DCM, rt., 66%; (c) Zn, NH$_4$Cl, EtOH/H$_2$O, reflux; (d) 1-isocyanato-4-(trifluoromethyl)benzene, DCM, rt., 66% for two steps.

(S)-1-((4-Nitrophenyl) sulfonyl)-N-phenylpyrrolidine-2-carboxamide (3) (Also Referred to as ZL0573)

To a solution of 2 (100 mg, 0.33 mmol) and aniline (31 mg, 0.33 mmol) in 5 mL of DCM, HBTU (321 mg, 1.0 mmol) and DIPEA (295 µL, 1.67 mmol) were added. After stirring at rt. overnight, the mixture was extracted with DCM (20 mL×3). The organic layer was washed with 1 N NaHSO$_4$ (aq.), saturated NaHCO$_3$ (aq.), brine and dried over anhydrous Na$_2$SO$_4$. The resulting solution was evaporated, and the residue was purified by PTLC (DCM/MeOH=70:1) to give the desired product 3 (81 mg, 66%) as a pale yellow solid. $^1$H NMR (300 MHz, CDCl$_3$) δ 8.35 (d, J=8.7 Hz, 2H), 8.05 (d, J=8.7 Hz, 2H), 7.52 (d, J=8.0 Hz, 2H), 7.37-7.25 (m, 2H), 7.11 (t, J=7.4 Hz, 1H), 4.32-4.18 (m, 1H), 3.68-3.56 (m, 1H), 3.29 (dd, J=16.8, 7.8 Hz, 1H), 2.31-2.18 (m, 1H), 1.98-1.86 (m, 1H), 1.84-1.68 (m, 2H). $^{13}$C NMR (75 MHz, CDCl$_3$) δ 168.94, 150.48, 141.93, 137.12, 129.04, 128.97, 124.85, 124.55, 120.20, 120.10, 62.91, 49.85, 30.36, 24.49.

(S)-1-((4-Aminophenyl)sulfonyl)-N-phenylpyrrolidine-2-carboxamide (4) (Also Referred to as ZL0576)

To a solution of 3 (70 mg, 0.19 mmol) in 10 mL CH$_3$CH$_2$OH, NH$_4$Cl (50 mg, 0.93 mmol) in 3 mL H$_2$O and Zn dust (123 mg, 1.9 mmol) were added. The solution was allowed to reflux for 0.5 hour. Then it was filtered, and the filtrate was extracted by DCM for three times. The organic layer was dried and concentrated to give 4 as a white foam which was used directly in the next step.

(R)—N-Phenyl-1-((4-(3-(4-(trifluoromethyl)phenyl)ureido)phenyl)sulfonyl)pyrrolidine-2-carboxamide (ZL0580)

To a solution of 4 (0.187 mmol) in 5 mL DCM, 1-isocyanato-4-(trifluoromethyl)benzene (37 mg, 0.2 mmol) was added. After stirring at rt. overnight, the mixture was concentrated and purified by PTLC (DCM/CH$_3$OH=50:1) to give ZL0580 (65 mg, 66% for two steps) as a white solid. HPLC purity 99.8% ($t_R$=19.7 min). $^1$H NMR (300 MHz, MeOD) δ 7.87 (d, J=8.8 Hz, 2H), 7.74 (d, J=8.6 Hz, 2H), 7.68 (d, J=8.7 Hz, 2H), 7.64-7.55 (m, 4H), 7.35 (t, J=7.7 Hz, 2H), 7.14 (t, J=7.3 Hz, 1H), 4.24 (dd, J=7.7, 4.2 Hz, 1H), 3.70-3.57 (m, 1H), 3.38 (d, J=7.6 Hz, 1H), 2.13-1.91 (m, 3H), 1.69 (d, J=5.3 Hz, 1H). $^{13}$C NMR (75 MHz, MeOD) δ 171.43, 152.67, 144.19, 142.52, 137.74, 129.56, 128.81, 128.42, 125.75, 125.70, 124.32, 120.44, 118.35, 118.21, 62.61, 49.37, 30.83, 24.31. HR ESI-MS (M+Na)$^+$ m/z=555.1282 (calcd for C$_{25}$H$_{24}$F$_3$N$_4$O$_4$SNa: 555.1290).

(S)-1-Methyl-4-(((4-nitrophenyl)sulfonyl)prolyl)piperazine (ZL0574)

ZL0574 (106 mg, 84 mg) was obtained as a yellow solid followed the procedure of ZL0573. $^1$H NMR (300 MHz, CDCl$_3$) δ 8.25 (d, J=8.5 Hz, 2H), 8.00 (d, J=8.5 Hz, 2H), 4.84 (dd, J=8.1, 3.2 Hz, 1H), 3.47 (dd, J=18.7, 10.5 Hz, 5H), 3.32 (dd, J=13.8, 8.0 Hz, 1H), 2.46-2.26 (m, 4H), 2.19-2.08 (m, 1H), 2.04-1.79 (m, 3H). $^{13}$C NMR (75 MHz, CDCl$_3$) δ 169.10, 149.80, 145.16, 128.72, 123.88, 58.54, 54.94, 54.59, 48.13, 45.91, 45.45, 42.06, 30.91, 24.76.

(S)-1-(((4-Aminophenyl)sulfonyl)prolyl)-4-methylpiperazine (ZL0578)

ZL0578 was obtained following the procedure of ZL0576. $^1$H NMR (300 MHz, CDCl$_3$) δ 7.61 (d, J=8.5 Hz, 2H), 6.67 (d, J=8.6 Hz, 2H), 4.61 (dd, J=7.5, 4.8 Hz, 1H), 4.37 (s, 1H), 3.67 (dd, J=15.7, 10.0 Hz, 4H), 3.37 (dd, J=10.9, 6.1 Hz, 2H), 2.53 (d, J=23.4 Hz, 4H), 2.36 (s, 3H), 2.07-1.84 (m, 3H).

(R)-1-(4-((2-(4-Methylpiperazine-1-carbonyl)pyrrolidin-1-yl)sulfonyl)phenyl)-3-(4-(trifluoromethyl)phenyl)urea (ZL0581)

ZL0581 (76 mg, 60% for two steps) was obtained following the procedure of ZL0580. HPLC purity 90.0% ($t_R$=17.10 min). $^1$H NMR (300 MHz, MeOD) δ 7.82 (d, J=8.7 Hz, 2H), 7.69 (dd, J=11.7, 8.9 Hz, 4H), 7.59 (d, J=8.5 Hz, 2H), 4.70 (dd, J=7.9, 4.7 Hz, 1H), 3.79-3.41 (m, 6H), 2.47 (d, J=20.7 Hz, 4H), 2.32 (s, 3H), 2.05 (dd, J=11.2, 7.8 Hz, 1H), 1.94 (dd, J=12.4, 6.3 Hz, 1H), 1.88-1.77 (m, 1H), 1.64 (dt, J=12.3, 6.2 Hz, 1H). $^{13}$C NMR (75 MHz, MeOD) δ 171.14, 152.63, 143.83, 142.59, 131.00, 129.35, 128.55, 125.81, 125.76, 125.71, 125.66, 118.35, 118.21, 113.12, 58.36, 54.48, 54.03, 48.50, 44.88, 44.57, 41.70, 30.59, 24.42. MS (M+H)$^+$ m/z 540.1. HR ESI-MS (M+H)$^+$ m/z=540.1882 (calcd for C$_{24}$H$_{29}$F$_3$N$_5$O$_4$S: 540.1892).

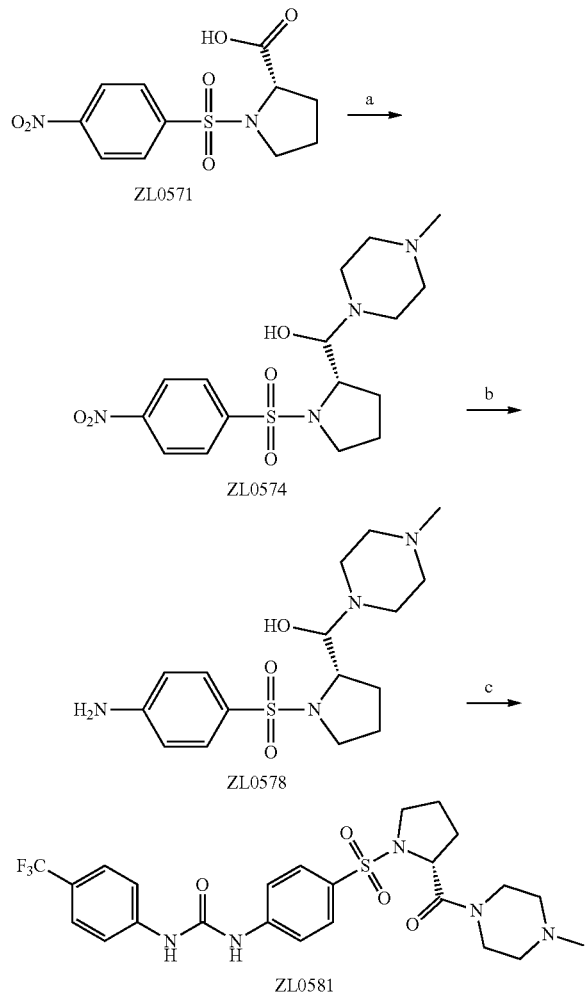

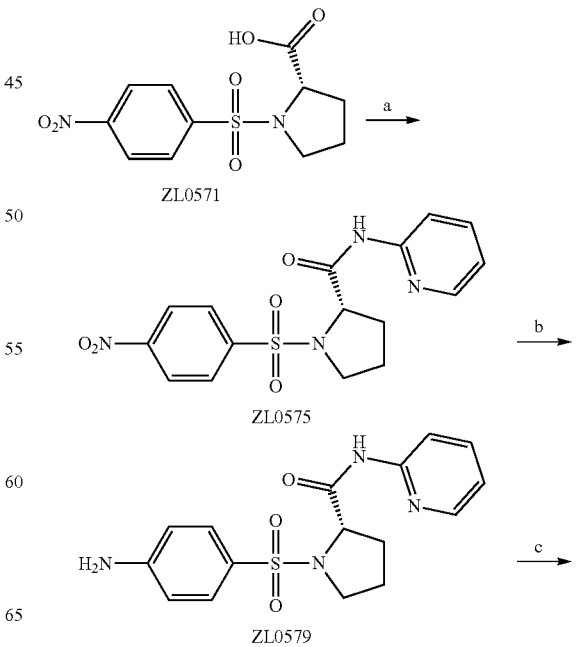

Reagents and conditions: (a) 1-methylpiperazine, HBTU, DIEA, DCM, rt, 84%; (b) Zn, NH$_4$Cl, EtOH/H$_2$O, reflux; (c) 1-isocyanato-4-(trifluoromethyl)benzene, DCM, rt, 60% for two steps.

-continued

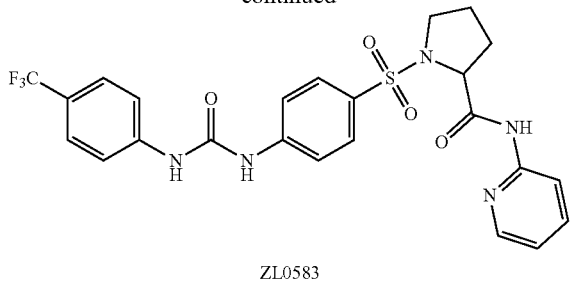

ZL0583

Reagents and conditions: (a) 1-methylpiperazine, HBTU, DIEA, DCM, rt, 69%; (b) Zn, NH$_4$Cl, EtOH/H$_2$O, reflux; (c) 1-isocyanato-4-(trifluoromethyl)benzene, DCM, rt, 17% for two steps.

(S)-1-((4-Nitrophenyl)sulfonyl)-N-(pyridin-2-yl) pyrrolidine-2-carboxamide (ZL0575)

ZL0575 (85 mg, 69%) was obtained as a white foam following the procedure of ZL0573. $^1$H NMR (300 MHz, CDCl$_3$) δ 9.15 (s, 1H), 8.36 (d, J=8.4 Hz, 2H), 8.28 (d, J=4.1 Hz, 1H), 8.11 (dd, J=14.0, 8.6 Hz, 3H), 7.69 (t, J=7.6 Hz, 1H), 7.12-6.99 (m, 1H), 4.31 (d, J=4.8 Hz, 1H), 3.64 (s, 1H), 3.32 (dd, J=16.0, 7.7 Hz, 1H), 2.23 (d, J=7.9 Hz, 1H), 1.89 (t, J=18.4 Hz, 2H), 1.77 (dd, J=10.7, 4.2 Hz, 1H). $^{13}$C NMR (75 MHz, CDCl$_3$) δ 169.40, 150.72, 150.46, 148.01, 142.09, 138.40, 129.12, 124.58, 120.36, 113.98, 63.06, 49.88, 30.64, 24.58.

(S)-1-((4-Aminophenyl)sulfonyl)-N-(pyridin-2-yl) pyrrolidine-2-carboxamide (ZL0579)

ZL0579 was obtained following the procedure of ZL0576.

(R)—N-(Pyridin-2-yl)-1-((4-(3-(4-(trifluoromethyl) phenyl)ureido)phenyl)sulfonyl) pyrrolidine-2-carboxamide (ZL0583)

ZL0583 (20 mg, 17% for two steps) was obtained as a white solid following the procedure of ZL0580. HPLC purity 96.5% (t$_R$=19.39 min). $^1$H NMR (300 MHz, MeOD) δ 8.32 (d, J=4.2 Hz, 1H), 8.15 (d, J=8.3 Hz, 1H), 7.87 (d, J=8.8 Hz, 2H), 7.84-7.77 (m, 1H), 7.74 (d, J=8.8 Hz, 2H), 7.68 (d, J=8.7 Hz, 2H), 7.60 (d, J=8.8 Hz, 2H), 7.15 (dd, J=7.0, 5.1 Hz, 1H), 4.32 (dd, J=7.9, 4.0 Hz, 1H), 3.68-3.58 (m, 1H), 3.39-3.33 (m, 1H), 2.15-2.03 (m, 1H), 1.98-1.84 (m, 2H), 1.68 (dd, J=11.0, 5.4 Hz, 1H). $^{13}$C NMR (75 MHz, MeOD) δ 171.46, 152.61, 151.00, 147.65, 144.26, 142.53, 138.37, 129.26, 128.91, 125.79, 125.74, 125.69, 125.64, 120.03, 118.35, 118.24, 114.05, 62.70, 49.44, 30.51, 24.28. ESI-MS (M+H)$^+$ m/z 534.1. HR ESI-MS (M+H)$^+$ m/z=534.1414 (calcd for C$_{24}$H$_{23}$F$_3$N$_5$O$_4$S: 534.1423)

Example 3

Compound Binding Analysis (TR-FRET)

384 well plate-based commercial TR-FRET Assay kits (Cayman Chemical, Ann Arbor, Mich.) were used to determine the binding affinity of ZL0580 to the bromodomains (BDs) of BRD4, BRD2, BRD3, and BRDT as well as CBP by time-resolved fluorescence energy transfer (TR-FRET) assays. A series of concentrations of the compound from 0.01 nM to 100 μM were added into a 384 well test plate and mixed with other reaction components based on the instructions from vendor followed by incubation 1 h at room temperature. The commercially available BET inhibitor JQ1 was used as the control. The plates were read in time-resolved format by exciting the sample at 340 nm and reading emissions at 620 and 670 nm, using a 100 μs delay and a 500 μs window at a Tecan M1000 pro reader. A plot of the TR-FRET ratio (670 nm emission/620 nm emission versus inhibitor concentration on semi-log axes results in a sigmoidal dose-response curve typical of competitive assays. These data were further calculated out with the IC$_{50}$ values of the tested compounds to the bromodomains. IC$_{50}$ values are reported as the mean derived from three independent measurements. Each one is generated from at least 8 different concentrations.

It is to be understood that both the foregoing general description of the invention and the following detailed description are exemplary, and thus do not restrict the scope of the invention.

All publications mentioned herein are incorporated by reference to the extent they support the present invention.

REFERENCES

1. Dahabieh M S, Battivelli E, and Verdin E. Understanding HIV latency: the road to an HIV cure. Annu Rev Med. 2015; 66(407-21.
2. Ruelas D S, and Greene W C. An integrated overview of HIV-1 latency. Cell. 2013; 155(3):519-29.
3. Siliciano R F, and Greene W C. HIV latency. Cold Spring Harb Perspect Med. 2011; 1(1):a007096.
4. Chun T W, Moir S, and Fauci A S. HIV reservoirs as obstacles and opportunities for an HIV cure. Nat Immunol. 2015; 16(6):584-9.
5. Sedaghat A R, Siliciano R F, and Wilke C O. Low-level HIV-1 replication and the dynamics of the resting CD4+ T cell reservoir for HIV-1 in the setting of HAART. BMC Infect Dis. 2008; 8(2.
6. Marin B, Thiebaut R, Bucher H C, Rondeau V, Costagliola D, Dorrucci M, Hamouda O, Prins M, Walker S, Porter K, et al. Non-AIDS-defining deaths and immunodeficiency in the era of combination antiretroviral therapy. AIDS. 2009; 23(13):1743-53.
7. International ASSWGoHIVC, Deeks S G, Autran B, Berkhout B, Benkirane M, Cairns S, Chomont N, Chun T W, Churchill M, Di Mascio M, et al. Towards an HIV cure: a global scientific strategy. Nat Rev Immunol. 2012; 12(8):607-14.
8. Archin N M, and Margolis D M. Emerging strategies to deplete the HIV reservoir. Curr Opin Infect Dis. 2014; 27(1):29-35.
9. Deeks S G. HIV: Shock and kill. Nature. 2012; 487(7408): 439-40.
10. Archin N M, Liberty A L, Kashuba A D, Choudhary S K, Kuruc J D, Crooks A M, Parker D C, Anderson E M, Kearney M F, Strain M C, et al. Administration of vorinostat disrupts HIV-1 latency in patients on antiretroviral therapy. Nature. 2012; 487(7408):482-5.
11. Bullen C K, Laird G M, Durand C M, Siliciano J D, and Siliciano R F. New ex vivo approaches distinguish effective and ineffective single agents for reversing HIV-1 latency in vivo. Nat Med. 2014; 20(4):425-9.
12. Ho Y C, Shan L, Hosmane N N, Wang J, Laskey S B, Rosenbloom D I, Lai J, Blankson J N, Siliciano J D, and Siliciano R F. Replication-competent noninduced proviruses in the latent reservoir increase barrier to HIV-1 cure. Cell. 2013; 155(3):540-51.

13. Darcis G, Van Driessche B, and Van Lint C. HIV Latency: Should We Shock or Lock? Trends Immunol. 2017; 38(3):217-28.
14. Liu C, Ma X, Liu B, Chen C, and Zhang H. HIV-1 functional cure: will the dream come true? BMC Med. 2015; 13(284.
15. Mbonye U, and Karn J. Transcriptional control of HIV latency: cellular signaling pathways, epigenetics, happenstance and the hope for a cure. Virology. 2014; 454-455 (328-39.
16. Hakre S, Chavez L, Shirakawa K, and Verdin E. Epigenetic regulation of HIV latency. Curr Opin HIV AIDS. 2011; 6(1): 19-24.
17. Mbonye U, and Karn J. Control of HIV latency by epigenetic and non-epigenetic mechanisms. Curr HIV Res. 2011; 9(8):554-67.
18. Belkina A C, and Denis G V. BET domain co-regulators in obesity, inflammation and cancer. Nat Rev Cancer. 2012; 12(7):465-77.
19. Zhu J, Gaiha G D, John S P, Pertel T, Chin C R, Gao G, Qu H, Walker B D, Elledge S J, and Brass A L. Reactivation of latent HIV-1 by inhibition of BRD4. Cell Rep. 2012; 2(4):807-16.
20. Li Z, Guo J, Wu Y, and Zhou Q. The BET bromodomain inhibitor JQ1 activates HIV latency through antagonizing Brd4 inhibition of Tat-transactivation. Nucleic Acids Res. 2013; 41(1):277-87.
21. Conrad R J, Fozouni P, Thomas S, Sy H, Zhang Q, Zhou M M, and Ott M. The Short Isoform of BRD4 Promotes HIV-1 Latency by Engaging Repressive SWI/SNF Chromatin-Remodeling Complexes. Mol Cell. 2017; 67(6): 1001-12 e6.
22. Liu Z, Wang P, Chen H, Wold E A, Tian B, Brasier A R, and Zhou J. Drug Discovery Targeting Bromodomain-Containing Protein 4. J Med Chem. 2017; 60(11):4533-58.
23. Spina C A, Anderson J, Archin N M, Bosque A, Chan J, Famiglietti M, Greene W C, Kashuba A, Lewin S R, Margolis D M, et al. An in-depth comparison of latent HIV-1 reactivation in multiple cell model systems and resting CD4+ T cells from aviremic patients. PLoS Pathog. 2013; 9(12):e1003834.
24. Baell J, and Walters M A. Chemistry: Chemical con artists foil drug discovery. Nature. 2014; 513(7519):481-3.
25. Liu F, Fan X, Auclair S, Ferguson M, Sun J, Soong L, Hou W, Redfield R R, Birx D L, Ratto-Kim S, et al. Sequential Dysfunction and Progressive Depletion of *Candida albicans*-Specific CD4 T Cell Response in HIV-1 Infection. PLoS Pathog. 2016; 12(6):e1005663.
26. Padmanabhan B, Mathur S, Manjula R, and Tripathi S. Bromodomain and extra-terminal (BET) family proteins: New therapeutic targets in major diseases. J Biosci. 2016; 41(2):295-311.
27. Boehm D, Calvanese V, Dar R D, Xing S, Schroeder S, Martins L, Aull K, Li P C, Planelles V, Bradner J E, et al. Cell Cycle. 2013; 12(3):452-62.
28. Bisgrove D A, Mahmoudi T, Henklein P, and Verdin E. Conserved P-TEFb-interacting domain of BRD4 inhibits HIV transcription. Proc Natl Acad Sci USA. 2007; 104 (34):13690-5.
29. Ma C T, and Sergienko E A. Time-Resolved Fluorescence Assays. Methods Mol Biol. 2016; 1439(131-42.
30. Boehm D, Calvanese V, Dar R D, Xing S, Schroeder S, Martins L, Aull K, Li P C, Planelles V, Bradner J E, et al. BET bromodomain-targeting compounds reactivate HIV from latency via a Tat-independent mechanism. Cell Cycle. 2013; 12(3):452-62.
31. Wu S Y, and Chiang C M. The double bromodomain-containing chromatin adaptor Brd4 and transcriptional regulation. J Biol Chem. 2007; 282(18):13141-5.
32. Vollmuth F, Blankenfeldt W, and Geyer M. Structures of the dual bromodomains of the P-TEFb-activating protein Brd4 at atomic resolution. J Biol Chem. 2009; 284(52): 36547-56.
33. Luo Z, Lin C, and Shilatifard A. The super elongation complex (SEC) family in transcriptional control. Nat Rev Mol Cell Biol. 2012; 13(9):543-7.
34. Dhalluin C, Carlson J E, Zeng L, He C, Aggarwal A K, and Zhou M M. Structure and ligand of a histone acetyltransferase bromodomain. Nature. 1999; 399(6735):491-6.
35. Filippakopoulos P, Picaud S, Mangos M, Keates T, Lambert J P, Barsyte-Lovejoy D, Felletar I, Volkmer R, Muller S, Pawson T, et al. Histone recognition and large-scale structural analysis of the human bromodomain family. Cell. 2012; 149(1):214-31.
36. Jiang Y W, Veschambre P, Erdjument-Bromage H, Tempst P, Conaway J W, Conaway R C, and Kornberg R D. Mammalian mediator of transcriptional regulation and its possible role as an end-point of signal transduction pathways. Proc Natl Acad Sci USA. 1998; 95(15):8538-43.
37. Yang Z, Yik J H, Chen R, He N, Jang M K, Ozato K, and Zhou Q. Recruitment of P-TEFb for stimulation of transcriptional elongation by the bromodomain protein Brd4. Mol Cell. 2005; 19(4):535-45.
38. Jang M K, Mochizuki K, Zhou M, Jeong H S, Brady J N, and Ozato K. The bromodomain protein Brd4 is a positive regulatory component of P-TEFb and stimulates RNA polymerase II-dependent transcription. Mol Cell. 2005; 19(4):523-34.
39. Huang B, Yang X D, Zhou M M, Ozato K, and Chen L F. Brd4 coactivates transcriptional activation of NF-kappaB via specific binding to acetylated RelA. Mol Cell Biol. 2009; 29(5):1375-87.
40. Kao S Y, Calman A F, Luciw P A, and Peterlin B M. Anti-termination of transcription within the long terminal repeat of HIV-1 by tat gene product. Nature. 1987; 330(6147):489-93.
41. Ott M, Geyer M, and Zhou Q. The control of HIV transcription: keeping RNA polymerase II on track. Cell Host Microbe. 2011; 10(5):426-35.
42. Zhou Q, Li T, and Price D H. RNA polymerase II elongation control. Annu Rev Biochem. 2012; 81(119-43.
43. He N, Liu M, Hsu J, Xue Y, Chou S, Burlingame A, Krogan N J, Alber T, and Zhou Q. HIV-1 Tat and host AFF4 recruit two transcription elongation factors into a bifunctional complex for coordinated activation of HIV-1 transcription. Mol Cell. 2010; 38(3):428-38.
44. Sobhian B, Laguette N, Yatim A, Nakamura M, Levy Y, Kiernan R, and Benkirane M. HIV-1 Tat assembles a multifunctional transcription elongation complex and stably associates with the 7SK snRNP. Mol Cell. 2010; 38(3):439-51.
45. Liu M, Hsu J, Chan C, Li Z, and Zhou Q. The ubiquitin ligase Siah1 controls ELL2 stability and formation of super elongation complexes to modulate gene transcription. Mol Cell. 2012; 46(3):325-34.
46. Logan M M, Toma T, Thomas-Tran R, and Du Bois J. Asymmetric synthesis of batrachotoxin: Enantiomeric toxins show functional divergence against NaV. Science. 2016; 354(6314):865-9.
47. Hu H, Eller M A, Zafar S, Zhou Y, Gu M, Wei Z, Currier J R, Marovich M A, Kibuuka H N, Bailer R T, et al. Preferential infection of human Ad5-specific CD4 T cells by HIV in Ad5 naturally exposed and recombinant Ad5-HIV vaccinated individuals. Proc Natl Acad Sci USA. 2014; 111(37):13439-44.

48. Liu F, Niu Q, Fan X, Liu C, Zhang J, Wei Z, Hou W, Kanneganti T D, Robb M L, Kim J H, et al. Priming and Activation of Inflammasome by Canarypox Virus Vector ALVAC via the cGAS/IFI16-STING-Type I IFN Pathway and AIM2 Sensor. J Immunol. 2017; 199(9):3293-305.

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

We claim:

1. A compound, or a pharmaceutically acceptable salt thereof, having the formula:

Formula I

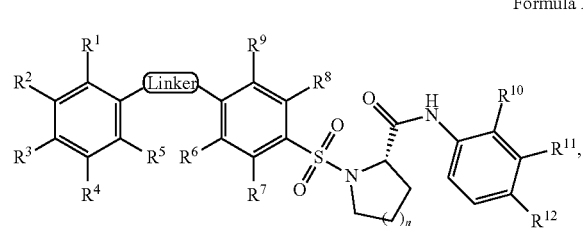

wherein
$R^1$, $R^2$, $R^3$, $R^4$, $R^5$, $R^6$, $R^7$, $R^8$ and $R^9$ are independently H, —OH, alkyl, alkoxy, halogen, $NH_2$, —$OCF_3$ or —$CF_3$;
$R^{10}$, $R^{11}$ and $R^{12}$ are independently H, —OH, halogen, alkoxy, —$NH_2$, —$CF_3$, —(CO)$R^{13}$, where $R^{13}$ is alkyl, alkoxy, amino, or alkylamino; —$NR^{22}R^{23}$ where $R^{22}$ and $R^{23}$ are independently H, alkyl; or $R^{22}$ and $R^{23}$ are optionally joined to form a 3-6 membered substituted or unsubstituted heterocycle having 1-3 heteroatoms;
Linker is —(CO)$NR_{25}$—, $NR^{26}$ or —$R^{27}$(CO)—, wherein $R^{25}$, $R^{26}$ and $R^{27}$ are independently H or $C_1$-$C_6$ alkyl; and
n is 0-3.

2. A compound, or a pharmaceutically acceptable salt thereof, having

Formula III

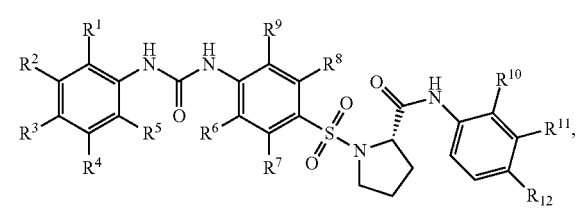

the formula:
wherein
$R^1$, $R^2$, $R^3$, $R^4$, $R^5$, $R^6$, $R^7$, $R^8$ and $R^9$ are independently H, —OH, alkyl, alkoxy, halogen, —$NH_2$, —$OCF_3$ or —$CF_3$;
$R^{10}$, $R^{11}$ and $R^{12}$ are independently H, —OH, halogen, alkoxy, —$NH_2$, —$CF_3$, —(CO)$R^{13}$ where $R^{13}$ is alkyl, alkoxy, amino, or alkylamino; —$NR^{22}R^{23}$ where $R^{22}$ and $R^{23}$ are independently H, alkyl; or $R^{22}$ and $R^{23}$ are optionally joined to form a 3-6 membered substituted or unsubstituted heterocycle having 1-3 heteroatoms.

3. The compound of claim 2, where $R^1$, $R^2$, $R^4$, $R^5$, $R^6$, $R^7$, $R^8$, $R^9$, $R^{10}$ and $R^{11}$ are H and $R^3$ is —$CF_3$ or alkoxy:

Formula IV

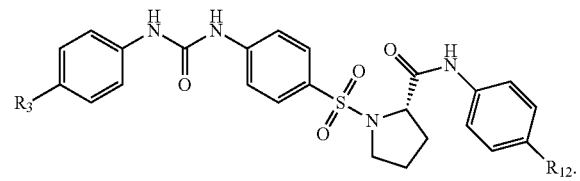

4. The compound according to claim 2, where the compound is:

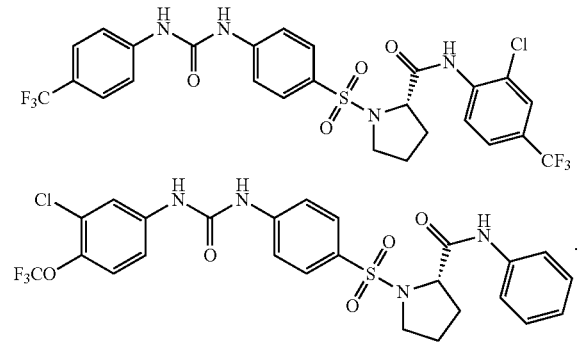

5. A compound, or a pharmaceutically acceptable salt thereof, having the formula:

Formula Ia

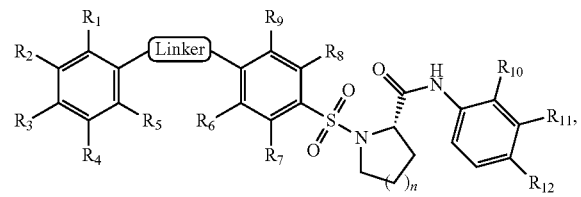

wherein
$R^1$, $R^2$, $R^3$, $R^4$, $R^5$, $R^6$, $R^7$, $R^8$ and $R^9$ are independently H, —OH, alkyl, alkoxy, halogen, $NH_2$, —$OCF_3$ or —$CF_3$;
$R^{10}$, $R^{11}$ and $R^{12}$ are independently H, —OH, halogen, alkoxy, —$NH_2$, —$CF_3$, —(CO)$R^{13}$ where $R^{13}$ is alkyl, alkoxy, amino, or alkylamino; —$NR^{22}R^{23}$ where $R^{22}$ and $R^{23}$ are independently H, alkyl; or $R^{22}$ and $R^{23}$ are optionally joined to form a 3-6 membered substituted or unsubstituted heterocycle having 1-3 heteroatoms;
Linker is —NH(CO)$NR^{24}$, wherein $R^{24}$ is $C_1$-$C_6$ alkyl;
n is 0-3.

6. A compound, or a pharmaceutically acceptable salt thereof, having the formula:

Formula Ib

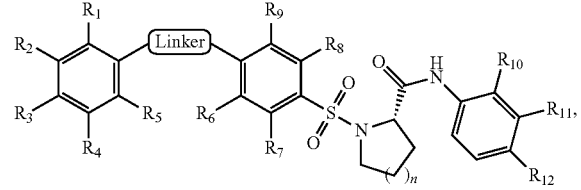

wherein
$R^1$, $R^2$, $R^3$, $R^4$, $R^5$, $R^6$, $R^7$, $R^8$ and $R^9$ are independently H, —OH, alkyl, alkoxy, halogen, —$NH_2$, —$OCF_3$ or —$CF_3$;

$R^{10}$, $R^{11}$ and $R^{12}$ are independently H, —OH, halogen, alkoxy, —NH$_2$, —CF$_3$, —(CO)R$^{13}$ where $R^{13}$ is alkyl, alkoxy, amino, or alkylamino; —NR$^{22}$R$^{23}$, where $R^{22}$ and $R^{23}$ are independently H, alkyl; or $R^{22}$ and $R^{23}$ are optionally joined to form a 3-6 membered substituted or unsubstituted heterocycle having 1-3 heteroatoms;

Linker is —NH(CO)NH—, n is 0-3.

7. A method comprising contacting one or more cells with one or more compounds of Formulas I, III, IV, Ia, or Ib, or a pharmaceutically acceptable salt thereof.

8. The method of claim 7, wherein said compound is any of:

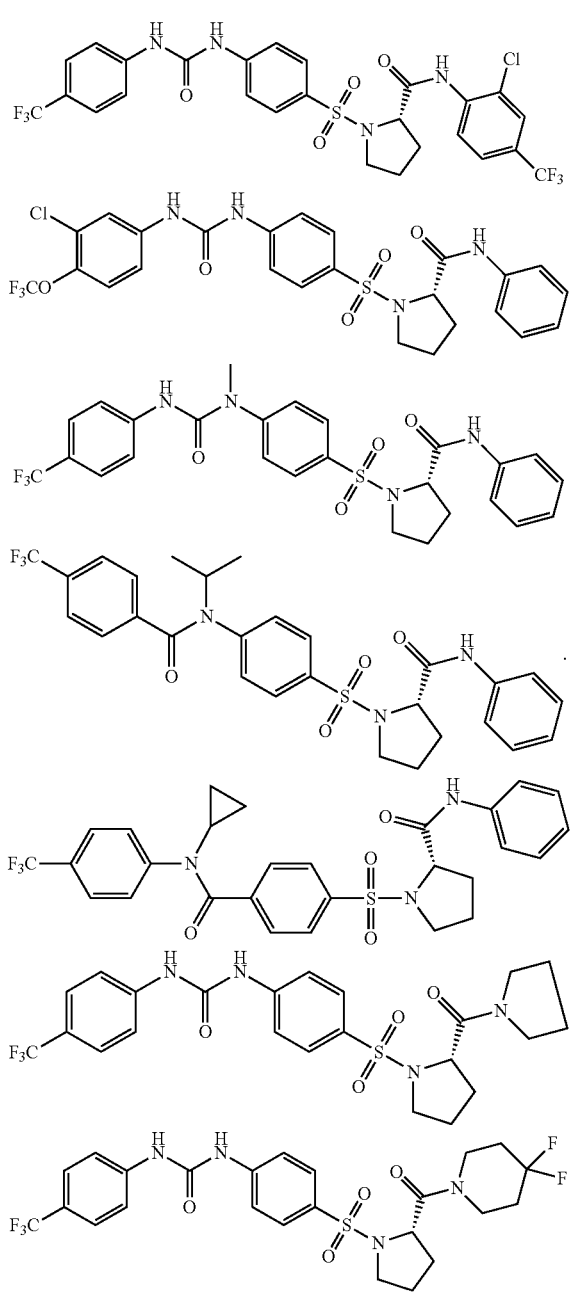

9. The method of claim 7, wherein said method comprises suppressing HIV.

10. A method of treating HIV comprising administering one or more compounds of Formulas I, III, IV, V, Va', Vb', Ia, and Ib, or a pharmaceutically acceptable salt thereof, to a subject.

11. A compound, or a pharmaceutically acceptable salt thereof, having the formula:

Formula V

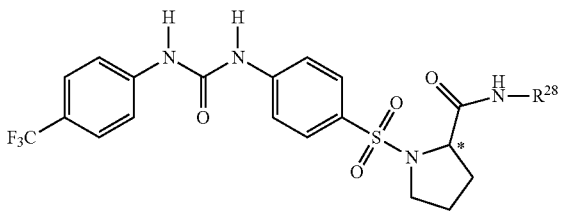

wherein R$^{28}$ is substituted or unsubstituted aryl, wherein the (*) indicates the presence of a chiral carbon.

12. The compound of claim 11, wherein R$^{28}$ is unsubstituted aryl.

13. The compound of claim 12, wherein said compound is a (R)- or (S)-enantiomer, or a combination thereof.

14. The compound of claim 13, wherein said compound is:

Formula Va'

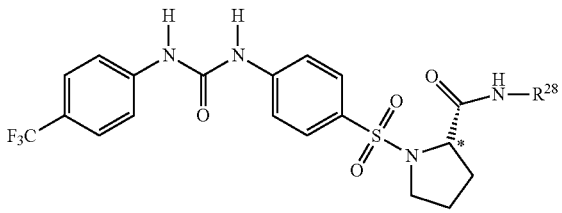

wherein the (*) indicates the presence of a chiral carbon.

15. The compound of claim 14, wherein R$^{28}$ is unsubstituted aryl:

Formula Vb'

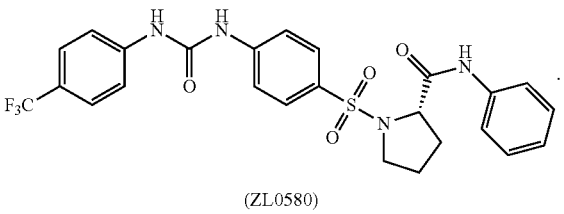

(ZL0580)

* * * * *